(12) United States Patent
Bressi et al.

(10) Patent No.: US 7,381,825 B2
(45) Date of Patent: *Jun. 3, 2008

(54) HISTONE DEACETYLASE INHIBITORS

(75) Inventors: Jerome C. Bressi, San Diego, CA (US); Jason W. Brown, San Diego, CA (US); Sheldon X. Cao, San Diego, CA (US); Anthony R. Gangloff, San Diego, CA (US); Andrew J. Jennings, La Jolla, CA (US); Jeffrey A. Stafford, San Diego, CA (US); Phong H. Vu, San Diego, CA (US); Xiao-Yi Xiao, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 10/803,575

(22) Filed: Mar. 17, 2004

(65) Prior Publication Data

US 2004/0254220 A1 Dec. 16, 2004

Related U.S. Application Data

(60) Provisional application No. 60/455,437, filed on Mar. 17, 2003, provisional application No. 60/531,203, filed on Dec. 19, 2003.

(51) Int. Cl.
*C07D 401/04* (2006.01)
(52) U.S. Cl. .................................................. 546/199
(58) Field of Classification Search .................. 546/199
See application file for complete search history.

(56) References Cited

U.S. PATENT DOCUMENTS

| | | | |
|---|---|---|---|
| 4,482,571 A | 11/1984 | Abraham | |
| 4,997,815 A | 3/1991 | Perrine et al. | |
| 5,124,342 A | 6/1992 | Kerdesky et al. | |
| 5,216,004 A | 6/1993 | Perrine | |
| 5,439,939 A | 8/1995 | Perrine | |
| 5,569,675 A | 10/1996 | Rephaeli et al. | |
| 5,645,852 A | 7/1997 | Newmark | |
| 5,656,644 A | 8/1997 | Adams et al. | |
| 5,700,826 A | 12/1997 | Mjalli et al. | |
| 5,858,365 A | 1/1999 | Faller | |
| 5,922,837 A | 7/1999 | Meinke et al. | |
| 5,939,455 A | 8/1999 | Rephaeli | |
| 5,939,456 A | 8/1999 | Perrine | |
| 5,977,108 A | 11/1999 | Kikuchi et al. | |
| 5,993,845 A | 11/1999 | Geerts et al. | |
| 6,011,000 A | 1/2000 | Perrine et al. | |
| 6,030,961 A | 2/2000 | Nudelman et al. | |
| 6,040,342 A | 3/2000 | Rephaeli et al. | |
| 6,043,277 A | 3/2000 | Rephaeli et al. | |
| 6,043,389 A | 3/2000 | Nudelman et al. | |
| 6,068,987 A | 5/2000 | Dulski et al. | |
| 6,071,923 A | 6/2000 | Nudelman et al. | |
| 6,099,851 A | 8/2000 | Weisman et al. | |
| 6,110,697 A | 8/2000 | Dulski et al. | |
| 6,110,955 A | 8/2000 | Nudelman et al. | |
| 6,110,970 A | 8/2000 | Nudelman et al. | |
| 6,124,495 A | 9/2000 | Neiss et al. | |
| 6,130,248 A | 10/2000 | Nudelman et al. | |
| 6,174,905 B1 | 1/2001 | Suzuki et al. | |
| 6,197,743 B1 | 3/2001 | Faller | |
| 6,231,880 B1 | 5/2001 | Perrine | |
| 6,235,474 B1 | 5/2001 | Feinberg | |
| 6,239,176 B1 | 5/2001 | Nudelman et al. | |
| 6,262,116 B1 | 7/2001 | Pandolfi et al. | |
| 6,287,790 B1 | 9/2001 | Lelievre et al. | |
| 6,329,402 B1 | 12/2001 | Kikuchi et al. | |
| 6,335,170 B1 | 1/2002 | Orntoft | |
| 6,372,957 B1 | 4/2002 | Olson | |
| 6,376,508 B1 | 4/2002 | Li et al. | |
| 6,387,673 B1 | 5/2002 | Evans et al. | |
| 6,399,568 B1 | 6/2002 | Nishino et al. | |
| 6,403,555 B1 | 6/2002 | Skov | |
| 6,428,983 B1 | 8/2002 | Dulski et al. | |
| 6,451,334 B2 | 9/2002 | Perrine et al. | |
| 6,479,629 B2 | 11/2002 | Baldwin et al. | |
| 6,495,719 B2 | 12/2002 | Lan-Hargest et al. | |
| 6,506,574 B1 | 1/2003 | Rambhatla et al. | |
| 6,511,990 B1 | 1/2003 | Breslow et al. | |
| 6,512,123 B2 | 1/2003 | Grossmann et al. | |
| 6,518,012 B1 | 2/2003 | Tomasi | |
| 6,531,472 B2 | 3/2003 | Georges et al. | |
| 6,538,030 B2 | 3/2003 | Chung et al. | |
| 6,541,661 B1 | 4/2003 | Delorme et al. | |
| 6,544,957 B2 | 4/2003 | Kern et al. | |
| 6,548,479 B1 | 4/2003 | Skov | |
| 6,552,065 B2 | 4/2003 | Remiszewski et al. | |

(Continued)

FOREIGN PATENT DOCUMENTS

EP 0 354 549 A2 2/1990

(Continued)

OTHER PUBLICATIONS

Sasho et al. "Preparation and formulation . . . " CA 127:17674 (1997).*

(Continued)

*Primary Examiner*—Celia Chang
(74) *Attorney, Agent, or Firm*—C. Amy Smith

(57) ABSTRACT

Compounds that may be used to inhibit histone deacetylase having the formula

Z-Q-L-M or Z-L-M wherein M is a substituent capable of complexing with a deacetylase catalytic site and/or a metal ion; L is a substituent providing between 0-10 atoms separation between the M substituent and the remainder of the compound; and Z and Q are as defined herein.

33 Claims, 15 Drawing Sheets

U.S. PATENT DOCUMENTS

| | | |
|---|---|---|
| 6,562,995 B1 | 5/2003 | Lan-Hargest et al. |
| 6,599,937 B1 | 7/2003 | Neiss et al. |
| 6,632,628 B1 | 10/2003 | Olson et al. |
| 6,638,530 B1 | 10/2003 | Ishibashi et al. |
| 6,656,905 B1 | 12/2003 | Mori et al. |
| 6,673,587 B1 | 1/2004 | Evans |
| 6,689,558 B2 | 2/2004 | Case |
| 6,699,902 B2 | 3/2004 | Lan-Hargest et al. |
| 6,706,686 B2 | 3/2004 | Long et al. |
| 6,706,762 B1 | 3/2004 | Evans et al. |
| 6,720,445 B2 | 4/2004 | Lan-Hargest et al. |
| 6,777,217 B1 | 8/2004 | Schreiber et al. |
| 6,784,173 B2 | 8/2004 | Leser-Reiff et al. |
| 6,800,638 B2 | 10/2004 | Georges et al. |
| 6,809,118 B2 | 10/2004 | Chung |
| 6,825,317 B2 | 11/2004 | Nishino et al. |
| 6,828,302 B1 | 12/2004 | Skov |
| 6,831,061 B2 | 12/2004 | Lee et al. |
| 6,833,384 B2 | 12/2004 | Remiszewski et al. |
| 6,841,565 B1 | 1/2005 | Lucas et al. |
| 6,869,953 B2 | 3/2005 | Haag et al. |
| 6,875,598 B1 | 4/2005 | Buggy |
| 6,884,597 B1 | 4/2005 | Taya et al. |
| 6,888,027 B2 | 5/2005 | Watkins et al. |
| 6,897,220 B2 | 5/2005 | Delorme et al. |
| 6,900,235 B1 | 5/2005 | Agyin et al. |
| 6,903,112 B2 | 6/2005 | Zhou et al. |
| 6,903,128 B2 | 6/2005 | Duplantier et al. |
| 6,905,669 B2 | 6/2005 | DiMartino |
| 6,916,819 B2 | 7/2005 | Li et al. |
| 6,919,366 B2 | 7/2005 | Sircar |
| 6,943,149 B2 | 9/2005 | Zhang et al. |
| 7,012,078 B2 | 3/2006 | Lowe, III |
| 7,022,728 B2 | 4/2006 | Cowart et al. |
| 7,030,139 B2 | 4/2006 | Cheng et al. |
| 7,030,150 B2 | 4/2006 | Lackey et al. |
| 7,074,786 B2 | 7/2006 | Lemaire et al. |
| 7,169,801 B2 | 1/2007 | Bressi et al. |
| 2001/0009922 A1 | 7/2001 | Faller |
| 2001/0012836 A1 | 8/2001 | Hu et al. |
| 2001/0027215 A1 | 10/2001 | Perrine et al. |
| 2001/0034367 A1 | 10/2001 | Faller et al. |
| 2002/0061860 A1 | 5/2002 | Li et al. |
| 2002/0065282 A1 | 5/2002 | Georges et al. |
| 2002/0076457 A1 | 6/2002 | Aylward |
| 2002/0103192 A1 | 8/2002 | Curtin et al. |
| 2002/0107404 A1 | 8/2002 | Prien et al. |
| 2002/0115177 A1 | 8/2002 | Zhu |
| 2002/0115826 A1 | 8/2002 | Delorme et al. |
| 2002/0119996 A1 | 8/2002 | Lan-Hargest et al. |
| 2002/0120099 A1 | 8/2002 | Nishino et al. |
| 2002/0132792 A1 | 9/2002 | Prien et al. |
| 2002/0137162 A1 | 9/2002 | Li et al. |
| 2002/0137775 A1 | 9/2002 | Lan-Hargest et al. |
| 2002/0143037 A1 | 10/2002 | Lan-Hargest et al. |
| 2002/0143052 A1 | 10/2002 | Lan-Hargest et al. |
| 2002/0143055 A1 | 10/2002 | Lan-Hargest et al. |
| 2002/0143196 A1 | 10/2002 | Lan-Hargest et al. |
| 2002/0161045 A1 | 10/2002 | Lan-Hargest et al. |
| 2002/0164752 A1 | 11/2002 | Meyers |
| 2002/0177594 A1 | 11/2002 | Curtin et al. |
| 2002/0183388 A1 | 12/2002 | Gudas |
| 2002/0183513 A1 | 12/2002 | Grossmann et al. |
| 2003/0013176 A1 | 1/2003 | Pavletich et al. |
| 2003/0013757 A1 | 1/2003 | Leser-Reiff et al. |
| 2003/0017454 A1 | 1/2003 | Sukumar et al. |
| 2003/0018062 A1 | 1/2003 | Remiszewski et al. |
| 2003/0059812 A1 | 3/2003 | Richon et al. |
| 2003/0078216 A1 | 4/2003 | MacLeod et al. |
| 2003/0078369 A1 | 4/2003 | Meinke et al. |
| 2003/0082666 A1 | 5/2003 | Kammer et al. |
| 2003/0082668 A1 | 5/2003 | Tamai et al. |
| 2003/0083521 A1 | 5/2003 | Lan-Hargest et al. |
| 2003/0124101 A1 | 7/2003 | Gu et al. |
| 2003/0125306 A1 | 7/2003 | Lan-Hargest et al. |
| 2003/0129724 A1 | 7/2003 | Grozinger et al. |
| 2003/0134865 A1 | 7/2003 | Adcock et al. |
| 2003/0139404 A1 | 7/2003 | Haag et al. |
| 2003/0143712 A1 | 7/2003 | Verdin et al. |
| 2003/0144276 A1 | 7/2003 | Kikuchi et al. |
| 2003/0144340 A1 | 7/2003 | Long et al. |
| 2003/0148970 A1 | 8/2003 | Besterman et al. |
| 2003/0149261 A1 | 8/2003 | Schramm et al. |
| 2003/0152557 A1 | 8/2003 | Besterman et al. |
| 2003/0154032 A1 | 8/2003 | Pittman et al. |
| 2003/0165903 A1 | 9/2003 | Dang et al. |
| 2003/0165956 A1 | 9/2003 | Stevens et al. |
| 2003/0171409 A1 | 9/2003 | Lan-Hargest et al. |
| 2003/0187027 A1 | 10/2003 | Schreiber et al. |
| 2003/0206946 A1 | 11/2003 | Chung |
| 2003/0207325 A1 | 11/2003 | Guarente et al. |
| 2003/0207791 A1 | 11/2003 | Minucci et al. |
| 2003/0212121 A1 | 11/2003 | Kruger et al. |
| 2003/0216345 A1 | 11/2003 | Nakanishi et al. |
| 2003/0219832 A1 | 11/2003 | Klein et al. |
| 2003/0224040 A1 | 12/2003 | Baylin et al. |
| 2003/0224473 A1 | 12/2003 | McCafferty |
| 2003/0235873 A1 | 12/2003 | Krmer et al. |
| 2004/0002447 A1 | 1/2004 | Levine et al. |
| 2004/0002506 A1 | 1/2004 | Breslow et al. |
| 2004/0005574 A1 | 1/2004 | Guarente et al. |
| 2004/0014647 A1 | 1/2004 | Lee et al. |
| 2004/0018522 A1 | 1/2004 | Dangond et al. |
| 2004/0018968 A1 | 1/2004 | Sgouros et al. |
| 2004/0023944 A1 | 2/2004 | Lan-Hargest et al. |
| 2004/0024067 A1 | 2/2004 | Ramiszewski et al. |
| 2004/0028607 A1 | 2/2004 | Verdin et al. |
| 2004/0029903 A1 | 2/2004 | Lan-Hargest et al. |
| 2004/0029922 A1 | 2/2004 | Lan-Hargest et al. |
| 2004/0043470 A1 | 3/2004 | Xiao |
| 2004/0053820 A1 | 3/2004 | Nakajima et al. |
| 2004/0053960 A1 | 3/2004 | Georges et al. |
| 2004/0058868 A1 | 3/2004 | James et al. |
| 2004/0072735 A1 | 4/2004 | Richon et al. |
| 2004/0072770 A1 | 4/2004 | Besterman et al. |
| 2004/0072849 A1 | 4/2004 | Schreiber et al. |
| 2004/0077046 A1 | 4/2004 | Cohen et al. |
| 2004/0077083 A1 | 4/2004 | Watt |
| 2004/0077084 A1 | 4/2004 | Watt et al. |
| 2004/0077578 A1 | 4/2004 | Monia et al. |
| 2004/0077591 A1 | 4/2004 | Dangond |
| 2004/0077698 A1 | 4/2004 | Georges et al. |
| 2004/0077726 A1 | 4/2004 | Watkins et al. |
| 2004/0081976 A1 | 4/2004 | Sidransky |
| 2004/0087631 A1 | 5/2004 | Bacopoulos et al. |
| 2004/0087652 A1 | 5/2004 | Gottlicher et al. |
| 2004/0087657 A1 | 5/2004 | Richon et al. |
| 2004/0091951 A1 | 5/2004 | Schultz |
| 2004/0091953 A1 | 5/2004 | Verdin et al. |
| 2004/0091967 A1 | 5/2004 | Kohler |
| 2004/0092431 A1 | 5/2004 | Hellberg |
| 2004/0092558 A1 | 5/2004 | Klimko et al. |
| 2004/0092572 A1 | 5/2004 | Renaud et al. |
| 2004/0092598 A1 | 5/2004 | Watkins et al. |
| 2004/0097439 A9 | 5/2004 | Nicolas et al. |
| 2004/0102458 A1 | 5/2004 | Chiosis et al. |
| 2004/0106599 A1 | 6/2004 | Delorme et al. |
| 2004/0122079 A1 | 6/2004 | Grossmann et al. |
| 2004/0122101 A1 | 6/2004 | Miller et al. |
| 2004/0127522 A1 | 7/2004 | Chiao et al. |
| 2004/0127523 A1 | 7/2004 | Bacopoulos et al. |
| 2004/0127571 A1 | 7/2004 | Bhalla et al. |
| 2004/0138270 A1 | 7/2004 | George et al. |
| 2004/0157841 A1 | 8/2004 | Fertig et al. |

| Publication No. | Date | Inventor |
|---|---|---|
| 2004/0157924 A1 | 8/2004 | Lan-Hargest et al. |
| 2004/0157930 A1 | 8/2004 | Mascagni et al. |
| 2004/0161787 A1 | 8/2004 | Michnick et al. |
| 2004/0162317 A1 | 8/2004 | Fertig et al. |
| 2004/0167184 A1 | 8/2004 | Wiech et al. |
| 2004/0180962 A1 | 9/2004 | Truog |
| 2004/0186049 A1 | 9/2004 | Long et al. |
| 2004/0186274 A1 | 9/2004 | Allis et al. |
| 2004/0192744 A1 | 9/2004 | Haag et al. |
| 2004/0197888 A1 | 10/2004 | Amour et al. |
| 2004/0198830 A1 | 10/2004 | Watkins et al. |
| 2004/0204339 A1 | 10/2004 | DiMartino |
| 2004/0204373 A1 | 10/2004 | Monia et al. |
| 2004/0213826 A1 | 10/2004 | Marx et al. |
| 2004/0214862 A1 | 10/2004 | Leser-Reiff et al. |
| 2004/0214880 A1 | 10/2004 | Fertig et al. |
| 2004/0224991 A1 | 11/2004 | Lu et al. |
| 2004/0229889 A1 | 11/2004 | Urano et al. |
| 2004/0254220 A1 | 12/2004 | Bressi et al. |
| 2004/0259772 A1 | 12/2004 | Fojo et al. |
| 2004/0266718 A1 | 12/2004 | Li et al. |
| 2004/0266769 A1 | 12/2004 | Bressi et al. |
| 2004/0266818 A1 | 12/2004 | Breslow et al. |
| 2005/0003031 A1 | 1/2005 | Aylward |
| 2005/0009030 A1 | 1/2005 | Schweighoffer et al. |
| 2005/0020557 A1 | 1/2005 | Johnson, Jr. et al. |
| 2005/0026907 A1 | 2/2005 | Wash et al. |
| 2005/0032794 A1 | 2/2005 | Padia et al. |
| 2005/0032831 A1 | 2/2005 | Kozikowski et al. |
| 2005/0032899 A1 | 2/2005 | Chen et al. |
| 2005/0037992 A1 | 2/2005 | Lyons et al. |
| 2005/0038113 A1 | 2/2005 | Groner et al. |
| 2005/0059682 A1 | 3/2005 | Rubinfeld |
| 2005/0065596 A1 | 3/2005 | Tseng et al. |
| 2005/0070467 A1 | 3/2005 | Naoe |
| 2005/0079995 A1 | 4/2005 | Bedaloy et al. |
| 2005/0080249 A1 | 4/2005 | Buggy |
| 2005/0084967 A1 | 4/2005 | Berenson et al. |
| 2005/0085507 A1 | 4/2005 | Remiszewski et al. |
| 2005/0085515 A1 | 4/2005 | Watkins et al. |
| 2005/0096468 A1 | 5/2005 | Van Emelen et al. |
| 2005/0106654 A1 | 5/2005 | Olson et al. |
| 2005/0107348 A1 | 5/2005 | Lan-Hargest et al. |
| 2005/0107384 A1 | 5/2005 | Angibaud et al. |
| 2005/0107445 A1 | 5/2005 | Watkins et al. |
| 2005/0113373 A1 | 5/2005 | Van Emelen et al. |
| 2005/0118596 A1 | 6/2005 | Asselbergs et al. |
| 2005/0119250 A1 | 6/2005 | Angibaud et al. |
| 2005/0124679 A1 | 6/2005 | Kim et al. |
| 2005/0130146 A1 | 6/2005 | Zelent et al. |
| 2005/0131018 A1 | 6/2005 | Sendzik et al. |
| 2005/0136090 A1 | 6/2005 | Falotico et al. |
| 2005/0137232 A1 | 6/2005 | Bressi et al. |
| 2005/0137234 A1 | 6/2005 | Bressi et al. |
| 2005/0143385 A1 | 6/2005 | Watkins et al. |
| 2005/0148613 A1 | 7/2005 | Van Emelen et al. |
| 2005/0159347 A1 | 7/2005 | DiMartino |
| 2005/0159470 A1 | 7/2005 | Bressi et al. |
| 2005/0165016 A1 | 7/2005 | Van Emelen |
| 2005/0171027 A1 | 8/2005 | Sinclair et al. |
| 2005/0171042 A1 | 8/2005 | Monia et al. |
| 2005/0171103 A1 | 8/2005 | Stokes et al. |
| 2005/0171208 A1 | 8/2005 | Lan-Hargest et al. |
| 2005/0171347 A1 | 8/2005 | Emelen et al. |
| 2005/0176686 A1 | 8/2005 | Maurer et al. |
| 2005/0176764 A1 | 8/2005 | Mataki et al. |
| 2005/0187261 A1 | 8/2005 | Vemer et al. |
| 2005/0191713 A1 | 9/2005 | Sasakawa et al. |

FOREIGN PATENT DOCUMENTS

| | | | |
|---|---|---|---|
| EP | 0 378 991 A1 | 7/1990 |
| EP | 0570594 A | 11/1993 |
| EP | 0 847 992 A1 | 6/1998 |
| WO | WO 97/11366 A1 | 3/1987 |
| WO | WO 96/15096 A1 | 5/1996 |
| WO | WO 97/02244 A1 | 1/1997 |
| WO | WO 97/29776 A1 | 8/1997 |
| WO | WO 97/35990 A2 | 10/1997 |
| WO | WO 97/35990 A3 | 10/1997 |
| WO | WO 97/47307 A1 | 12/1997 |
| WO | WO 98/00127 A1 | 1/1998 |
| WO | WO 98/28269 A1 | 7/1998 |
| WO | WO 98/29114 A1 | 7/1998 |
| WO | WO 98/39966 A1 | 9/1998 |
| WO | WO 98/40065 A1 | 9/1998 |
| WO | WO 98/40080 A1 | 9/1998 |
| WO | WO 98/48825 A1 | 11/1998 |
| WO | WO 98/55449 A1 | 12/1998 |
| WO | WO 99/11659 A1 | 3/1999 |
| WO | WO 99/23885 A1 | 5/1999 |
| WO | WO 99/37150 A1 | 7/1999 |
| WO | WO 99/61413 A1 | 12/1999 |
| WO | WO 00/08048 A2 | 2/2000 |
| WO | WO 00/08048 A3 | 2/2000 |
| WO | WO 00/10583 A1 | 3/2000 |
| WO | WO 00/21979 A2 | 4/2000 |
| WO | WO 00/21979 A3 | 4/2000 |
| WO | WO 00/23567 A2 | 4/2000 |
| WO | WO 00/23567 A3 | 4/2000 |
| WO | WO 00/52033 A1 | 9/2000 |
| WO | WO 00/56917 A1 | 9/2000 |
| WO | WO 00/61576 A1 | 10/2000 |
| WO | WO 00/71703 A2 | 11/2000 |
| WO | WO 00/71703 A3 | 11/2000 |
| WO | WO 01/07042 A1 | 2/2001 |
| WO | WO 01/14581 A3 | 3/2001 |
| WO | WO 01/16106 A1 | 3/2001 |
| WO | WO 01/17514 A1 | 3/2001 |
| WO | WO 01/18045 | 3/2001 |
| WO | WO 01/18045 A1 | 3/2001 |
| WO | WO 01/18171 A2 | 3/2001 |
| WO | WO 01/18171 A3 | 3/2001 |
| WO | WO 01/27314 A1 | 4/2001 |
| WO | WO 01/38322 A1 | 5/2001 |
| WO | WO 01/42437 A2 | 6/2001 |
| WO | WO 01/42437 A3 | 6/2001 |
| WO | WO 01/67107 A1 | 9/2001 |
| WO | WO 01/70675 | 9/2001 |
| WO | WO 01/70675 A3 | 9/2001 |
| WO | WO 01/72737 A1 | 10/2001 |
| WO | WO 01/72784 A2 | 10/2001 |
| WO | WO 01/72784 A3 | 10/2001 |
| WO | WO 02/06307 A1 | 1/2002 |
| WO | WO 02/07722 A2 | 1/2002 |
| WO | WO 02/07722 A3 | 1/2002 |
| WO | WO 02/08273 A2 | 1/2002 |
| WO | WO 02/08273 A3 | 1/2002 |
| WO | WO 02/15921 A2 | 2/2002 |
| WO | WO 02/15921 A3 | 2/2002 |
| WO | WO 02/22133 A1 | 3/2002 |
| WO | WO 02/22577 A3 | 3/2002 |
| WO | WO 02/26696 | 4/2002 |
| WO | WO 02/26696 A1 | 4/2002 |
| WO | WO 02/26703 A1 | 4/2002 |
| WO | WO 02/30879 A2 | 4/2002 |
| WO | WO 02/30879 A3 | 4/2002 |
| WO | WO 02/30970 A2 | 4/2002 |
| WO | WO 02/30970 A3 | 4/2002 |
| WO | WO 02/36075 A2 | 5/2002 |
| WO | WO 02/36075 A3 | 5/2002 |
| WO | WO 02/36783 A2 | 5/2002 |
| WO | WO 02/36783 A3 | 5/2002 |
| WO | WO 02/46129 A2 | 6/2002 |
| WO | WO 02/46129 A3 | 6/2002 |
| WO | WO 02/46144 A1 | 6/2002 |

| | | | | | | | |
|---|---|---|---|---|---|---|---|
| WO | WO 02/50244 | A3 | 6/2002 | WO | WO 03/087057 | A1 | 10/2003 |
| WO | WO 02/50285 | | 6/2002 | WO | WO 03/087066 | A1 | 10/2003 |
| WO | WO 02/051842 | A1 | 7/2002 | WO | WO 03/088954 | A1 | 10/2003 |
| WO | WO 02/055017 | A3 | 7/2002 | WO | WO 03/092686 | A1 | 11/2003 |
| WO | WO 02/055688 | A2 | 7/2002 | WO | WO 03/099210 | A3 | 12/2003 |
| WO | WO 02/055688 | A3 | 7/2002 | WO | WO 03/099272 | A1 | 12/2003 |
| WO | WO 02/060430 | A1 | 8/2002 | WO | WO 03/099760 | A1 | 12/2003 |
| WO | WO 02/062773 | A1 | 8/2002 | WO | WO 03/099789 | A1 | 12/2003 |
| WO | WO 02/069947 | A2 | 9/2002 | WO | WO 03/100089 | A1 | 12/2003 |
| WO | WO 02/069947 | A3 | 9/2002 | WO | WO 03/103613 | A2 | 12/2003 |
| WO | WO 02/076941 | A2 | 10/2002 | WO | WO 03/103613 | A3 | 12/2003 |
| WO | WO 02/076941 | A3 | 10/2002 | WO | WO 03/103712 | A1 | 12/2003 |
| WO | WO 02/083173 | A1 | 10/2002 | WO | WO 04/001072 | A2 | 12/2003 |
| WO | WO 02/085400 | A1 | 10/2002 | WO | WO 2004/002944 | A1 | 1/2004 |
| WO | WO 02/085883 | A1 | 10/2002 | WO | WO 2004/005282 | A1 | 1/2004 |
| WO | WO 02/089782 | A2 | 11/2002 | WO | WO 2004/005513 | A2 | 1/2004 |
| WO | WO 02/089782 | A3 | 11/2002 | WO | WO 2004/006909 | A1 | 1/2004 |
| WO | WO 02090534 | A1 | 11/2002 | WO | WO 2004/009092 | A1 | 1/2004 |
| WO | WO 02/102316 | A2 | 12/2002 | WO | WO 2004/009536 | A1 | 1/2004 |
| WO | WO 02/102316 | A3 | 12/2002 | WO | WO 2004/009771 | A2 | 1/2004 |
| WO | WO 02/102323 | A2 | 12/2002 | WO | WO 2004/013130 | A1 | 2/2004 |
| WO | WO 02/102984 | A2 | 12/2002 | WO | WO 2004/017996 | A1 | 3/2004 |
| WO | WO 02/102984 | A3 | 12/2002 | WO | WO 2004/020460 | A1 | 3/2004 |
| WO | WO 03/000715 | A1 | 1/2003 | WO | WO 2004/024160 | A1 | 3/2004 |
| WO | WO 03/006652 | A2 | 1/2003 | WO | WO 2004/026234 | A2 | 4/2004 |
| WO | WO 03/006652 | A3 | 1/2003 | WO | WO 2004/027418 | A3 | 4/2004 |
| WO | WO 03/011851 | A3 | 2/2003 | WO | WO 2004/029622 | A2 | 4/2004 |
| WO | WO 03/013493 | A1 | 2/2003 | WO | WO 2004/031388 | A1 | 4/2004 |
| WO | WO 03/014340 | A2 | 2/2003 | WO | WO 2004/035525 | A1 | 4/2004 |
| WO | WO 03/014340 | A3 | 2/2003 | WO | WO 2004/043348 | A2 | 5/2004 |
| WO | WO 03/015810 | A1 | 2/2003 | WO | WO 2004043352 | A2 | 5/2004 |
| WO | WO 03/024442 | A2 | 3/2003 | WO | WO 2004/046094 | | 6/2004 |
| WO | WO 03/024442 | A3 | 3/2003 | WO | WO 2004/046094 | A1 | 6/2004 |
| WO | WO 03/024448 | A2 | 3/2003 | WO | WO 2004/046104 | A2 | 6/2004 |
| WO | WO 03/024448 | A3 | 3/2003 | WO | WO 2004/046312 | A2 | 6/2004 |
| WO | WO 03/029451 | A2 | 4/2003 | WO | WO 2004/052292 | A2 | 6/2004 |
| WO | WO 03/029451 | A3 | 4/2003 | WO | WO 2004/052838 | A1 | 6/2004 |
| WO | WO 03/032921 | A2 | 4/2003 | WO | WO 2004/053140 | A2 | 6/2004 |
| WO | WO 03/032921 | A3 | 4/2003 | WO | WO 2004/054999 | A1 | 7/2004 |
| WO | WO 03/033678 | A3 | 4/2003 | WO | WO 2004/056877 | A1 | 7/2004 |
| WO | WO 03/039599 | A1 | 5/2003 | WO | WO 2004/063146 | A1 | 7/2004 |
| WO | WO 03/046207 | A2 | 6/2003 | WO | WO 2004/063169 | A1 | 7/2004 |
| WO | WO 03/048774 | A1 | 6/2003 | WO | WO 2004/064727 | A2 | 8/2004 |
| WO | WO 03/053468 | A1 | 7/2003 | WO | WO 2004/065354 | A1 | 8/2004 |
| WO | WO 03/057722 | A2 | 7/2003 | WO | WO 2004/067480 | A2 | 8/2004 |
| WO | WO 03/057722 | A3 | 7/2003 | WO | WO 2004/069133 | A2 | 8/2004 |
| WO | WO 03/059864 | A2 | 7/2003 | WO | WO 2004/069803 | A2 | 8/2004 |
| WO | WO 03/059864 | A3 | 7/2003 | WO | WO 2004/069823 | A1 | 8/2004 |
| WO | WO 03/066579 | A2 | 8/2003 | WO | WO 2004/070351 | A2 | 8/2004 |
| WO | WO 03/066579 | A3 | 8/2003 | WO | WO 2004/071400 | A2 | 8/2004 |
| WO | WO 03/066885 | A2 | 8/2003 | WO | WO 2004/071401 | A2 | 8/2004 |
| WO | WO 03/066885 | A3 | 8/2003 | WO | WO 2004/071443 | A2 | 8/2004 |
| WO | WO 03/066889 | A2 | 8/2003 | WO | WO 2004/071464 | A2 | 8/2004 |
| WO | WO 03/066889 | A3 | 8/2003 | WO | WO 2004/072047 | A1 | 8/2004 |
| WO | WO 03/070188 | A2 | 8/2003 | WO | WO 2004/072265 | A2 | 8/2004 |
| WO | WO 03/070188 | A3 | 8/2003 | WO | WO 2004/074478 | A1 | 9/2004 |
| WO | WO 03/070691 | A1 | 8/2003 | WO | WO 2004/076386 | A2 | 9/2004 |
| WO | WO 03/070754 | A1 | 8/2003 | WO | WO 2004/082638 | A2 | 9/2004 |
| WO | WO 03/075839 | A2 | 9/2003 | WO | WO 2004/089293 | A2 | 10/2004 |
| WO | WO 03/075839 | A3 | 9/2003 | WO | WO 2004/092115 | A2 | 10/2004 |
| WO | WO 03/075929 | A1 | 9/2003 | WO | WO 2004/098495 | A2 | 11/2004 |
| WO | WO 03/076395 | A1 | 9/2003 | WO | WO 2004/103358 | A2 | 12/2004 |
| WO | WO 03/076400 | A1 | 9/2003 | WO | WO 2004/103369 | A1 | 12/2004 |
| WO | WO 03/076401 | A1 | 9/2003 | WO | WO 2004/110418 | A2 | 12/2004 |
| WO | WO 03/076421 | A1 | 9/2003 | WO | WO 2004/112763 | A2 | 12/2004 |
| WO | WO 03/076422 | A1 | 9/2003 | WO | WO 2004/113336 | A1 | 12/2004 |
| WO | WO 03/076430 | A1 | 9/2003 | WO | WO 2005/000213 | A2 | 1/2005 |
| WO | WO 03/076438 | A1 | 9/2003 | WO | WO 2005/000282 | A2 | 1/2005 |
| WO | WO 03/080864 | A1 | 10/2003 | WO | WO 2005/000289 | A1 | 1/2005 |
| WO | WO 03/082288 | A1 | 10/2003 | WO | WO 2005/000332 | A2 | 1/2005 |
| WO | WO 03/083067 | A2 | 10/2003 | WO | WO 2005/002555 | A2 | 1/2005 |
| WO | WO 03/084611 | A1 | 10/2003 | WO | WO 2005/002672 | A2 | 1/2005 |
| WO | WO 03/086397 | A1 | 10/2003 | WO | WO 2005/004861 | A1 | 1/2005 |

| | | |
|---|---|---|
| WO | WO 2005/007091 A2 | 1/2005 |
| WO | WO 2005/007158 A1 | 1/2005 |
| WO | WO 2005/009349 A2 | 2/2005 |
| WO | WO 2005/011598 A2 | 2/2005 |
| WO | WO 2005/011661 A1 | 2/2005 |
| WO | WO 2005/013958 A1 | 2/2005 |
| WO | WO 2005/014004 A1 | 2/2005 |
| WO | WO 2005/014588 A1 | 2/2005 |
| WO | WO 2005/016264 A2 | 2/2005 |
| WO | WO 2005/016342 A1 | 2/2005 |
| WO | WO 2005/018578 A2 | 3/2005 |
| WO | WO 2005/019174 | 3/2005 |
| WO | WO 2005/019174 A1 | 3/2005 |
| WO | WO 2005/023179 A2 | 3/2005 |
| WO | WO 2005/025619 A1 | 3/2005 |
| WO | WO 2005/028447 A1 | 3/2005 |
| WO | WO 2005/028620 A2 | 3/2005 |
| WO | WO 2005/030704 A1 | 4/2005 |
| WO | WO 2005/030705 A1 | 4/2005 |
| WO | WO 2005/034880 | 4/2005 |
| WO | WO 2005/034880 A2 | 4/2005 |
| WO | WO 2005/039498 A2 | 5/2005 |
| WO | WO 2005/040101 | 5/2005 |
| WO | WO 2005/040101 A1 | 5/2005 |
| WO | WO 2005/040136 A1 | 5/2005 |
| WO | WO 2005/040161 | 5/2005 |
| WO | WO 2005/040161 A1 | 5/2005 |
| WO | WO 2005/047457 A2 | 5/2005 |
| WO | WO 2005/051901 A1 | 6/2005 |
| WO | WO 2005/053609 A2 | 6/2005 |
| WO | WO 2005/053610 A2 | 6/2005 |
| WO | WO 2005/055928 A2 | 6/2005 |
| WO | WO 2005/055928 A3 | 6/2005 |
| WO | WO 2005/058298 A2 | 6/2005 |
| WO | WO 2005/058803 A1 | 6/2005 |
| WO | WO 2005/065681 A1 | 7/2005 |
| WO | WO 2005/066151 A2 | 7/2005 |
| WO | WO 2005/071079 A1 | 8/2005 |
| WO | WO 2005/073180 | 8/2005 |

OTHER PUBLICATIONS

Wood et al. "Substrate activity screening . . . " CA 143:452160 (2005).*

Asano et al. "Preparation of fused imidazole . . . " CA 134:31502 (2001).*

Vourloumis et al. "Solid phase synthesis . . . " Ca 139:133505 (2003).*

Vourloumis et al. "Solid phase synthesis of benzimidazole . . . " Tetrahedron Lett. v. 44 p. 2807-2811 (2003).*

Dai Yujia et al. "INdole amide hydroxamic acids as potent inhibitors of histone deacetylases." Bioorganic and Medicinal Chemistry Letters, vol. 13, No. 11, Jun. 2, 2003, pp. 1897-1901, XP002331281 ISSN; 0960-894X abstract; figures 1,2; tables 1-4.

Database Beilstein Institut Zur Forderung Der Wissenchaften, Frankfurt am Main, DE; Dec. 2, 1991, XP002331282 Database accession No. 4311238 abstract.

Database Beilstein Institut Zur Forderung Der Wissenchaften, Frankfurt am Main, DE; Dec. 2, 1991, XP002331283 Database accession No. 5815061 abstract.

Database Beilstein Institut Zur Forderung Der Wissenchaften, Frankfurt am Main, DE; Dec. 2, 1991, XP002331284 Database accession No. 7765459 abstract.

Database Caplus Chemical Abstracts Service, Columbus, Ohio, US; 2002 XP002325919 Database accession No. AN:2002:217200.

Lam, Patrick Y.S. et al. "Structure-based design of novel guanidine/benzamidine mimics: potent and orally bioavailable factor Xa inhibitors as novel anticogulants" Journal of Medical Chemistry (2003), 46 (21) 4405-4418, CASREACT 140; 12453.

Patent Abstracts of Japan for Publication No. 03289654 A; Published Dec. 19, 1991. "Silver Halide Color Photographic Sensitive Material" Yamazaki et al.

Patent Abstracts of Japan of Publication No. 11095383 A; Published Apr. 9, 1999. "Silver Hadide Color Photographic Sensitive Material and Image Forming Method" Ofuku et al.

Koruznjak et al., "Novel Derivatives of Benzo(b)thieno[2,3-c]quinolones: Synthesis, Photochemical Synthesis, and Antitumor Evaluation," J. Med. Chem., vol. 46, No. 21, pp. 4516-4524 (2003).

Wright et al., The Preparation of 3-Chlorobenzo[b]thiophene Derivatives from Cinnamic Acids, J. Heterocyclic Chem., vol. 8, No. 5, pp. 711-714 (1971).

* cited by examiner

FIGURE 3

SEQ. ID No. 1

MSYYHHHHHHDYDIPTTENLYFQGAMEPGGSMAQTQGTRRKVCYYYDGDVGNYYYGQGHP
MKPHRIRMTHNLLLNYGLYRKMEIYRPHKANAEEMTKYHSDDYIKFLRSIRPDNMSEYSK
QMQRFNVGEDCPVFDGLFEFCQLSTGGSVASAVKLNKQQTDIAVNWAGGLHHAKKSEASG
FCYVNDIVLAILELLKYHQRVLYIDIDIHHGDGVEEAFYTTDRVMTVSFHKYGEYFPGTG
DLRDIGAGKGKYYAVNYPLRDGIDDESYEAIFKPVMSKVMEMFQPSAVVLQCGSDSLSGD
RLGCFNLTIKGHAKCVEFVKSFNLPMLMLGGGGYTIRNVARCWTYETAVALDTEIPNELP
YNDYFEYFGPDFKLHISPSNMTNQNTNEYLEKIKQRLFENLRMLPHAPGVQMQAIPEDAI
PEESGDEDEDDPDKRISICSSDKRIACEEEFSDSEEEGEGGRKNSSNFKKAKRVKTEDEK
EKDPEEKKEVTEEEKTKEEKPEAKGVKEEVKLA

FIGURE 4

SEQ. ID No. 2

ATGTCGTACTACCATCACCATCACCATCACGATTACGATATCCCAACGACCGAAAACCTG
TATTTTCAGGGCGCCATGGAACCCGGGGGATCCATGGCGCAGACGCAGGGCACCCGGAGG
AAAGTCTGTTACTACTACGACGGGGATGTTGGAAATTACTATTATGGACAAGGCCACCCA
ATGAAGCCTCACCGAATCCGCATGACTCATAATTTGCTGCTCAACTATGGTCTCTACCGA
AAAATGGAAATCTATCGCCCTCACAAAGCCAATGCTGAGGAGATGACCAAGTACCACAGC
GATGACTACATTAAATTCTTGCGCTCCATCCGTCCAGATAACATGTCGGAGTACAGCAAG
CAGATGCAGAGATTCAACGTTGGTGAGGACTGTCCAGTATTCGATGGCCTGTTTGAGTTC
TGTCAGTTGTCTACTGGTGGTTCTGTGGCAAGTGCTGTGAAACTTAATAAGCAGCAGACG
GACATCGCTGTGAATTGGGCTGGGGGCCTGCACCATGCAAAGAAGTCCGAGGCATCTGGC
TTCTGTTACGTCAATGATATCGTCTTGGCCATCCTGGAACTGCTAAAGTATCACCAGAGG
GTGCTGTACATTGACATTGATATTCACCATGGTGACGGCGTGGAAGAGGCCTTCTACACC
ACGGACCGGGTCATGACTGTGTCCTTTCATAAGTATGGAGAGTACTTCCCAGGAACTGGG
GACCTACGGGATATCGGGGCTGGCAAAGGCAAGTATTATGCTGTTAACTACCCGCTCCGA
GACGGGATTGATGACGAGTCCTATGAGGCCATTTTCAAGCCGGTCATGTCCAAAGTAATG
GAGATGTTCCAGCCTAGTGCGGTGGTCTTACAGTGTGGCTCAGACTCCCTATCTGGGGAT
CGGTTAGGTTGCTTCAATCTAACTATCAAGGACACGCCAAGTGTGTGGAATTTGTCAAG
AGCTTTAACCTGCCTATGCTGATGCTGGGAGGCGGTGGTTACACCATTCGTAACGTTGCC
CGGTGCTGGACATATGAGACAGCTGTGGCCCTGGATACGGAGATCCCTAATGAGCTTCCA
TACAATGACTACTTTGAATACTTTGGACCAGATTTCAAGCTCCACATCAGTCCTTCCAAT
ATGACTAACCAGAACACGAATGAGTACCTGGAGAAGATCAAACAGCGACTGTTTGAGAAC
CTTAGAATGCTGCCGCACGCACCTGGGGTCCAAATGCAGGCGATTCCTGAGGACGCCATC
CCTGAGGAGAGTGGCGATGAGGACGAAGACGACCCTGACAAGCGCATCTCGATCTGCTCC
TCTGACAAACGAATTGCCTGTGAGGAAGAGTTCTCCGATTCTGAAGAGGAGGGAGAGGGG
GGCCGCAAGAACTCTTCCAACTTCAAAAAGCCAAGAGAGTCAAAACAGAGGATGAAAAA
GAGAAAGACCCAGAGGAGAAGAAAGAAGTCACCGAAGAGGAGAAAACCAAGGAGGAGAAG
CCAGAAGCCAAAGGGGTCAAGGAGGAGGTCAAGTTGGCCTGA

FIGURE 5

SEQ. ID No. 3

MGSMAYSQGGGKKKVCYYYDGDIGNYYYGQGHPMKPHRIRMTHNLLLNYGLYRKMEIYRP
HKATAEEMTKYHSDEYIKFLRSIRPDNMSEYSKQMQRFNVGEDCPVFDGLFEFCQLSTGG
SVAGAVKLNRQQTDMAVNWAGGLHHAKKSEASGFCYVNDIVLAILELLKYHQRVLYIDID
IHHGDGVEEAFYTTDRVMTVSFHKYGEYFPGTGDLRDIGAGKGKYYAVNFPMRDGIDDES
YGQIFKPIISKVMEMYQPSAVVLQCGADSLSGDRLGCFNLTVKGHAKCVEVVKTFNLPLL
MLGGGGYTIRNVARCWTYETAVALDCEIPNELPYNDYFEYFGPDFKLHISPSNMTNQNTP
EYMEKIKQRLFENLRMLPHAPGVQMQAIPEDAVHEDSGDEDGEDPDKRISIRASDKRIAC
DEEFSDSEDEGEGGRRNVADHKKGAKKARIEEDKKETEDKKTDVKEEDKSKDNSGEKTDT
KGTKSEQLSNPGHHHHHH

FIGURE 6

SEQ. ID No. 4

ATGGGATCCATGGCGTACAGTCAAGGAGGCGGCAAAAAAAAGTCTGCTACTACTACGAC
GGTGATATTGGAAATTATTATTATGGACAGGGTCATCCCATGAAGCCTCATAGAATCCGC
ATGACCCATAACTTGCTGTTAAATTATGGCTTATACAGAAAAATGGAAATATATAGGCCC
CATAAAGCCACTGCCGAAGAAATGACAAAATATCACAGTGATGAGTATATCAAATTTCTA
CGGTCAATAAGACCAGATAACATGTCTGAGTATAGTAAGCAGATGCAGAGATTTAATGTT
GGAGAAGATTGTCCAGTGTTTGATGGACTCTTTGAGTTTTGTCAGCTCTCAACTGGCGGT
TCAGTTGCTGGAGCTGTGAAGTTAAACCGACAACAGACTGATATGGCTGTTAATTGGGCT
GGAGGATTACATCATGCTAAGAAATCAGAAGCATCAGGATTCTGTTACGTTAATGATATT
GTGCTTGCCATCCTTGAATTACTAAAGTATCATCAGAGAGTCTTATATATTGATATAGAT
ATTCATCATGGTGATGGTGTTGAAGAAGCTTTTTATACAACAGATCGTGTAATGACGGTA
TCATTCCATAAATATGGGGAATACTTTCCTGGCACAGGAGACTTGAGGGATATTGGTGCT
GGAAAAGGCAAATACTATGCTGTCAATTTTCCAATGAGAGATGGTATAGATGATGAGTCA
TATGGGCAGATATTTAAGCCTATTATCTCAAAGGTGATGGAGATGTATCAACCTAGTGCT
GTGGTATTACAGTGTGGTGCAGACTCATTATCTGGTGATAGACTGGGTTGTTTCAATCTA
ACAGTCAAAGGTCATGCTAAATGTGTAGAAGTTGTAAAAACTTTTAACTTACCATTACTG
ATGCTTGGAGGAGGTGGCTACACAATCCGTAATGTTGCTCGATGTTGGACATATGAGACT
GCAGTTGCCCTTGATTGTGAGATTCCCAATGAGTTGCCATATAATGATTACTTTGAGTAT
TTTGGACCAGACTTCAAACTGCATATTAGTCCTTCAAACATGACAAACCAGAACACTCCA
GAATATATGGAAAAGATAAAACAGCGTTTGTTTGAAAATTTGCGCATGTTACCTCATGCA
CCTGGTGTCCAGATGCAAGCTATTCCAGAAGATGCTGTTCATGAAGACAGTGGAGATGAA
GATGGAGAAGATCCAGACAAGAGAATTTCTATTCGAGCATCAGACAAGCGGATAGCTTGT
GATGAAGAATTCTCAGATTCTGAGGATGAAGGAGAAGGAGGTCGAAGAAATGTGGCTGAT
CATAAGAAAGGAGCAAAGAAAGCTAGAATTGAAGAAGATAAGAAAGAAACAGAGGACAAA
AAAACAGACGTTAAGGAAGAAGATAAATCCAAGGACAACAGTGGTGAAAAAACAGATACC
AAAGGAACCAAATCAGAACAGCTCAGCAACCCCGGGCATCACCATCACCATCACTAA

FIGURE 7

SEQ. ID No. 5

MPGMDLNLEAEALAGTGLVLDEQLNEFHCLWDDSFPEGPERLHAIKEQLIQEGLLDRCVS
FQARFAEKEELMLVHSLEYIDLMETTQYMNEGELRVLADTYDSVYLHPNSYSCACLASGS
VLRLVDAVLGAEIRNGMAIIRPPGHHAQHSLMDGYCMFNHVAVAARYAQQKHRIRRVLIV
DWDVHHGQGTQFTFDQDPSVLYFSIHRYEQGRFWPHLKASNWSTTGFGQGQGYTINVPWN
QVGMRDADYIAAFLHVLLPVALEFQPQLVLVAAGFDALQGDPKGEMAATPAGFAQLTHLL
MGLAGGKLILSLEGGYNLRALAEGVSASLHTLLGDPCPMLESPGAPCRSAQASVSCALEA
LEPFWEVLVRSTETVERDNMEEDNVEESEEEGPWEPPVLPILTWPVLQSRTGLVYDQNMM
NHCNLWDSHHPEVPQRILRIMCRLEELGLAGRCLTLTPRPATEAELLTCHSAEYVGHLRA
TEKMKTRELHRESSNFDSIYICPSTFACAQLATGAACRLVEAVLSGEVLNGAAVVRPPGH
HAEQDAACGFCFFNSVAVAARHAQTISGHALRILIVDWDVHHGNGTQHMFEDDPSVLYVS
LHRYDHGTFFPMGDEGASSQIGRAAGTGFTVNVAWNGPRMGDADYLAAWHRLVLPIAYEF
NPELVLVSAGFDAARGDPLGGCQVSPEGYAHLTHLLMGLASGRIILILEGGYNLTSISES
MAACTRSLLGDPPPLLTLPRPPLSGALASITETIQVHRRYWRSLRVMKVEDREGPGHHHH
HH

FIGURE 9

SEQ. ID No. 7
MHHHHHHPMEEPEEPADSGQSLVPVYIYSPEYVSMCDSLAKIPKRASMVHSLIEAYALHK
QMRIVKPKVASMEEMAAFHTDAYLQHLQKVSQEGDDDHPDSIEYGLGYDCPATEGIFDYA
AAIGGATITAAQCLIDGMCKVAINWSGGWHHAKKDEASGFCYLNDAVLGILRLRRKFERI
LYVDLDLHHGDGVEDAFSFTSKVMTVSLHKFSPGFFPGTGDVSDVGLGKGRYYSVNVPIQ
DGIQDEKYYQICESVLKEVYQAFNPKAVVLQLGADTIAGDPMCSFNMTPVGIGKCLKYIL
QWQLATLILGGGGYNLANTARCWTYLTGVILGKTLSSEIPDHEFFTAYGPDYVLEITPSC
RPDRNEPHRIQQILNYIKGNLKHVV

FIGURE 8

SEQ. ID No. 6
ATGCCCGGGATGGATCTGAACCTTGAGGCTGAAGCACTGGCTGGCACTGGCTTGGTGTTG
GATGAGCAGTTAAATGAATTCCATTGCCTCTGGGATGACAGCTTCCCGGAAGGCCCTGAG
CGGCTCCATGCCATCAAGGAGCAACTGATCCAGGAGGGCCTCCTAGATCGCTGCGTGTCC
TTTCAGGCCCGGTTTGCTGAAAAGGAAGAGCTGATGTTGGTTCACAGCCTAGAATATATT
GATCTGATGGAAACAACCCAGTACATGAATGAGGGAGAACTCCGTGTCCTAGCAGACACC
TACGACTCAGTTTATCTGCATCCGAACTCATACTCCTGTGCCTGCCTGGCCTCAGGCTCT
GTCCTCAGGCTGGTGGATGCGGTCCTGGGGCTGAGATCCGGAATGGCATGGCCATCATT
AGGCCTCCTGGACATCACGCCCAGCACAGTCTTATGGATGGCTATTGCATGTTCAACCAC
GTGGCTGTGGCAGCCCGCTATGCTCAACAGAAACACCGCATCCGGAGGGTCCTTATCGTA
GATTGGGATGTGCACCACGGTCAAGGAACACAGTTCACCTTCGACCAGGACCCCAGTGTC
CTCTATTTCTCCATCCACCGCTACGAGCAGGGTAGGTTCTGGCCCCACCTGAAGGCCTCT
AACTGGTCCACCACAGGTTTCGGCCAAGGCCAAGGATATACCATCAATGTGCCTTGGAAC
CAGGTGGGGATGCGGGATGCTGACTACATTGCTGCTTTCCTGCACGTCCTGCTGCCAGTC
GCCCTCGAGTTCCAGCCTCAGCTGGTCCTGGTGGCTGCTGGATTTGATGCCCTGCAAGGG
GACCCCAAGGGTGAGATGGCCGCCACTCCGGCAGGGTTCGCCCAGCTAACCCACCTGCTC
ATGGGTCTGGCAGGAGGCAAGCTGATCCTGTCTCTGGAGGGTGGCTACAACCTCCGCGCC
CTGGCTGAAGGCGTCAGTGCTTCGCTCCACACCCTTCTGGGAGACCCTTGCCCCATGCTG
GAGTCACCTGGTGCCCCCTGCCGGAGTGCCCAGGCTTCAGTTTCCTGTGCTCTGGAAGCC
CTTGAGCCCTTCTGGGAGGTTCTTGTGAGATCAACTGAGACCGTGGAGAGGGACAACATG
GAGGAGGACAATGTAGAGGAGAGCGAGGAGGAAGGACCCTGGGAGCCCCTGTGCTCCCA
ATCCTGACATGGCCAGTGCTACAGTCTCGCACAGGGCTGGTCTATGACCAAAATATGATG
AATCACTGCAACTTGTGGGACAGCCACCACCCTGAGGTACCCCAGCGCATCTTGCGGATC
ATGTGCCGTCTGGAGGAGCTGGGCCTTGCCGGGCGCTGCCTCACCCTGACACCGCGCCCT
GCCACAGAGGCTGAGCTGCTCACCTGTCACAGTGCTGAGTACGTGGGTCATCTCCGGGCC
ACAGAGAAAATGAAAACCCGGGAGCTGCACCGTGAGAGTTCCAACTTTGACTCCATCTAT
ATCTGCCCCAGTACCTTCGCCTGTGCACAGCTTGCCACTGGCGCTGCCTGCCGCCTGGTG
GAGGCTGTGCTCTCAGGAGAGGTTCTGAATGGTGCTGCTGTGGTGCGTCCCCAGGACAC
CACGCAGAGCAGGATGCAGCTTGCGGTTTTTGCTTTTTCAACTCTGTGGCTGTGGCTGCT
CGCCATGCCCAGACTATCAGTGGGCATGCCCTACGGATCCTGATTGTGGATTGGGATGTC
CACCACGGTAATGGAACTCAGCACATGTTTGAGGATGACCCCAGTGTGCTATATGTGTCC
CTGCACCGCTATGATCATGGCACCTTCTTCCCCATGGGGGATGAGGGTGCCAGCAGCCAG
ATCGGCCGGGCTGCGGGCACAGGCTTCACCGTCAACGTGGCATGGAACGGGCCCCGCATG
GGTGATGCTGACTACCTAGCTGCCTGGCATCGCCTGGTGCTTCCCATTGCCTACGAGTTT
AACCCAGAACTGGTGCTGGTCTCAGCTGGCTTTGATGCTGCACGGGGGGATCCGCTGGGG
GGCTGCCAGGTGTCACCTGAGGGTTATGCCCACCTCACCCACCTGCTGATGGGCCTTGCC
AGTGGCCGCATTATCCTTATCCTAGAGGGTGGCTATAACCTGACATCCATCTCAGAGTCC
ATGGCTGCCTGCACTCGCTCCCTCCTTGGAGACCCACCACCCCTGCTGACCCTGCCACGG
CCCCCACTATCAGGGGCCCTGGCCTCAATCACTGAGACCATCCAAGTCCATCGCAGATAC
TGGCGCAGCTTACGGGTCATGAAGGTAGAAGACAGAGAAGGACCCGGGCATCACCATCAC
CATCACTAA

FIGURE 10

SEQ. ID No. 8
ATGCACCATCACCATCACCATCCCATGGAGGAGCCGGAGGAACCGGCGGACAGTGGGCAG
TCGCTGGTCCCGGTTTATATCTATAGTCCCGAGTATGTCAGTATGTGTGACTCCCTGGCC
AAGATCCCCAAACGGGCCAGTATGGTGCATTCTTTGATTGAAGCATATGCACTGCATAAG
CAGATGAGGATAGTTAAGCCTAAAGTGGCCTCCATGGAGGAGATGGCCGCCTTCCACACT
GATGCTTATCTGCAGCATCTCCAGAAGGTCAGCCAAGAGGGCGATGATGATCATCCGGAC
TCCATAGAATATGGGCTAGGTTATGACTGCCCAGCCACTGAAGGGATATTTGACTATGCA
GCAGCTATAGGAGGGGCTACGATCACAGCTGCCCAATGCCTGATTGACGGAATGTGCAAA
GTAGCAATTAACTGGTCTGGAGGGTGGCATCATGCAAAGAAAGATGAAGCATCTGGTTTT
TGTTATCTCAATGATGCTGTCCTGGGAATATTACGATTGCGACGGAAATTTGAGCGTATT
CTCTACGTGGATTTGGATCTGCACCATGGAGATGGTGTAGAAGACGCATTCAGTTTCACC
TCCAAAGTCATGACCGTGTCCCTGCACAAATTCTCCCCAGGATTTTTCCCAGGAACAGGT
GACGTGTCTGATGTTGGCCTAGGGAAGGGACGGTACTACAGTGTAAATGTGCCCATTCAG
GATGGCATACAAGATGAAAATATTACCAGATCTGTGAAAGTGTACTAAAGGAAGTATAC
CAAGCCTTTAATCCCAAAGCAGTGGTCTTACAGCTGGGAGCTGACACAATAGCTGGGAT
CCCATGTGCTCCTTTAACATGACTCCAGTGGGAATTGGCAAGTGTCTTAAGTACATCCTT
CAATGGCAGTTGGCAACACTCATTTTGGGAGGAGGAGGCTATAACCTTGCCAACACGGCT
CGATGCTGGACATACTTGACCGGGGTCATCCTAGGGAAAACACTATCCTCTGAGATCCCA
GATCATGAGTTTTTCACAGCATATGGTCCTGATTATGTGCTGGAAATCACGCCAAGCTGC
CGGCCAGACCGCAATGAGCCCCACCGAATCCAACAAATCCTCAACTACATCAAAGGGAAT
CTGAAGCATGTGGTCTAG

HISTONE DEACETYLASE INHIBITORS

RELATED APPLICATION

This application claims the benefit of U.S. Provisional Application No. 60/455,437, filed Mar. 17, 2003 and U.S. Provisional Application No. 60/531,203, filed Dec. 19, 2003, each of which are incorporated herein by reference.

FIELD OF THE INVENTION

The invention relates to compounds that may be used to inhibit deacetylases and, in one variation, histone deacetylases (HDACs), as well as compositions of matter and kits comprising these compounds. The present invention also relates to methods for inhibiting deacetylases, such as HDAC, as well as treatment methods using compounds according to the present invention.

DESCRIPTION OF RELATED ART

DNA in eukaryotic cells is tightly complexed with proteins (histones) to form chromatin. Histones are small, positively charged proteins that are rich in basic amino acids (positively charged at physiological pH), which contact the phosphate groups (negatively charged at physiological pH) of DNA. There are five main classes of histones H1, H2A, H2B, H3, and H4. The amino acid sequences of H2A, H2B, H3, and H4 show remarkable conservation between species, wherein H1 varies somewhat and in some cases is replaced by another histone, e.g., H5. Four pairs of each of H2A, H2B, H3 and H4 together form a disk-shaped octomeric protein core, around which DNA (about 140 base pairs) is wound to form a nucleosome. Individual nucleosomes are connected by short stretches of linker DNA associated with another histone molecule to form a structure resembling a beaded string, which is itself arranged in a helical stack, known as a solenoid.

The majority of histones are synthesized during the S phase of the cell cycle, and newly synthesized histones quickly enter the nucleus to become associated with DNA. Within minutes of its synthesis, new DNA becomes associated with histones in nucleosomal structures.

A small fraction of histones, more specifically, the amino acid side chains thereof, are enzymatically modified by post-translational addition of methyl, acetyl, or phosphate groups, neutralizing the positive charge of the side chain, or converting it to a negative charge. For example, lysine and arginine groups may be methylated, lysine groups may be acetylated, and serine groups may be phosphorylated. For lysine, the $—(CH_2)_4—NH_2$ sidechain may be acetylated, for example by an acetyltransferase enzyme to give the amide $—(CH_2)_4—NHC(=O)CH_3$. Methylation, acetylation, and phosphorylation of amino termini of histones that extend from the nucleosomal core affects chromatin structure and gene expression. Spencer and Davie 1999. Gene 240:1 1-12.

Acetylation and deacetylation of histones is associated with transcriptional events leading to cell proliferation and/or differentiation. Regulation of the function of transcriptional factors is also mediated through acetylation. Recent reviews on histone deacetylation include Kouzarides, et al., 1999. Curr. Opin. Genet. Dev. 9:1, 40-48 and Pazin, et al. 1997. 89:3 325-328.

The correlation between acetylation status of histones and the transcription of genes has been known for quite some time. Certain enzymes, specifically acetylases (e.g., histone acetyltransferases (HAT)) and deacetylases (histone deacetylases or HDACs), which regulate the acetylation state of histones have been identified in many organisms and have been implicated in the regulation of numerous genes, confirming a link between acetylation and transcription. In general, histone acetylation is believed to correlate with transcriptional activation, whereas histone deacetylation is believed to be associated with gene repression.

A growing number of histone deacetylases (HDACs) have been identified. HDACs function as part of large multiprotein complexes, which are tethered to the promoter and repress transcription. Well characterized transcriptional repressors such as MAD, nuclear receptors and YY1 associate with HDAC complexes to exert their repressor function.

Studies of HDAC inhibitors have shown that these enzymes play an important role in cell proliferation and differentiation. HDACs are believed to be associated with a variety of different disease states including, but not limited to cell proliferative diseases and conditions (Marks, P. A., Richon, V. M., Breslow, R. and Rifkind, R. A., J. Natl. Cancer Inst. (Bethesda) 92, 1210-1215, 2000) such as leukemia (Lin et al. 1998. Nature 391: 811-814; Grignani, et al. 1998. Nature 391: 815-818; Warrell et al. 1998. J. Natl. Cancer Inst. 90:1621-1625; Gelmetti et al. 1998. Mol. Cell Biol. 18:7185-7191; Wang et al. 1998. PNAS 951 0860-10865), melanomas/squamous cell carcinomas (Gillenwater, et al., 1998, Int. J. Cancer 75217-224; Saunders, et al., 1999, Cancer Res. 59:399-404), breast cancer, prostrate cancer, bladder cancer (Gelmetti et al. 1998. Mol. Cell Biol. 18:7185-7191; Wang et al. 1998. PNAS 951 0860-10865), lung cancer, ovarian cancer and colon cancer (Hassig, et al., 1997, Chem. Biol. 4:783-789; Archer, et al., 1998, PNAS, 956791-6796; Swendeman, et al., 1999, Proc. Amer. Assoc. Cancer Res. 40, Abstract #3836).

Histone deacetylase inhibitors are potent inducers of growth arrest, differentiation, or apoptotic cell death in a variety of transformed cells in culture and in tumor bearing animals (*Histone deacetylase inhibitors as new cancer drugs*, Marks, P. A., Richon, V. M., Breslow, R. and Rifkind, R. A., Current Opinions in Oncology, 2001, Nov. 13 (6): 477-83; *Histone deacetylases and cancer: causes and therapies*, Marks, P., Rifkind, R. A., Richon, V. M., Breslow, R., Miller, T. and Kelly, W. K., Nat. Rev. Cancer 2001 Dec. 1(3):194-202). In addition, HDAC inhibitors are useful in the treatment or prevention of protozoal diseases (U.S. Pat. No. 5,922,837) and psoriasis (PCT Publication No. WO 02/26696).

A variety of inhibitors of HDAC have been reported. Some of these inhibitors are described in the following table:

| Inhibitors | References |
|---|---|
| Butyrates | Marks PA, et al., J. Natl. Cancer Inst. 2000, 92:1210–1216; Weidle UH, et al., Anticancer Res. 2000, 20:1471–1486; Gore SD, et al., Exp. Opin. Invest. Drugs 2000, 9:2923–2934; Sowa Y, et al., Biofactors 2000, 12:283–287. |
| Trichostatin A | Marks PA, et al., J. Natl. Cancer Inst. 2000, 92:1210–1216; Weidle UH, et al., Anticancer Res. 2000, 20:1471–1486; Nervi C, et al., Cancer Res. 2001, 61:1247–1249; Suzuki T, et al., Int. J. Cancer 2000, 88:992–997. |
| Suberoylanilidine hydroxaniic acid | Marks PA, et al., J. Natl. Cancer Inst. 2000, 92:1210–1216; Kelly WK, et al., Proc. Amer. Soc. Clin. Oncol. 2001, 20:87a; Butler LM, et al., Cancer Res. 2000, 60:5165–5170. |
| MS-275 | Lee BI, et al., Cancer Res. 2001, 61:931–934. |

Additional examples of HDAC inhibitors can be found in Marks P A, et al., J. Natl. Cancer Inst. 2000, 92:1210-1216 & Weidle U H, et al., Anticancer Res. 2000, 20:1471-1486 and PCT Publication Nos. WO 02/26696, WO 02/062773, and WO 01/18171.

Despite the various HDAC inhibitors that have been reported to date, a need continues to exist for new and more effective inhibitors of HDACs.

SUMMARY OF THE INVENTION

The present invention relates to compounds that have activity for inhibiting HDACs.

The present invention also provides compositions, articles of manufacture and kits comprising these compounds.

In one embodiment, a pharmaceutical composition is provided that comprises a HDAC inhibitor according to the present invention as an active ingredient. Pharmaceutical compositions according to the invention may optionally comprise 0.001%-100% of one or more HDAC inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with HDAC.

In one embodiment, a kit is provided that comprises a composition comprising at least one HDAC inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one HDAC inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit HDAC.

In one embodiment, the compounds, compositions, kits and articles of manufacture are used to treat a disease state for which HDAC possesses activity that contributes to the pathology and/or symptomology of the disease state.

In another embodiment, a compound is administered to a subject wherein HDAC activity within the subject is altered, preferably reduced.

In another embodiment, a prodrug of a compound is administered to a subject that is converted to the compound in vivo where it inhibits HDAC.

In another embodiment, a method of inhibiting HDAC is provided that comprises contacting HDAC with a compound according to the present invention.

In another embodiment, a method of inhibiting HDAC is provided that comprises causing a compound according to the present invention to be present in a subject in order to inhibit HDAC in vivo.

In another embodiment, a method of inhibiting HDAC is provided that comprises administering a first compound to a subject that is converted in vivo to a second compound wherein the second compound inhibits HDAC in vivo.

In another embodiment, a therapeutic method is provided that comprises administering a compound according to the present invention.

In another embodiment, a method of inhibiting cell proliferation is provided that comprises contacting a cell with an effective amount of a compound according to the present invention.

In another embodiment, a method of inhibiting cell proliferation in a patient is provided that comprises administering to the patient a therapeutically effective amount of a compound according to the present invention.

In another embodiment, a method of treating a condition in a patient which is known to be mediated by HDAC, or which is known to be treated by HDAC inhibitors, comprising administering to the patient a therapeutically effective amount of a compound according to the present invention.

In another embodiment, a method is provided for using a compound according to the present invention in order to manufacture a medicament for use in the treatment of disease state which is known to be mediated by HDAC, or which is known to be treated by HDAC inhibitors.

In another embodiment, a method is provided for treating a disease state for which HDAC possesses activity that contributes to the pathology and/or symptomology of the disease state, the method comprising: causing a compound according to the present invention to be present in a subject in a therapeutically effective amount for the disease state.

In another embodiment, a method is provided for treating a disease state for which HDAC possesses activity that contributes to the pathology and/or symptomology of the disease state, the method comprising: administering a first compound to a subject that is converted in vivo to a second compound such that the second compound is present in the subject in a therapeutically effective amount for the disease state.

In another embodiment, a method is provided for treating a disease state for which HDAC possesses activity that contributes to the pathology and/or symptomology of the disease state, the method comprising: administering a compound according to the present invention to a subject such that the compound is present in the subject in a therapeutically effective amount for the disease state.

In another embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of diseases that may be treated by administration of compounds and compositions according to the present invention include, but are not limited to protozoal diseases and cell proliferative diseases and conditions such as leukemia, melanomas, squamous cell carcinomas, breast cancer, prostrate cancer, bladder cancer, lung cancer including non small-cell lung cancer and small-cell lung cancer, ovarian cancer, colon cancer, squamous cell carcinoma, astrocytoma, Kaposi's sarcoma, glioblastoma, bladder cancer, head and neck cancer, glioma, colorectal cancer, genitourinary cancer and gastrointestinal cancer.

It is noted in regard to all of the above embodiments that the present invention is intended to encompass pharmaceutically acceptable salts, biohydrolyzable esters, biohydrolyzable amides, biohydrolyzable carbamates, and solvates (e.g., hydrates) of the compounds, regardless of whether such salts, esters, amides, carbamates and solvates are specified since it is well know in the art to administer pharmaceutical agents in a salt, ester, amide, carbamate or solvated form. It is further noted that prodrugs may also be administered which are altered in vivo and become a compound according to the present invention. For example, the compound optionally comprises a substituent that is convertible in vivo to a different substituent, such as hydrogen. Accordingly, for example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide that is converted by hydrolysis in vivo to the amine compound.

The various methods of using the compounds of the present invention are intended, regardless of whether prodrug delivery is specified, to encompass the administration of a prodrug that is converted in vivo into a compound according to the present invention.

Figure 1:
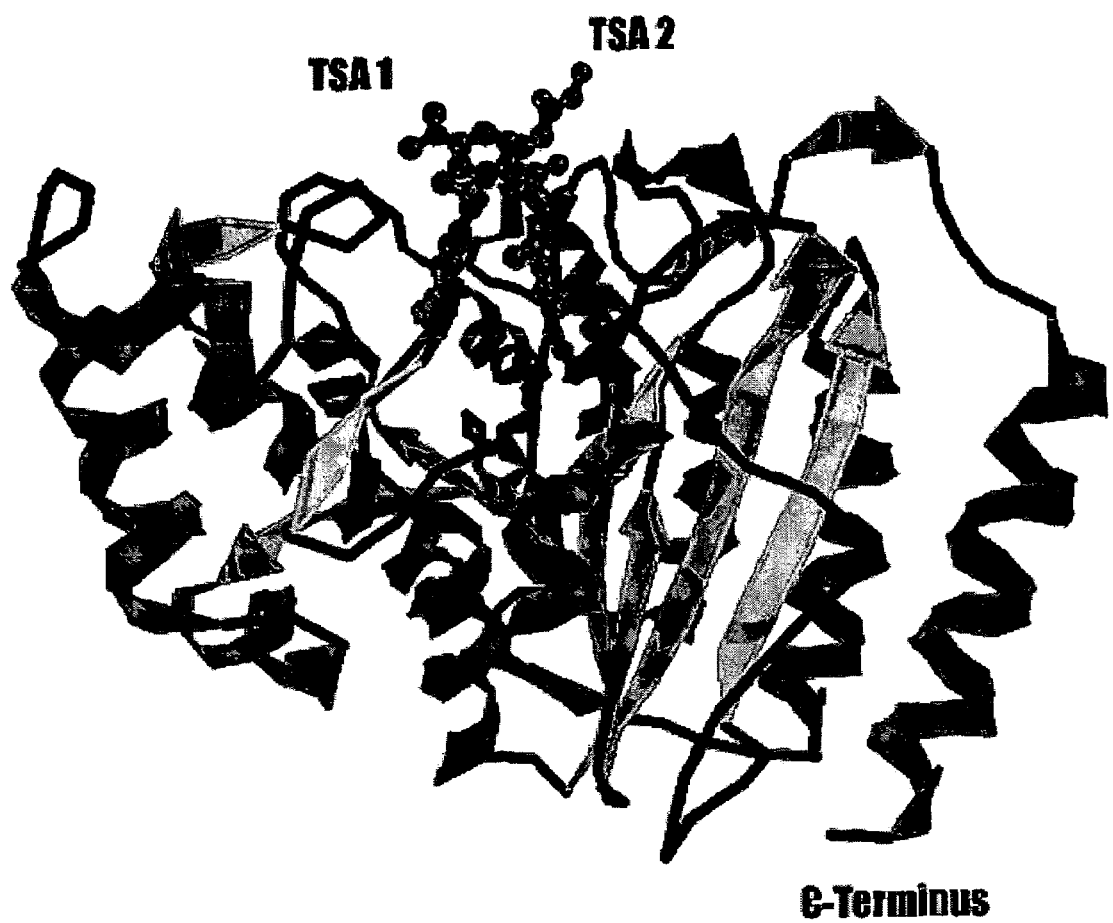
FIG. 1 illustrates a ribbon diagram overview of the structure of HDAC8, highlighting the secondary structural elements of the protein.

It is noted in regard to FIGS. 2A-2D that the squiggle line is intended to indicate a bond to an adjacent moiety. It is also noted that the substituents shown may optionally be further substituted beyond what is shown. Further, one or more heteroatoms may optionally be substituted for the carbon atoms shown. In regard to FIG. 2D, it is noted that the leader groups moieties may be incorporated into the leader group in either possible orientation.

FIG. 3 illustrates residues 1-482 of HDAC1 and a 6-histidine tag at the N-terminus (SEQ. I.D. No. 1).

FIG. 4 illustrates the DNA sequence (SEQ. I.D. No. 2) that was used to encode SEQ. I.D. No. 1.

FIG. 5 illustrates residues 1-488 of HDAC2 and a 6-histidine tag at the C-terminus (SEQ. I.D. No. 3).

FIG. 6 illustrates the DNA sequence (SEQ. I.D. No. 4) that was used to encode SEQ. I.D. No. 3.

FIG. 7 illustrates residues 73-845 of HDAC6 and a 6-histidine tag at the C-terminus (SEQ. I.D. No. 5).

FIG. 8 illustrates the DNA sequence (SEQ. I.D. No. 6) that was used to encode SEQ. I.D. No. 5.

FIG. 9 illustrates residues 1-377 of HDAC8 and a 6-histidine tag at the N-terminus (SEQ. I.D. No. 7).

FIG. 10 illustrates the DNA sequence (SEQ. I.D. No. 8) that was used to encode SEQ. I.D. No. 7.

DEFINITIONS

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one or more double or triple bonds. Alicyclic moieties may also optionally comprise heteroatoms such as nitrogen, oxygen and sulfur. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one or more double or triple bonds.

"Alkenyl" represented by itself means a straight or branched, unsaturated, aliphatic radical having a chain of carbon atoms having at least one double bond between adjacent carbon atoms. $C_X$ alkenyl and $C_{X-Y}$ alkenyl are typically used where X and Y indicate the number of carbon atoms in the chain. For example, $C_{2-6}$ alkenyl includes alkenyls that have a chain of between 2 and 6 carbons.

"Alkoxy" means an oxygen moiety having a further alkyl substituent.

"Alkyl" represented by itself means a straight or branched, saturated or unsaturated, aliphatic radical having a chain of carbon atoms, optionally with oxygen (See "oxaalkyl") or nitrogen atoms (See "aminoalkyl") between the carbon atoms. $C_X$ alkyl and $C_{X-Y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-10})$aryl$(C_{0-3})$alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical. $C_X$ alkylene and $C_{X-Y}$ alkylene are typically used where X and Y indicate the number of carbon atoms in the chain. For example, $C_{1-6}$ alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-butenylene (—CH$_2$CH═CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like).

"Alkylidene" means a straight or branched unsaturated, aliphatic, divalent radical having a general formula ═CR$_a$R$_b$. $C_X$ alkylidene and $C_{X-Y}$ alkylidene are typically used where X and Y indicate the number of carbon atoms in the chain. For example, $C_{1-6}$ alkylidene includes methylidene (═CH$_2$), ethylidene (═CHCH$_3$), isopropylidene (═C(CH$_3$)$_2$), propylidene (═CHCH$_2$CH$_3$), allylidene (═CH—CH═CH$_2$), and the like).

"Alkynyl" represented by itself means a straight or branched, unsaturated, aliphatic radical having a chain of carbon atoms having at least one triple bond between adjacent carbon atoms. $C_X$ alkynyl and $C_{X-Y}$ alkynyl are typically used where X and Y indicate the number of carbon atoms in the chain. For example, $C_{2-6}$ alkynyl includes alkynyls that have a chain of between 2 and 6 carbons.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aminoalkyl" means an alkyl, as defined above, except where one or more substituted or unsubstituted nitrogen atoms (—N—) are positioned between carbon atoms of the alkyl. For example, an $(C_{2-6})$ aminoalkyl refers to a chain comprising between 2 and 6 carbons and one or more nitrogen atoms positioned between the carbon atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or fused bicyclic ring assembly wherein each ring is aromatic or when fused with a second ring forms an aromatic ring assembly. If one or more ring atoms is not carbon (e.g., N, S), the aryl is a heteroaryl. $C_X$ aryl and $C_{X-Y}$ aryl are typically used where X and Y indicate the number of atoms in the ring.

"Bicycloalkyl" means a saturated or partially unsaturated fused bicyclic or bridged polycyclic ring assembly.

"Bicycloaryl" means a bicyclic ring assembly wherein the rings are linked by a single bond or fused and at least one of the rings comprising the assembly is aromatic. $C_X$ bicycloaryl and $C_{X-Y}$ bicycloaryl are typically used where X and Y indicate the number of carbon atoms in the bicyclic ring assembly and directly attached to the ring.

"Carbamoyl" means the radical —OC(O)NR$_a$R$_b$, where R$_a$ and R$_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbocycle" means a ring consisting of carbon atoms.

"Carbocyclic ketone derivative" means a carbocyclic derivative having a —C(O)— substituent.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, fused bicyclic or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent saturated or partially unsaturated, monocyclic ring or bridged polycyclic ring assembly. $C_X$ cycloalkylene and $C_{X-Y}$ cycloalkylene are typically used where X and Y indicate the number of carbon atoms in the ring assembly.

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted ($C_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to nitrogen, oxygen, sulfur and halogens.

"Heteroatom moiety" includes a moiety where the atom by which the moiety is attached is not a carbon. Examples of heteroatom moieties include —N=, —NR$_c$—, —N$^+$(O$^-$)=, —O—, —S— or —S(O)$_2$—, wherein R$_c$ is further substituent.

"Heterobicycloalkyl" means bicycloalkyl, as defined in this Application, provided that one or more of the atoms forming the ring is a heteroatom. For example hetero($C_{9-12}$)bicycloalkyl as used to define Z in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like.

"Heterocycloalkylene" means cycloalkylene, as defined in this Application, provided that one or more of the ring member carbon atoms indicated, is replaced by a heteroatom.

"Heteroaryl" means an aryl ring, as defined in this Application, where one or more of the atoms forming the ring is a heteroatom.

"Heterobicycloaryl" means bicycloaryl, as defined in this Application, provided that one or more of the atoms forming the ring is a heteroatom. For example, hetero($C_{8-10}$)bicycloaryl as used in this Application includes, but is not limited to, 2-amino-4-oxo-3,4-dihydropteridin-6-yl, and the like.

"Heterocycloalkyl" means cycloalkyl, as defined in this Application, provided that one or more of the atoms forming the ring is a heteroatom.

"Hydroxy" means the radical —OH.

"Imine derivative" means a derivative comprising the moiety —C(NR)—, wherein R comprises a hydrogen or carbon atom alpha to the nitrogen.

"Isomers" mean any compound having an identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Nitro" means the radical —NO$_2$.

"Oxaalkyl" means an alkyl, as defined above, except where one or more oxygen atoms (—O—) are positioned between carbon atoms of the alkyl. For example, an ($C_{2-6}$) oxaalkyl refers to a chain comprising between 2 and 6 carbons and one or more oxygen atoms positioned between the carbon atoms.

"Oxoalkyl" means an alkyl, further substituted with a carbonyl group. The carbonyl group may be an aldehyde, ketone, ester, amide, acid or acid chloride.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of inhibitors of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have HDAC inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates and quinates.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, alkyl, alkylene, alkylidene, amide, amino, aminoalkyl, aromatic, aryl, bicycloalkyl, bicycloaryl, carbamoyl, carbocycle, carboxy, carbonyl group, cycloalkyl, cycloalkylene, ester, halo, heterobicycloalkyl, heterocycloalkylene, heteroaryl, heterobicycloaryl, heterocycloalkyl, hydroxy, iminoketone, ketone, nitro, oxaalkyl, and oxoalkyl moieties, each of which may optionally also be substituted or unsubstituted.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the disease (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$CR_aR_bR_c$ where $R_a$, $R_b$, and $R_c$ may each independently be hydrogen or any other substituent where the atom alpha to the carbon is a heteroatom or cyano. Hence, $CF_3$, $CH_2OH$ and $CH_2CN$ are all $C_1$ alkyls.

DETAILED DESCRIPTION OF THE INVENTION

The present invention relates to compounds, compositions, kits and articles of manufacture that may be used to inhibit histone deacetylases (referred to herein as HDACs). The compounds may optionally be more particularly used as inhibitors of Class I HDACs such as HDAC1, HDAC2, HDAC6 and HDAC8.

At least seventeen human genes that encode proven or putative HDACs have been identified to date, some of which are described in Johnstone, R. W., "Histone-Deacetylase Inhibitors: Novel Drugs for the Treatment of Cancer", Nature Reviews, Volume I, pp. 287-299, (2002) and PCT Publication Nos. 00/10583, 01/18045, 01/42437 and 02/08273.

HDACs have been categorized into three distinct classes based on their relative size and sequence homology. The different HDACs (*Homo sapiens*), HDAC classes, sequences and references describing the different HDACs are provided in Tables 1-3.

TABLE 1

CLASS I HDACs

| HDAC | GenBank Accession Number | Reference |
|---|---|---|
| 1 | NP_004955 | Histone deacetylase: a regulator of transcription, Wolffe, A. P., Science 272 (5260), 371–372 (1996) |
| 2 | NP_001518 | Isolation and mapping of a human gene (RPD3L1) that is homologous to RPD3, a transcription factor in Saccharomyces cerevisiae; Furukawa, Y., Kawakami, T., Sudo, K., Inazawa, J., Matsumine, A., Akiyama, T. and Nakamura, Y., Cytogenet. Cell Genet. 73 (1–2), 130–133 (1996) |
| 3 | NP_003874 | Isolation and characterization of cDNAs corresponding to an additional member of the human histone deacetylase gene family, Yang, W. M., Yao, Y. L., Sun, J. M., Davie, J. R. and Seto, E., J. Biol. Chem. 272 (44), 28001–28007 (1997) |
| 8 | NP_060956 | Buggy, J. J., Sideris, M. L., Mak, P., Lorimer, D. D., McIntosh, B. and Clark, J. M. Biochem. J. 350 Pt 1, 199–205 (2000) |
| 11 | NP_079103 | Cloning and Functional Characterization of HDAC11, a Novel Member of the Human Histone Deacetylase Family, Gao, L., Cueto, M. A., Asselbergs, F. and Atadja, P., J. Biol. Chem. 277 (28), 25748–25755 (2002) |

TABLE 2

CLASS II HDACs

| HDAC | GenBank Accession Number | Reference |
|---|---|---|
| 4 | NP_006028 | Transcriptional control. Sinful repression, Wolffe, A. P., Nature 387 (6628), 16–17 (1997) |
| 5 | NP_631944 | Prediction of the coding sequences of unidentified human genes. IX. The complete sequences of 100 new cDNA clones from brain which can code for large proteins in vitro, Nagase, T., Ishikawa, K., Miyajima, N., Tanaka, A., Kotani, H., Nomura, N. and Ohara, O., DNA Res. 5 (1), 31–39 (1998) |
| 6 | NP_006035 | Transcriptional control. Sinful repression, Wolffe, A. P., Nature 387 (6628), 16–17 (1997) |
| 7 | NP_057680 | Isolation of a novel histone deacetylase reveals that class I and class II deacetylases promote SMRT-mediated repression, Kao, H. Y., Downes, M., Ordentlich, P. and Evans, R. M., Genes Dev. 14 (1), 55–66 (2000) |
| 9 | NP_478056 | MEF-2 function is modified by a novel co-repressor, MITR, Sparrow, D. B., Miska, E. A., Langley, E., Reynaud-Deonauth, S., Kotecha, S., Towers, N., Spohr, G., Kouzarides, T. and Mohun, T. J., EMBO J. 18 (18), 5085–5098 (1999) |
| 10 | NP_114408 | Isolation and characterization of mammalian HDAC10, a novel histone deacetylase, Kao, H. Y., Lee, C. H., Komarov, A., Han, C. C. and Evans, R. M., J. Biol. Chem. 277 (1), 187–193 (2002) |

TABLE 3

CLASS III HDACs

| HDAC | GenBank Accession Number | Reference |
|---|---|---|
| Sirtuin 1 | NP_036370 | Characterization of five human cDNAs with homology to the yeast SIR2 gene: Sir2-like proteins (sirtuins) metabolize NAD and may have protein ADP-ribosyltransferase activity; Frye, R. A.; Biochem. Biophys. Res. Commun. 260 (1), 273–279 (1999) |
| Sirtuin 2 | NP_085096/ NP_036369 | A 'double adaptor' method for improved shotgun library construction; Andersson, B., Wentland, M. A., Ricafrente, J. Y., Liu, W. and Gibbs, R. A.; Anal. Biochem. 236 (1), 107–113 (1996) |

TABLE 3-continued

CLASS III HDACs

| HDAC | GenBank Accession Number | Reference |
|---|---|---|
| Sirtuin 3 | NP_036371 | Characterization of five human cDNAs with homology to the yeast SIR2 gene: Sir2-like proteins (sirtuins) metabolize NAD and may have protein ADP-ribosyltransferase activity; Frye, R. A.; Biochem. Biophys. Res. Commun. 260 (1), 273–279 (1999) |
| Sirtuin 4 | NP_036372 | Characterization of five human cDNAs with homology to the yeast SIR2 gene: Sir2-like proteins (sirtuins) metabolize NAD and may have protein ADP-ribosyltransferase activity; Frye, R. A.; Biochem. Biophys. Res. Commun. 260 (1), 273–279 (1999) |
| Sirtuin 5 | NP_112534/ NP_036373 | Characterization of five human cDNAs with homology to the yeast SIR2 gene: Sir2-like proteins (sirtuins) metabolize NAD and may have protein ADP-ribosyltransferase activity; Frye, R. A.; Biochem. Biophys. Res. Commun. 260 (1), 273–279 (1999) |
| Sirtuin 6 | NP_057623 | Phylogenetic classification of prokaryotic and eukaryotic Sir2-like proteins; Frye, R. A.; Biochem. Biophys. Res. Commun. 273 (2), 793–798 (2000) |
| Sirtuin 7 | NP_057622 | Phylogenetic classification of prokaryotic and eukaryotic Sir2-like proteins; Frye, R. A.; Biochem. Biophys. Res. Commun. 273 (2), 793–798 (2000) |

Of particular note are Class I HDACs. All Class I HDACs appear to be sensitive to inhibition by trichostatin A (TSA). Also of particular note is HDAC8, a protein whose crystal structure Applicants determined and used in conjunction with arriving at the present invention.

HDAC8 is a 377 residue, 42 kDa protein localized to the nucleus of a wide array of tissues, as well as several human tumor cell lines. The wild-type form of full length HDAC8 is described in GenBank Accession Number NP 060956; Buggy, J. J., Sideris, M. L., Mak, P., Lorimer, D. D., McIntosh, B. and Clark, J. M., Cloning and characterization of a novel human histone deacetylase, HDAC8, Biochem. J. 350 Pt 1, 199-205 (2000). $Zn^{2+}$ is likely native to the protein and required for HDAC8 activity.

1. Crystal Structure for HDAC

Syrrx, Inc. in San Diego, Calif. recently solved the crystal structure for HDAC8. Knowledge of the crystal structure was used to guide the design of the HDAC inhibitors provided herein.

FIG. 1 illustrates a ribbon diagram overview of the structure of HDAC8, highlighting the secondary structural elements of the protein. HDAC8 was found to have a single domain structure belonging to the open α/β class of folds. The structure consists of a central 8-stranded parallel β-sheet sandwiched between layers of α-helices. The ligand binding clefts lie almost in the plane of the central β-sheet, and are formed primarily by loops emanating from the carboxy-terminal ends of the β-strands comprising the sheet. There are two large structural extensions, which occur beyond the core of the α/β motif, off the second and last β-strands of the central β-sheet. Residues contained in the extension off the second β-strand form a globular "cap" over the core of the protein, play an important role in defining the shape of the ligand binding pockets, and are involved in a number of key interactions with the bound ligands.

2. HDAC Inhibitors

In one embodiment, HDAC inhibitors of the present invention are provided that comprise the formula

Z-Q-L-M wherein

Z is selected from the group consisting of

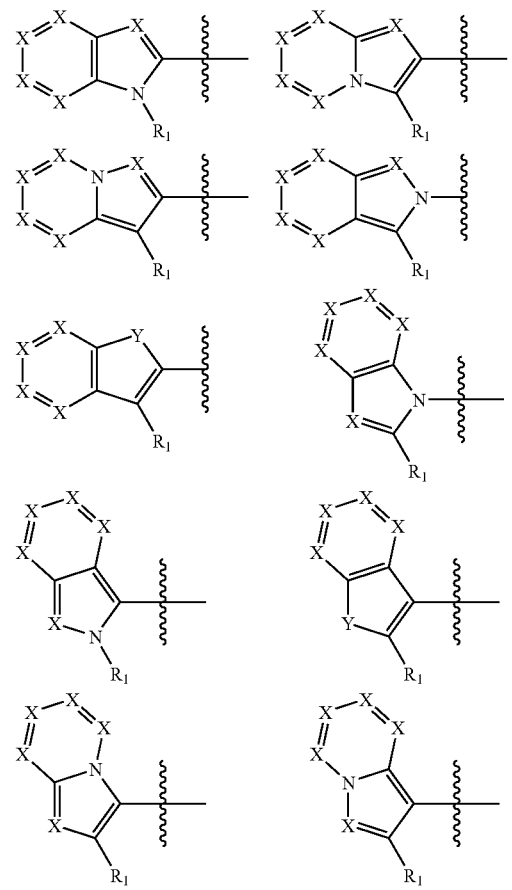

wherein each X is independently selected from the group consisting of $CR_{12}$ and N;

each Y is independently selected from the group consisting of O, S and $NR_{12}$;

$R_1$ is selected from the group consisting of hydrogen, halo, alkyl, cycloalkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_1$ is not halo, cyano, nitro and thio in the case where the ring atom to which $R_1$ is bound is nitrogen, and each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

Q is a substituted or unsubstituted aromatic ring;

M is a substituent capable of complexing with a deacetylase catalytic site and/or a metal ion; and L is a substituent providing between 0-10 atoms separation between the M substituent and the Q substituent.

In another embodiment, HDAC inhibitors of the present invention are provided that comprise the formula

Z-Q-L-M wherein

Z is selected from the group consisting of

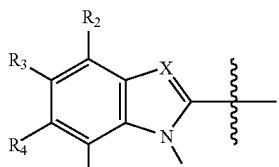

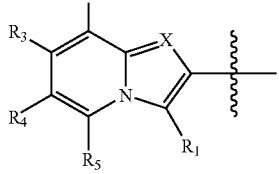

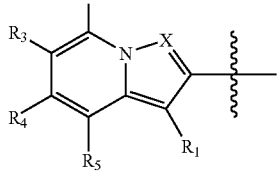

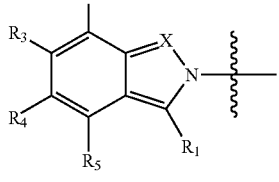

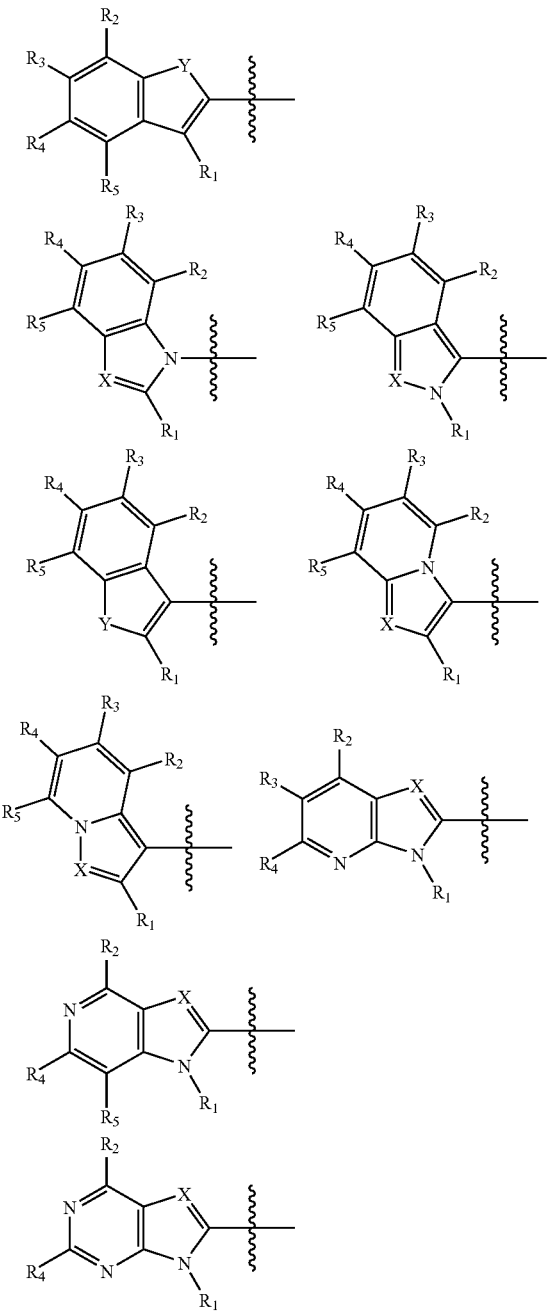

wherein
each X is independently selected from the group consisting of $CR_{12}$ and N;
each Y is independently selected from the group consisting of O, S and $NR_{12}$;
$R_1$ is selected from the group consisting of hydrogen, halo, alkyl, cycloalkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_1$ is not halo, cyano, nitro and thio in the case where the ring atom to which $R_1$ is bound is nitrogen;

$R_2$, $R_3$, $R_4$ and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted; and each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

Q is a substituted or unsubstituted aromatic ring;

M is a substituent capable of complexing with a deacetylase catalytic site and/or a metal ion; and L is a substituent providing between 0-10 atoms separation between the M substituent and the Q substituent.

In another embodiment, HDAC inhibitors of the present invention are provided that comprise the formula:

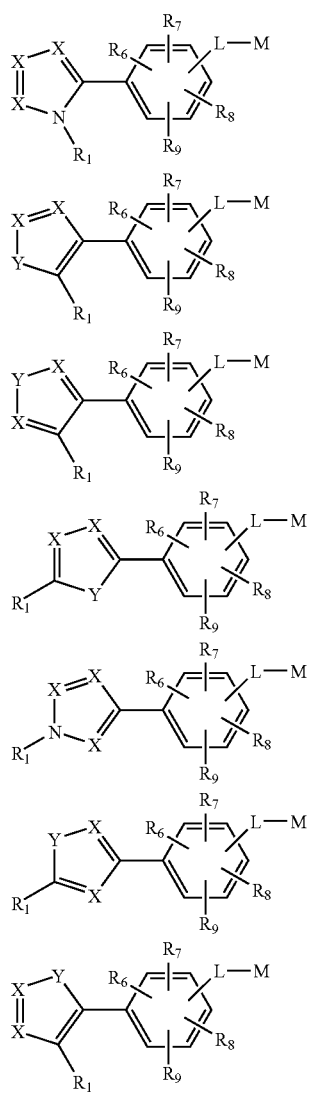

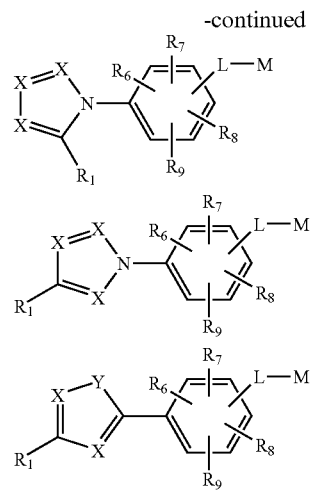

wherein
each X is independently selected from the group consisting of $CR_{12}$ and N;

each Y is independently selected from the group consisting of O, S and $NR_{12}$;

$R_1$ is selected from the group consisting of hydrogen, halo, alkyl, cycloalkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_1$ is not halo, cyano, nitro and thio in the case where the ring atom to which $R_1$ is bound is nitrogen;

$R_6$, $R_7$, $R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;

each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

M is a substituent capable of complexing with a deacetylase catalytic site and/or a metal ion; and L is a substituent providing between 0-10 atoms separation between the M substituent and the remainder of the compound.

In another embodiment, HDAC inhibitors of the present invention are provided that comprise the formula:

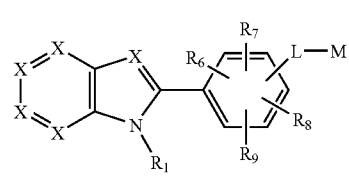

-continued

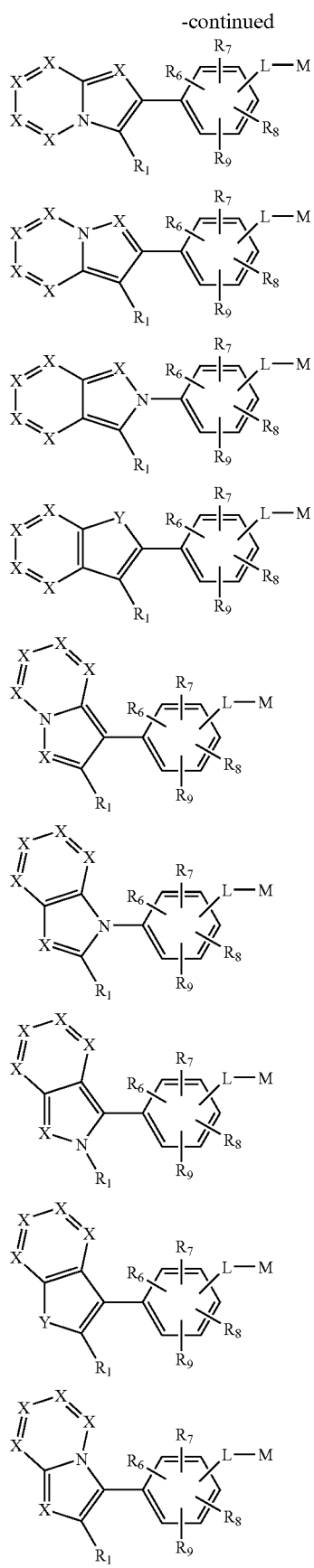

wherein
each X is independently selected from the group consisting of $CR_{12}$ and N;
each Y is independently selected from the group consisting of O, S and $NR_{12}$;
$R_1$ is selected from the group consisting of hydrogen, halo, alkyl, cycloalkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_1$ is not halo, cyano, nitro and thio in the case where the ring atom to which $R_1$ is bound is nitrogen;
$R_6$, $R_7$, $R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
M is a substituent capable of complexing with a deacetylase catalytic site and/or a metal ion; and
L is a substituent providing between 0-10 atoms separation between the M substituent and the remainder of the compound.

In another embodiment, HDAC inhibitors of the present invention are provided that comprise the formula:

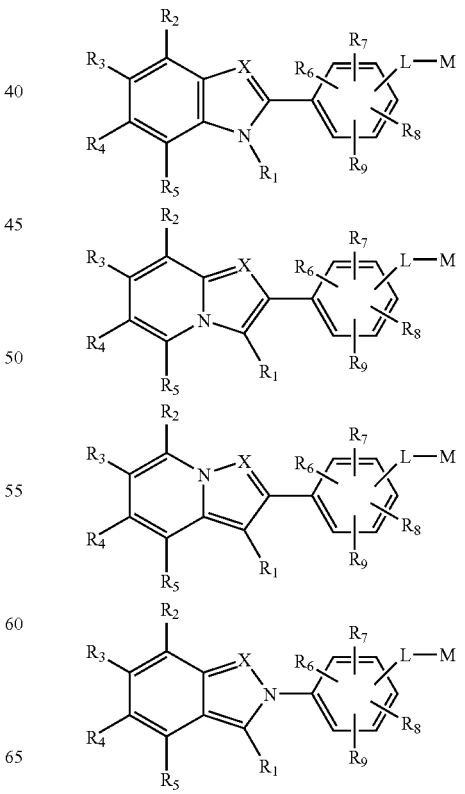

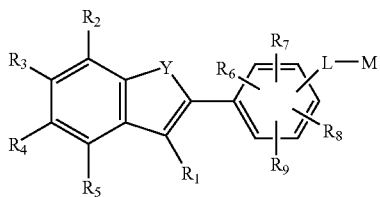
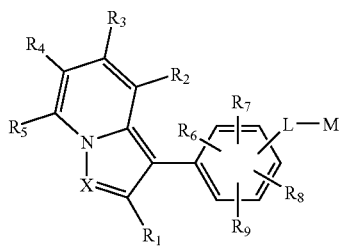
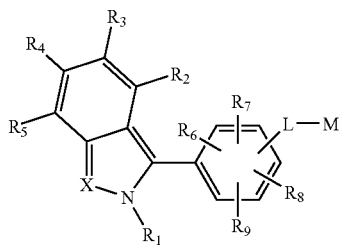
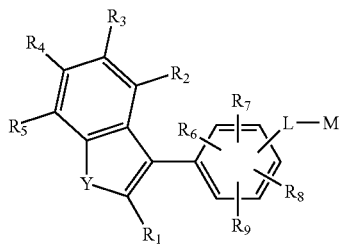
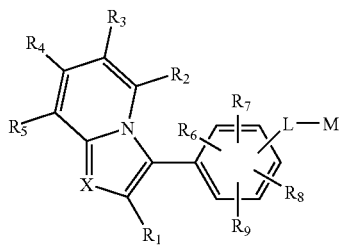
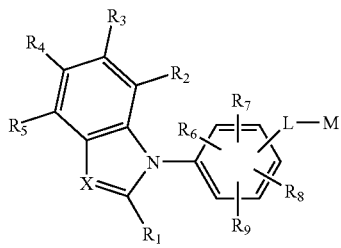
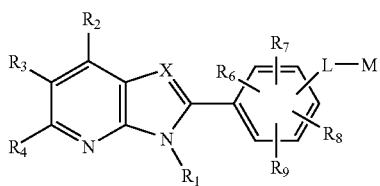

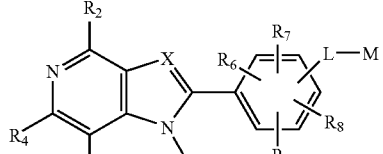
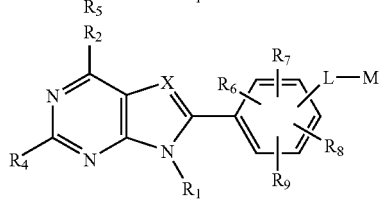

wherein
  each X is independently selected from the group consisting of $CR_{12}$ and N;
  each Y is independently selected from the group consisting of O, S and $NR_{12}$;
  $R_1$ is selected from the group consisting of hydrogen, halo, alkyl, cycloalkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_1$ is not halo, cyano, nitro and thio in the case where the ring atom to which $R_1$ is bound is nitrogen;
  $R_2$, $R_3$, $R_4$, $R_5$, $R_6$, $R_7$, $R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
  each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
  M is a substituent capable of complexing with a deacetylase catalytic site and/or a metal ion; and
  L is a substituent providing between 0-10 atoms separation between the M substituent and the Q substituent.

In another embodiment, HDAC inhibitors of the present invention are provided that comprise the formula:

Z-Q-L-M wherein
  Z is selected from the group consisting of

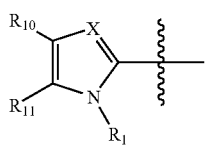 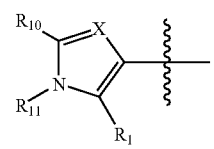

-continued

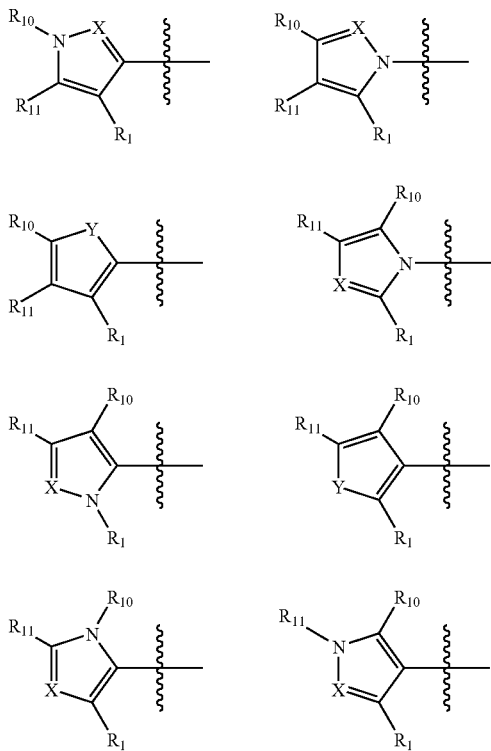

wherein
- each X is independently selected from the group consisting of $CR_{12}$ and N;
- each Y is independently selected from the group consisting of O, S and $NR_{12}$;
- $R_1$ is selected from the group consisting of hydrogen, halo, alkyl, cycloalkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_1$ is not halo, cyano, nitro and thio in the case where the ring atom to which $R_1$ is bound is nitrogen;
- $R_{10}$ and $R_{11}$ are taken together to form a substituted or unsubstituted aromatic ring;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
- Q is a substituted or unsubstituted aromatic ring;
- M is a substituent capable of complexing with a deacetylase catalytic site and/or a metal ion; and
- L is a substituent providing between 0-10 atoms separation between the M substituent and the Q substituent.

In another embodiment, HDAC inhibitors of the present invention are provided that comprise the formula:

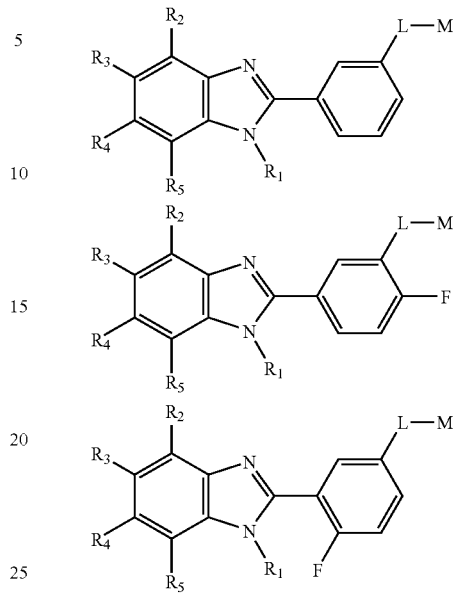

wherein
- $R_1$ is selected from the group consisting of hydrogen, halo, alkyl, cycloalkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_1$ is not halo, cyano, nitro and thio in the case where the ring atom to which $R_1$ is bound is nitrogen;
- $R_2$, $R_3$, $R_4$, and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
- M is a substituent capable of complexing with a deacetylase catalytic site and/or a metal ion; and
- L is a substituent providing between 0-10 atoms separation between M and the remainder of the compound.

In another embodiment, HDAC inhibitors of the present invention are provided that comprise the formula:

Z-Q-L-M wherein
Z-Q- is selected from the group consisting of

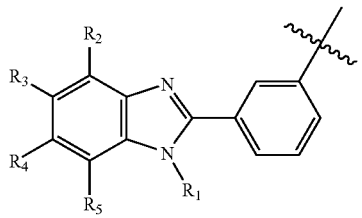

-continued

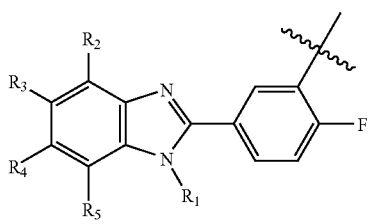

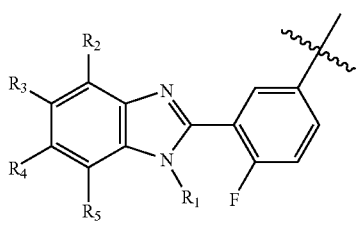

R₁ is selected from the group consisting of hydrogen, alkyl, cycloalkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;

R₂, R₃, R₄, and R₅ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;

M is a substituent capable of complexing with a deacetylase catalytic site and/or a metal ion; and L is a substituent providing between 0-10 atoms separation between M and the remainder of the compound.

In another embodiment, HDAC inhibitors of the present invention are provided that comprise the formula:

Z-Q-L-M wherein

Z-Q- is selected from the group consisting of

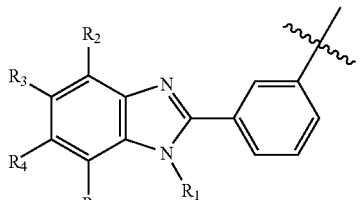

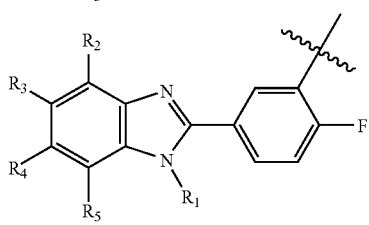

-continued

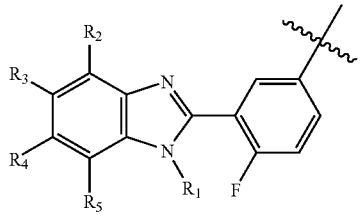

R₁ is selected from the group consisting of (C₁₋₄)alkyl, phenyl, 1-piperidin-4-ylmethyl, 2-morpholi-4-yl-ethyl, 2-halo-phenyl, 2-halo-phen(C₁₋₄)alkyl, 3-halo-phen(C₁₋₄)alkyl, 2-CF₃O-phen(C₁₋₄)alkyl, 3-CF₃O-phen(C₁₋₄)alkyl, 3-halo-phenyl, 4-halo-phenyl, 2-methoxy-phenyl, 3-methoxy-phenyl, 4-methoxy-phenyl, 4-phenoxy-phenyl, 4-benzyloxyphenyl, 4-pyrazol-1-yl-benzyl, 1-p-tolyl-ethyl, pyrrolidin-3-yl, 1-(C₁₋₁₄)alkyl-pyrrolidin-2-yl, 1-(C₁₋₄)alkyl-pyrrolidin-2-yl; 2-di(C₁₋₄)alkylamino-ethyl, 2-di(C₁₋₄)alkylamino-1-methyl-ethyl, 2-di(C₁₋₄)alkylamino-ethyl, 2-hydroxy-2-phenyl-ethyl, 2-pyridin-2-yl-ethyl, 2-pyridin-3-yl-ethyl, 2-pyridin-4-yl-ethyl, 2-(1H-indol-3-yl)-ethyl, 3-indolyl(C₁₋₄)alkyl, 1-indan-2-yl, R-α-(HOCH₂)-phen(C₁₋₄)alkyl, S-α-(HOCH₂)-phen(C₁₋₄)alkyl, S-β-(HOCH₂)-phen(C₁₋₄)alkyl, R-β-(CH₃)-phen(C₁₋₄)alkyl, 6-propylsulfanyl, trans-4-hydroxy-cyclohexyl, 1-aza-bicyclo[2.2.2]oct-2-yl, 1-(C₁₋₄)alkyl-piperidin-3-yl, 1-(2,2-difluoro-ethyl)-piperidin-3-yl, (2-di(C₁₋₄)alkylamino-2-phenyl-ethyl), 1-benzyl-piperidin-3-yl, 1-allyl-piperidin-3-yl, 1-acetyl-piperidin-3-yl, piperidin-3-yl, and phen(C₁₋₄)alkyl;

R₂, R₃, R₄, and R₅ are each independently selected from the group consisting of hydrogen, halo, alkyl, alkoxy, aryl, cyano, and nitro;

M is selected from the group consisting of:

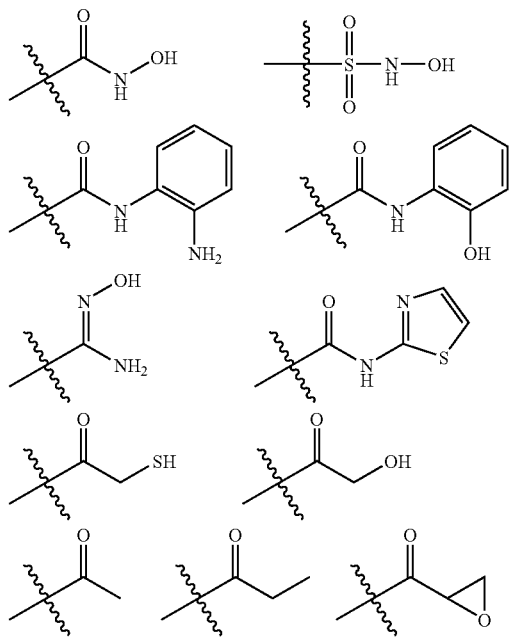

and L is E, Z or mixtures of E/Z —CH₂=CH₂—.

In another embodiment, HDAC inhibitors of the present invention are provided that comprise the formula:

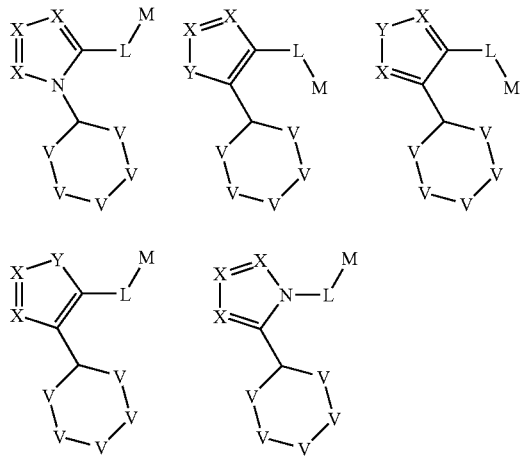

wherein
- each V is independently selected from the group consisting of $C(R_{12})_2$ and $NR_{12}$ where at least one V is $NR_{12}$;
- each X is independently selected from the group consisting of $CR_{12}$ and N;
- each Y is independently selected from the group consisting of O, S and $NR_{12}$;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
- M is a substituent capable of complexing with a deacetylase catalytic site and/or a metal ion; and
- L is a substituent providing between 0-10 atoms separation between M and the ring.

In another embodiment, HDAC inhibitors of the present invention are provided that comprise the formula:

Z-L-M wherein
Z is selected from the group consisting of

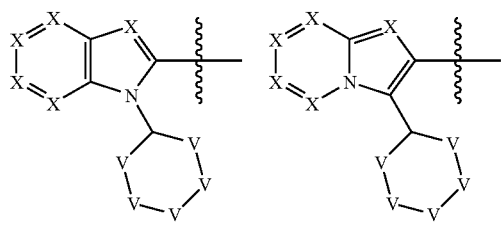

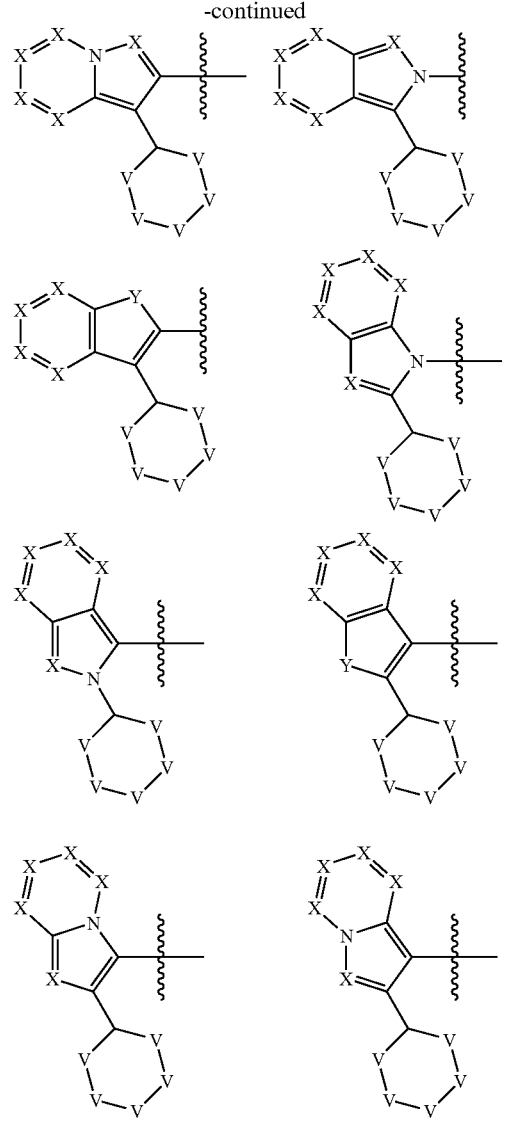

wherein
- each V is independently selected from the group consisting of $C(R_{12})_2$ and $NR_{12}$ where at least one V is $NR_{12}$;
- each X is independently selected from the group consisting of $CR_{12}$ and N;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
- M is a substituent capable of complexing with a deacetylase catalytic site and/or a metal ion; and
- L is a substituent providing between 0-10 atoms separation between M and the ring.

In another embodiment, HDAC inhibitors of the present invention are provided that comprise the formula:

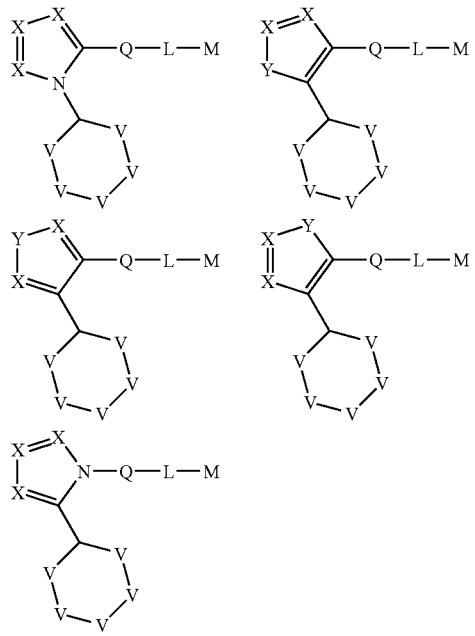

wherein
each V is independently selected from the group consisting of $C(R_{12})_2$ and $NR_{12}$ where at least one V is $NR_{12}$;
each X is independently selected from the group consisting of $CR_{12}$ and N;
each Y is independently selected from the group consisting of O, S and $NR_{12}$;
each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
Q is a substituted or unsubstituted aromatic ring;
M is a substituent capable of complexing with a deacetylase catalytic site and/or a metal ion; and
L is a substituent providing between 0-10 atoms separation between the M substituent and the Q substituent.

In another embodiment, HDAC inhibitors of the present invention are provided that comprise the formula:

Z-Q-L-M wherein
Z is selected from the group consisting of

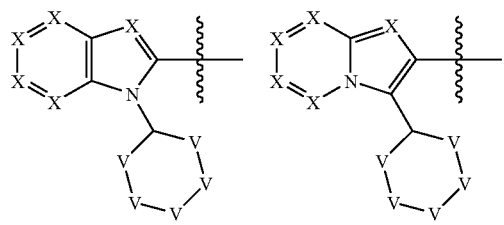

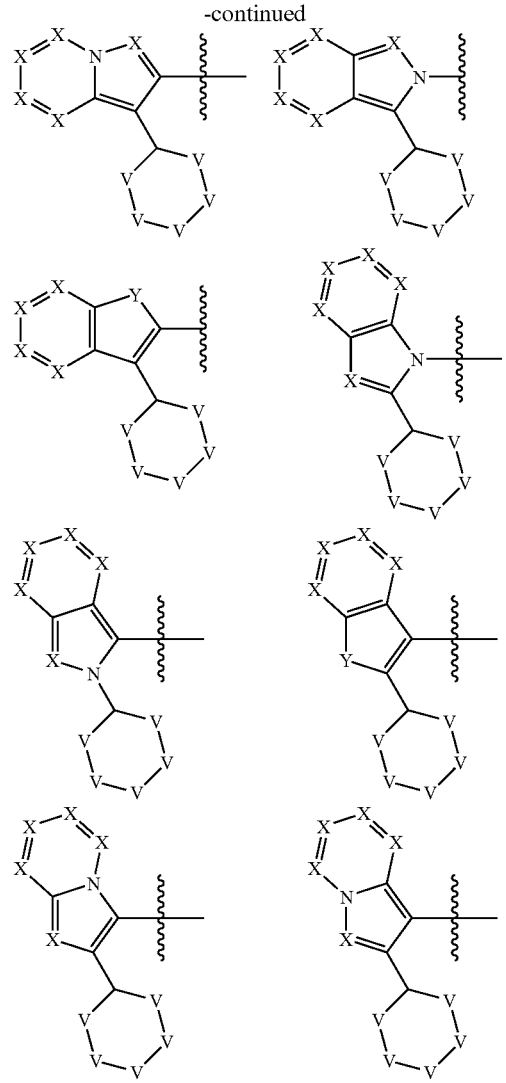

wherein
each V is independently selected from the group consisting of $C(R_{12})_2$ and $NR_{12}$ where at least one V is $NR_{12}$;
each X is independently selected from the group consisting of $CR_{12}$ and N;
each Y is independently selected from the group consisting of O, S and $NR_{12}$;
each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
Q is a substituted or unsubstituted aromatic ring;
M is a substituent capable of complexing with a deacetylase catalytic site and/or a metal ion; and
L is a substituent providing between 0-10 atoms separation between the M substituent and the Q substituent.

In another embodiment, HDAC inhibitors of the present invention are provided that comprise the formula:
Z-Q-L-M
wherein
Z is selected from the group consisting of
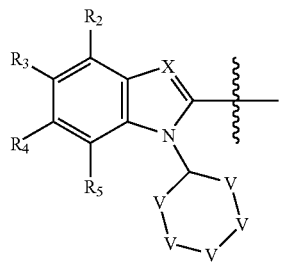
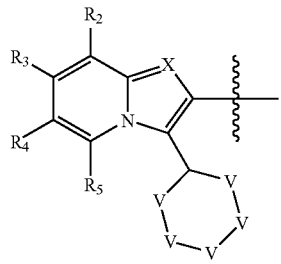
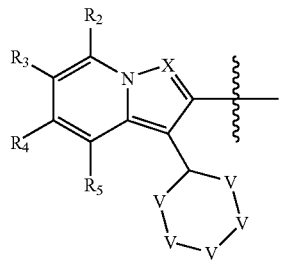
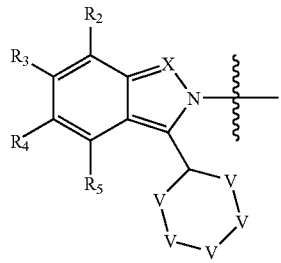
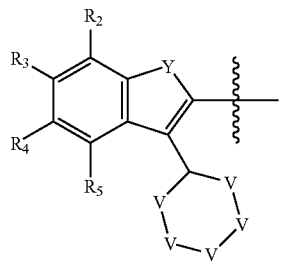
-continued
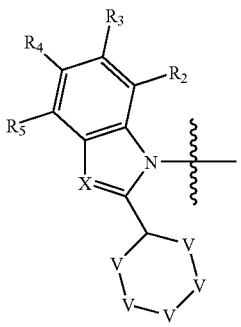 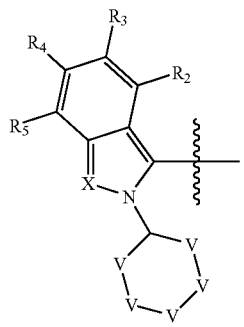
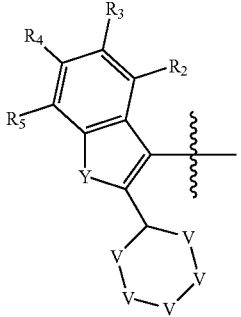 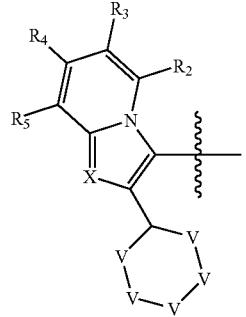
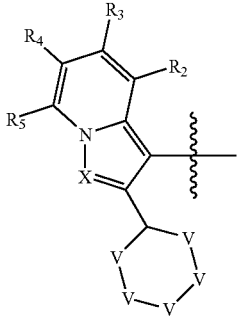 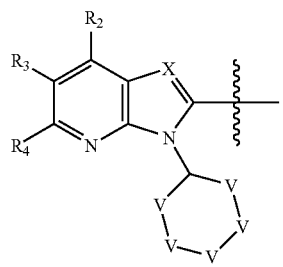
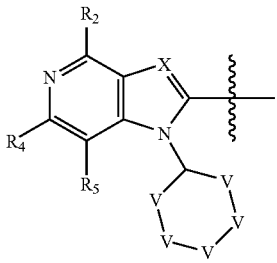
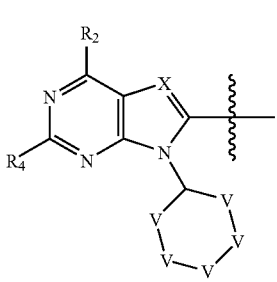

wherein
- each V is independently selected from the group consisting of $C(R_{12})_2$ and $NR_{12}$ where at least one V is $NR_{12}$;
- each X is independently selected from the group consisting of $CR_{12}$ and N;
- each Y is independently selected from the group consisting of O, S and $NR_{12}$;
- $R_2$, $R_3$, $R_4$ and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
- Q is a substituted or unsubstituted aromatic ring;
- M is a substituent capable of complexing with a deacetylase catalytic site and/or a metal ion; and
- L is a substituent providing between 0-10 atoms separation between the M substituent and the Q substituent.

In another embodiment, HDAC inhibitors of the present invention are provided that comprise the formula:

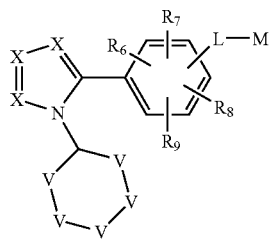

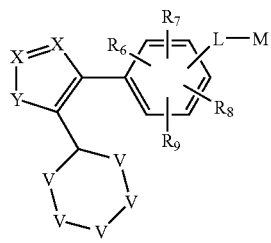

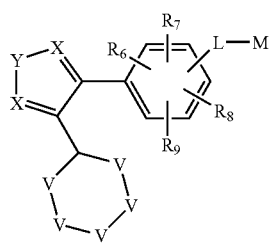

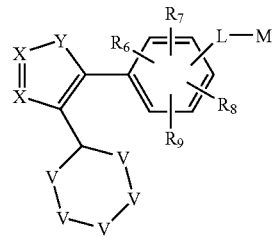

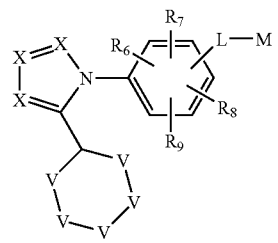

wherein
- each V is independently selected from the group consisting of $C(R_{12})_2$ and $NR_{12}$ where at least one V is $NR_{12}$;
- each X is independently selected from the group consisting of $CR_{12}$ and N;
- each Y is independently selected from the group consisting of O, S and $NR_{12}$;
- $R_6$, $R_7$, $R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
- M is a substituent capable of complexing with a deacetylase catalytic site and/or a metal ion; and
- L is a substituent providing between 0-10 atoms separation between the M substituent and the ring.

In another embodiment, HDAC inhibitors of the present invention are provided that comprise the formula:

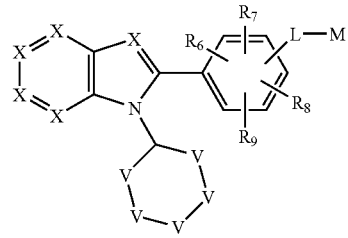

-continued

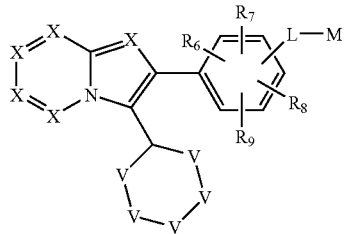

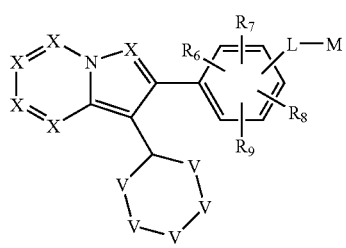

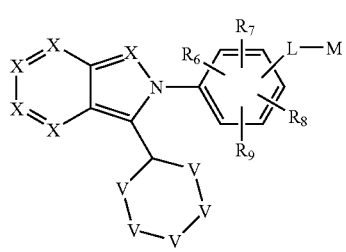

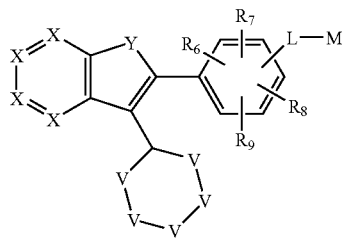

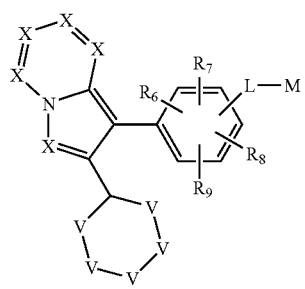

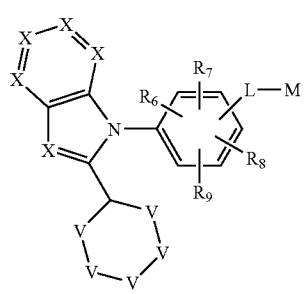

-continued

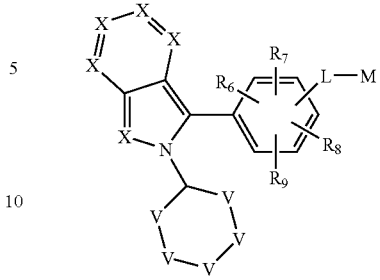

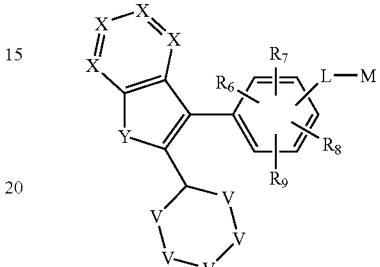

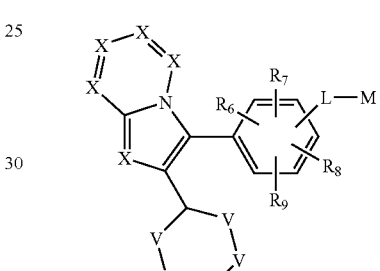

wherein each V is independently selected from the group consisting of $C(R_{12})_2$ and $NR_{12}$ where at least one V is $NR_{12}$;

each X is independently selected from the group consisting of $CR_{12}$ and N;

each Y is independently selected from the group consisting of O, S and $NR_{12}$;

$R_6$, $R_7$, $R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;

each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

M is a substituent capable of complexing with a deacetylase catalytic site and/or a metal ion; and L is a substituent providing between 0-10 atoms separation between the M substituent and the ring.

In another embodiment, HDAC inhibitors of the present invention are provided that comprise the formula:
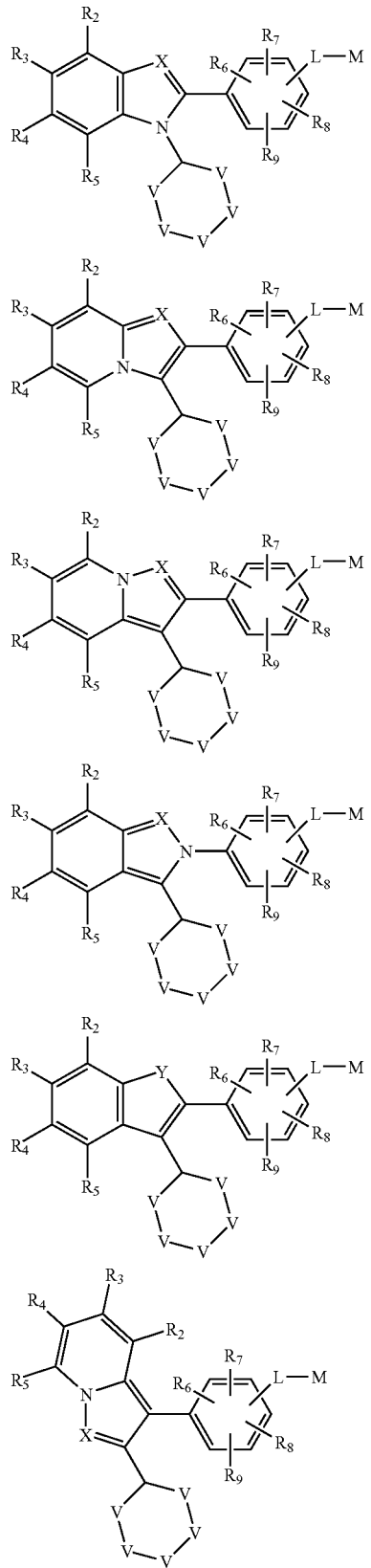
-continued
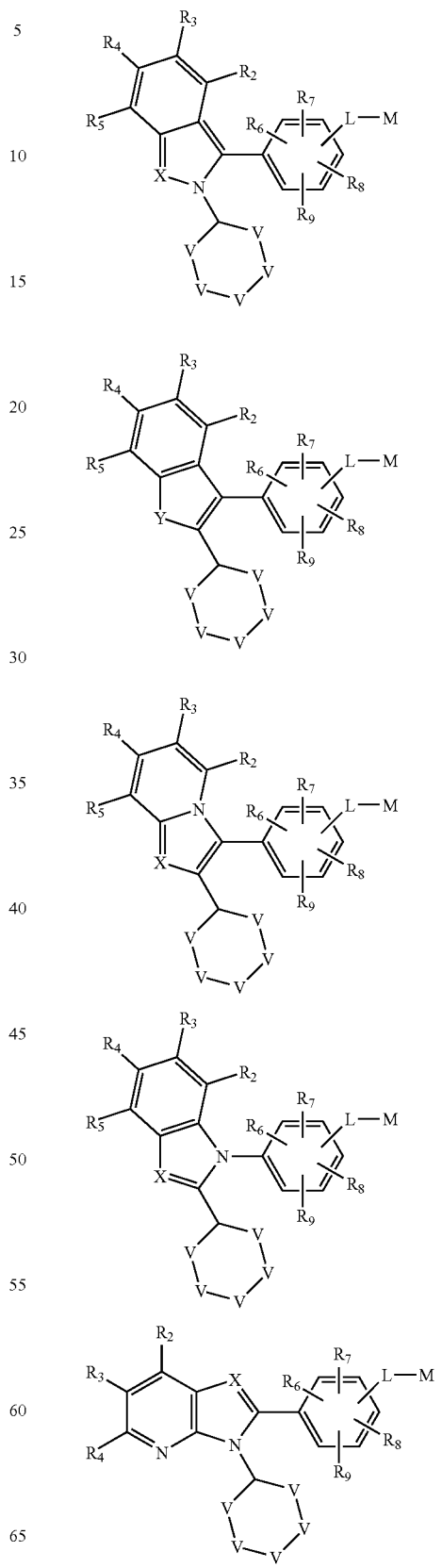

-continued

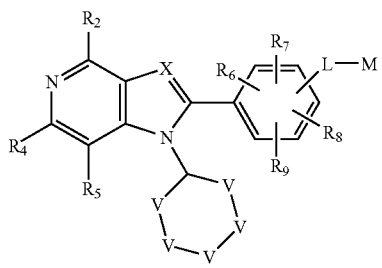

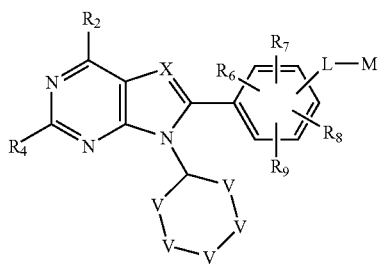

wherein
- each V is independently selected from the group consisting of $C(R_{12})_2$ and $NR_{12}$ where at least one V is $NR_{12}$;
- each X is independently selected from the group consisting of $CR_{12}$ and N;
- each Y is independently selected from the group consisting of O, S and $NR_{12}$;
- $R_2$, $R_3$, $R_4$, $R_5$, $R_6$, $R_7$, $R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
- M is a substituent capable of complexing with a deacetylase catalytic site and/or a metal ion; and
- L is a substituent providing between 0-10 atoms separation between the M substituent and the ring.

In another embodiment, HDAC inhibitors of the present invention are provided that comprise the formula:

Z-Q-L-M wherein
Z is selected from the group consisting of

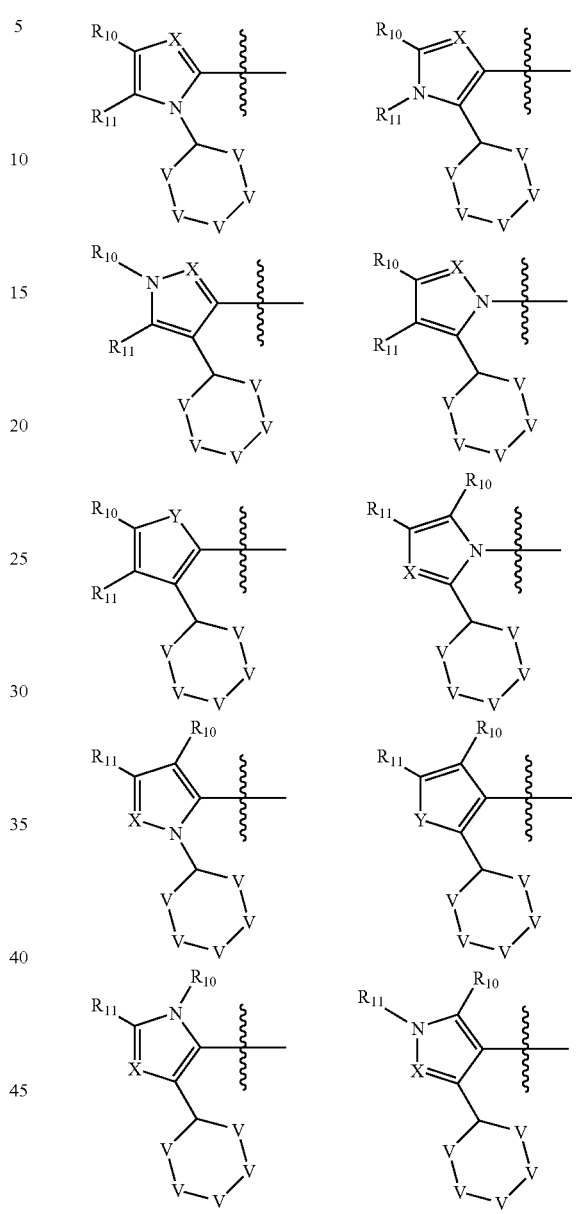

wherein
- each V is independently selected from the group consisting of $C(R_{12})_2$ and $NR_{12}$ where at least one V is $NR_{12}$;
- each X is independently selected from the group consisting of $CR_{12}$ and N;
- each Y is independently selected from the group consisting of O, S and $NR_{12}$;
- $R_{10}$ and $R_{11}$ are taken together to form a substituted or unsubstituted aromatic ring;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

Q is a substituted or unsubstituted aromatic ring;

M is a substituent capable of complexing with a deacetylase catalytic site and/or a metal ion; and L is a substituent providing between 0-10 atoms separation between the M substituent and the Q substituent.

In another embodiment, HDAC inhibitors of the present invention are provided that comprise the formula:

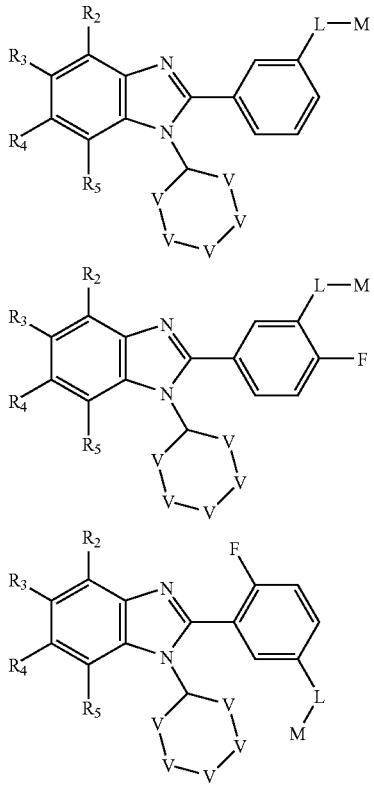

wherein
each V is independently selected from the group consisting of $C(R_{12})_2$ and $NR_{12}$ where at least one V is $NR_{12}$;
each X is independently selected from the group consisting of $CR_{12}$ and N;
each Y is independently selected from the group consisting of O, S and $NR_{12}$;
$R_2$, $R_3$, $R_4$, and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

M is a substituent capable of complexing with a deacetylase catalytic site and/or a metal ion; and L is a substituent providing between 0-10 atoms separation between M and the remainder of the compound.

In another embodiment, HDAC inhibitors of the present invention are provided that comprise the formula:

Z-Q-L-M wherein
Z-Q- is selected from the group consisting of

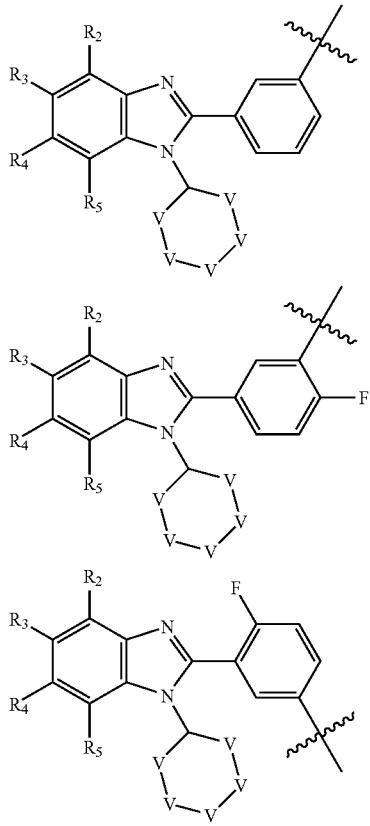

each V is independently selected from the group consisting of $C(R_{12})_2$ and $NR_{12}$ where at least one V is $NR_{12}$;
$R_2$, $R_3$, $R_4$, and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

M is a substituent capable of complexing with a deacetylase catalytic site and/or a metal ion; and L is a substituent providing between 2-10 atoms separation between M and the Q substituent.

In another embodiment, HDAC inhibitors of the present invention are provided that comprise the formula:

Z-Q-L-M wherein

Z-Q- is selected from the group consisting of

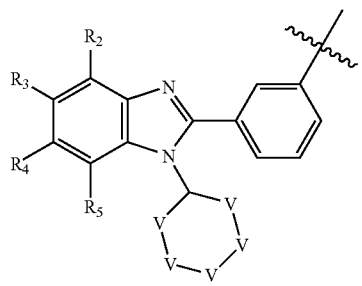

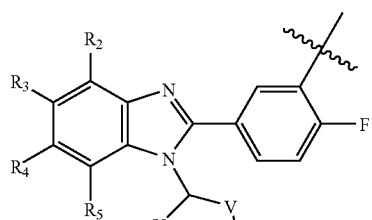

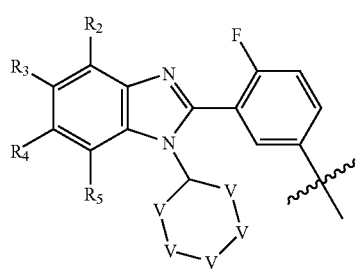

each V is independently selected from the group consisting of C(R$_{12}$)$_2$ and NR$_{12}$ where at least one V is NR$_{12}$;

R$_2$, R$_3$, R$_4$, and R$_5$ are each independently selected from the group consisting of hydrogen, halo, alkyl, alkoxy, aryl, cyano, and nitro;

each R$_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that R$_{12}$ is not halo, cyano, nitro, and thio in the case where the ring atom to which R$_{12}$ is bound is nitrogen;

M is selected from the group consisting of

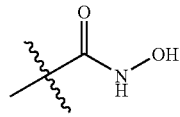 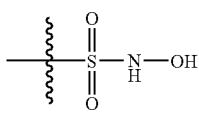

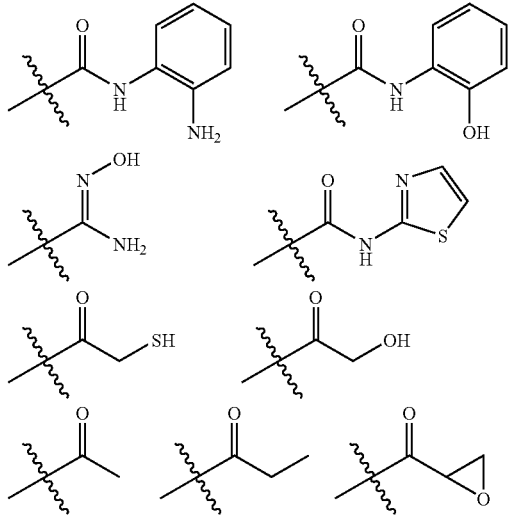

and L is E, Z or mixtures of E/Z —CH$_2$=CH$_2$—.

In another embodiment, HDAC inhibitors of the present invention are provided that comprise the formula:

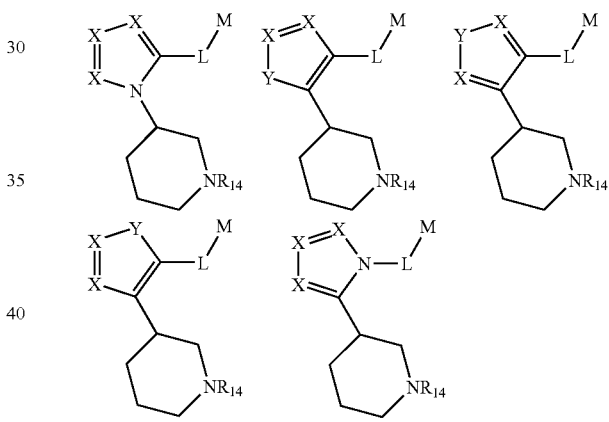

wherein each X is independently selected from the group consisting of CR$_{12}$ and N;

each Y is independently selected from the group consisting of O, S and NR$_{12}$;

each R$_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that R$_{12}$ is not halo, cyano, nitro, and thio in the case where the ring atom to which R$_{12}$ is bound is nitrogen;

R$_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;

M is a substituent capable of complexing with a deacetylase catalytic site and/or a metal ion; and L is a substituent providing between 0-10 atoms separation between M and the ring.

In another embodiment, HDAC inhibitors of the present invention are provided that comprise the formula:

Z-L-M wherein

Z is selected from the group consisting of

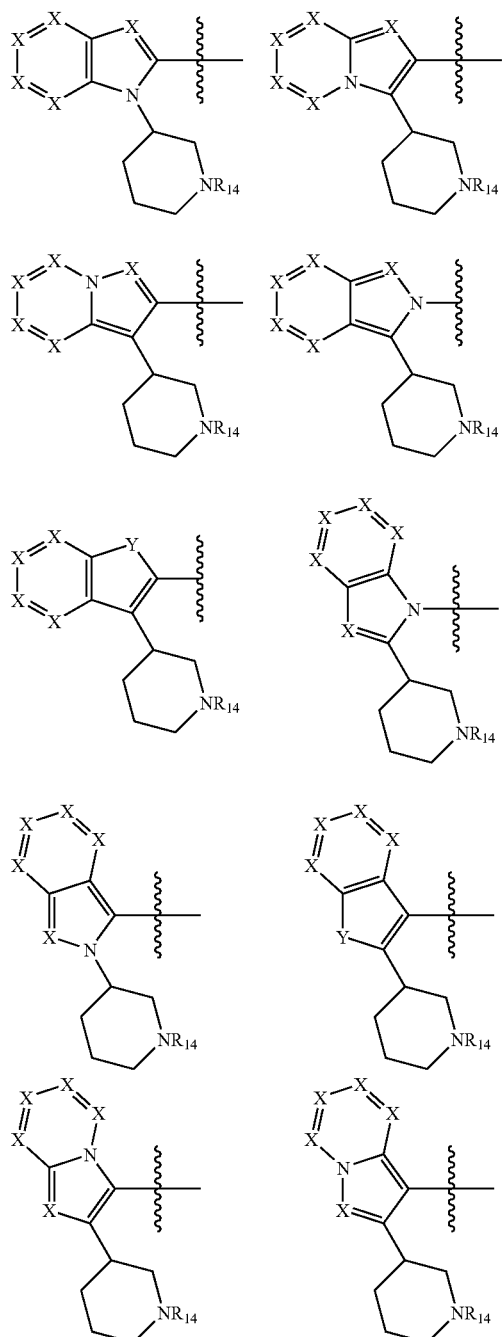

wherein
each X is independently selected from the group consisting of $CR_{12}$ and N;

each Y is independently selected from the group consisting of O, S and $NR_{12}$;

each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

$R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;

M is a substituent capable of complexing with a deacetylase catalytic site and/or a metal ion; and L is a substituent providing between 0-10 atoms separation between M and the ring.

In another embodiment, HDAC inhibitors of the present invention are provided that comprise the formula:

Z-Q-L-M wherein

Z is selected from the group consisting of

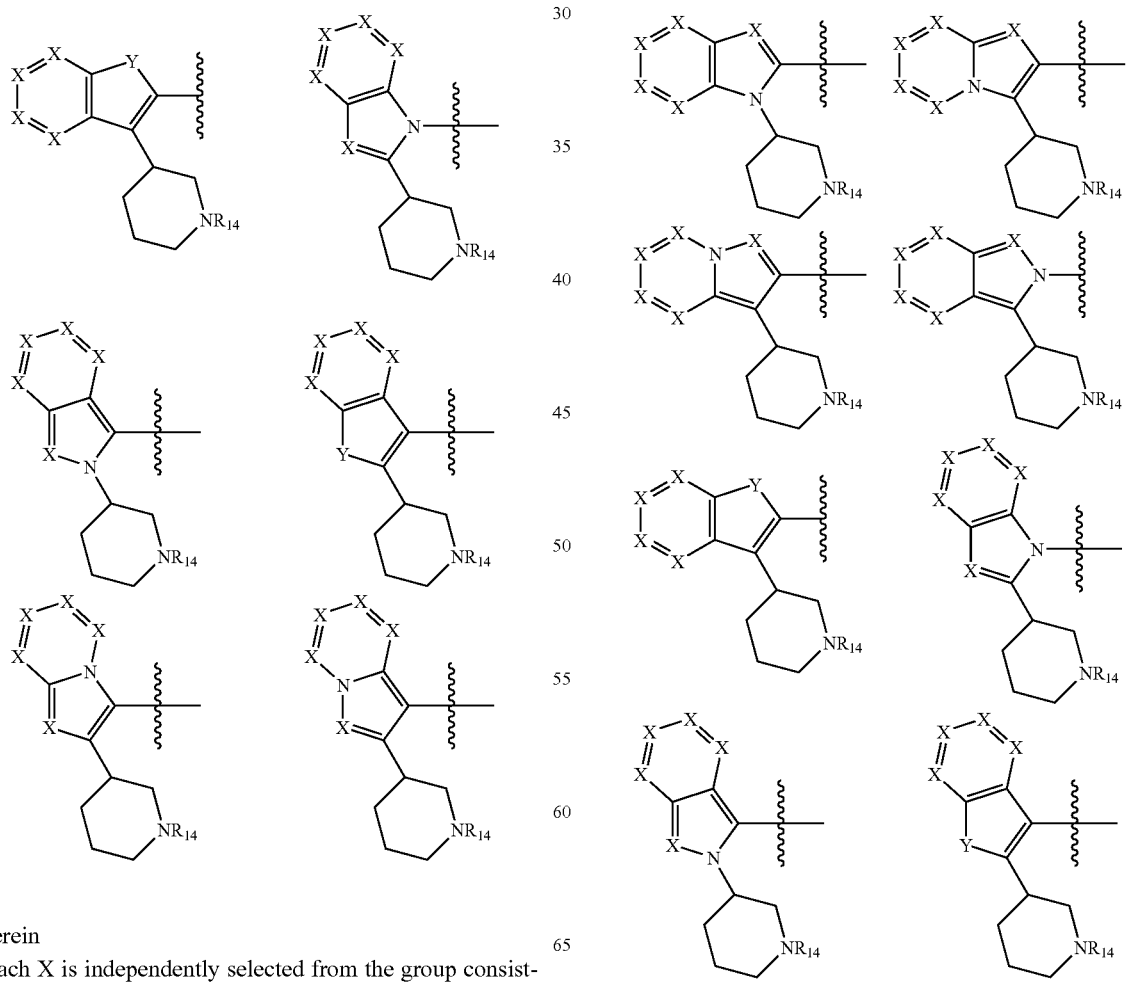

-continued

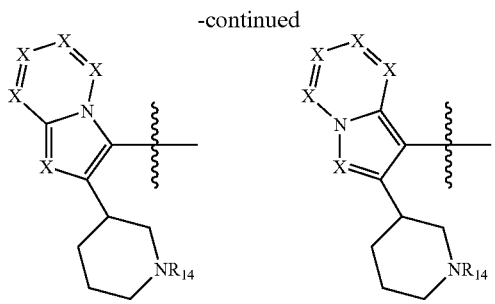

wherein
each X is independently selected from the group consisting of $CR_{12}$ and N;
each Y is independently selected from the group consisting of O, S and $NR_{12}$;
each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
$R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;
Q is a substituted or unsubstituted aromatic ring;
M is a substituent capable of complexing with a deacetylase catalytic site and/or a metal ion; and
L is a substituent providing between 0-10 atoms separation between the M substituent and the Q substituent.

In another embodiment, HDAC inhibitors of the present invention are provided that comprise the formula:

Z-Q-L-M wherein
Z is selected from the group consisting of

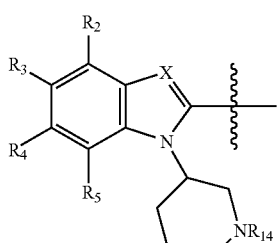

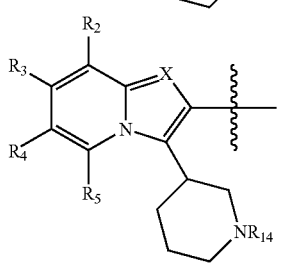

-continued

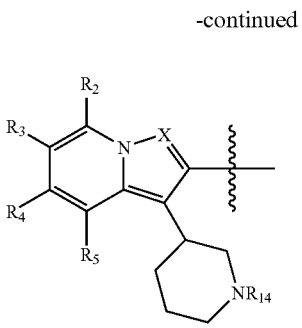

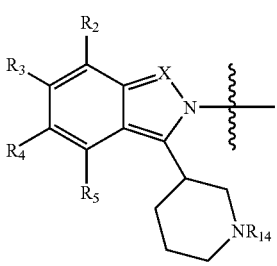

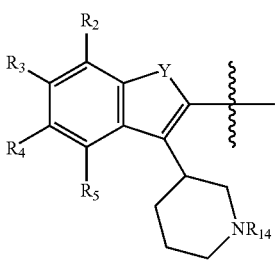

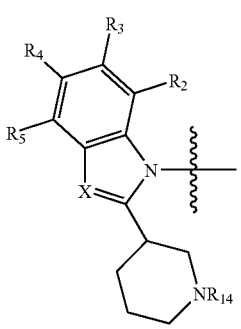 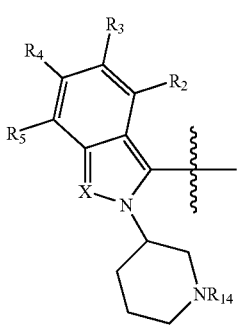

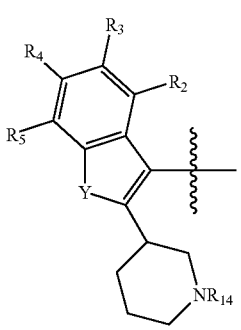 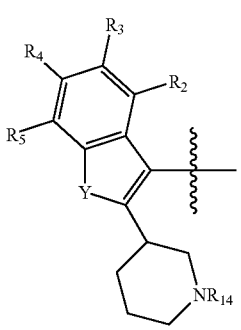

-continued

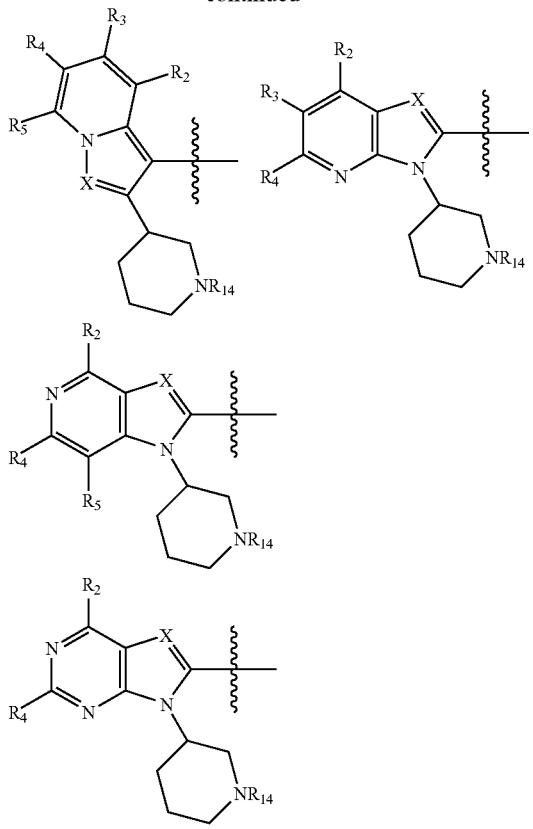

wherein
- each X is independently selected from the group consisting of $CR_{12}$ and N;
- each Y is independently selected from the group consisting of O, S and $NR_{12}$;
- $R_2$, $R_3$, $R_4$ and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted; and
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
- $R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;
- Q is a substituted or unsubstituted aromatic ring;
- M is a substituent capable of complexing with a deacetylase catalytic site and/or a metal ion; and
- L is a substituent providing between 0-10 atoms separation between the M substituent and the Q substituent.

In another embodiment, HDAC inhibitors of the present invention are provided that comprise the formula:

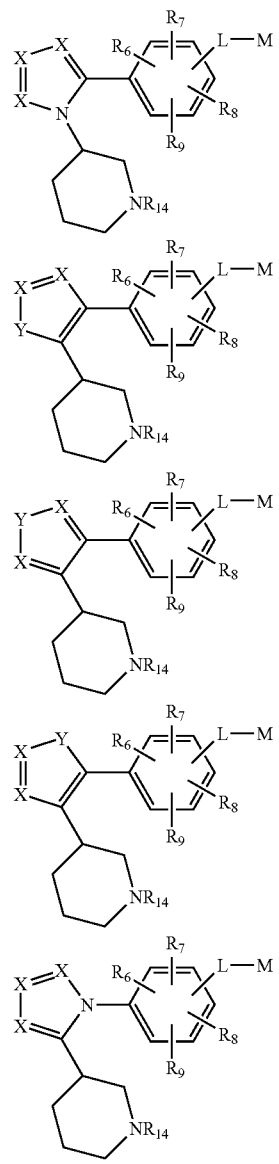

wherein
- each X is independently selected from the group consisting of $CR_{12}$ and N;
- each Y is independently selected from the group consisting of O, S and $NR_{12}$;
- $R_6$, $R_7$, $R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

$R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;

M is a substituent capable of complexing with a deacetylase catalytic site and/or a metal ion; and L is a substituent providing between 0-10 atoms separation between the M substituent and the ring.

In another embodiment, HDAC inhibitors of the present invention are provided that comprise the formula:

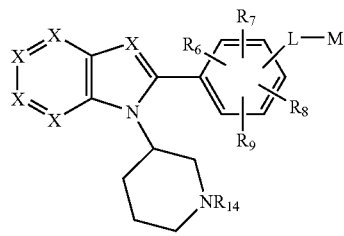

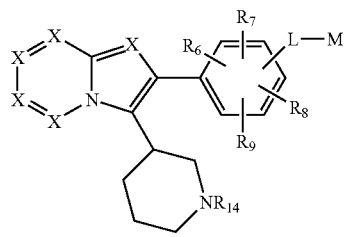

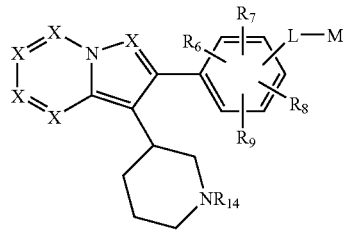

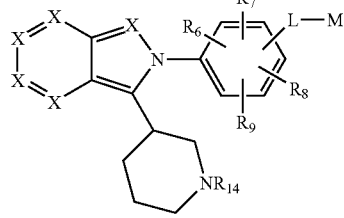

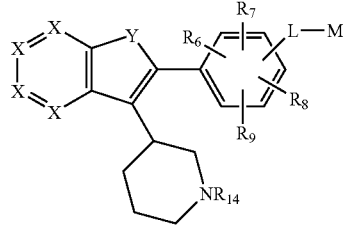

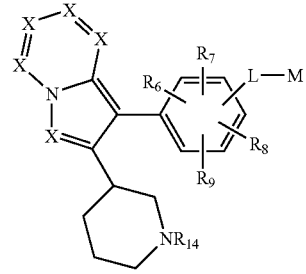

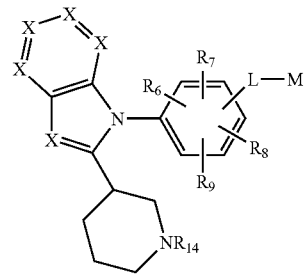

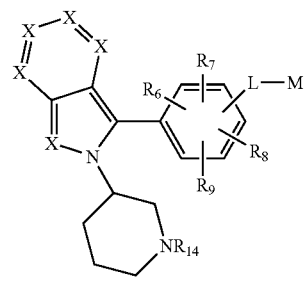

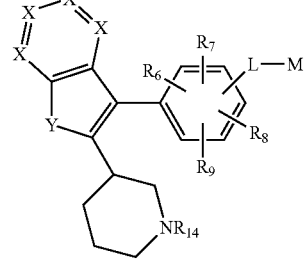

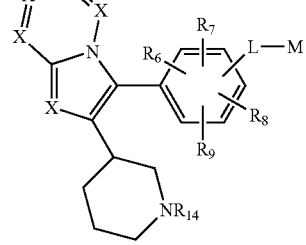

wherein
each X is independently selected from the group consisting of $CR_{12}$ and N;
each Y is independently selected from the group consisting of O, S and $NR_{12}$;
$R_6$, $R_7$, $R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;

each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

$R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;

M is a substituent capable of complexing with a deacetylase catalytic site and/or a metal ion; and L is a substituent providing between 0-10 atoms separation between the M substituent and the ring.

In another embodiment, HDAC inhibitors of the present invention are provided that comprise the formula:

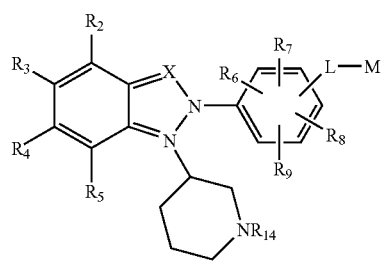

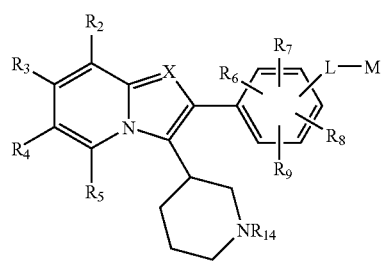

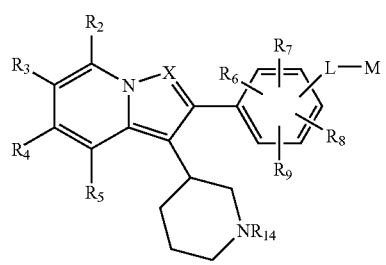

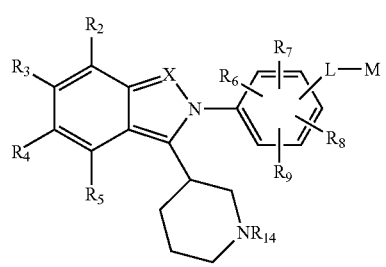

-continued

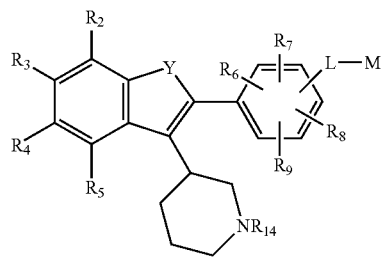

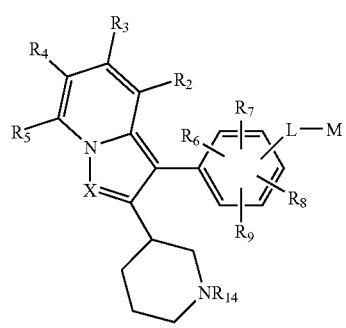

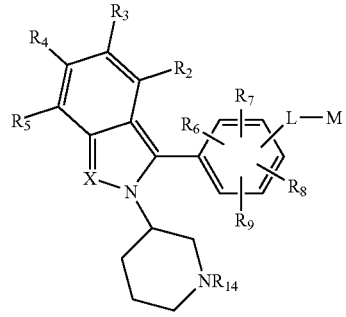

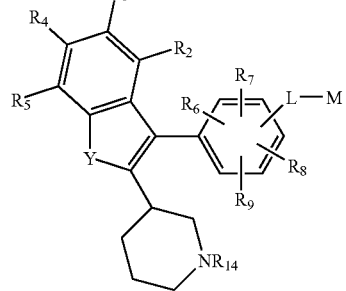

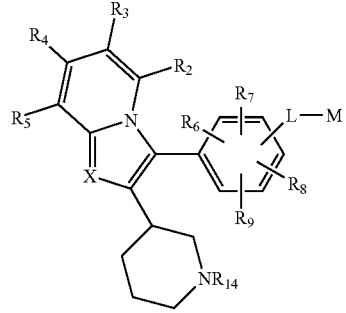

-continued

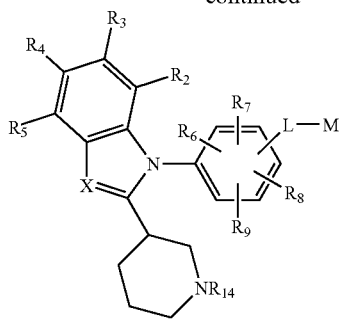

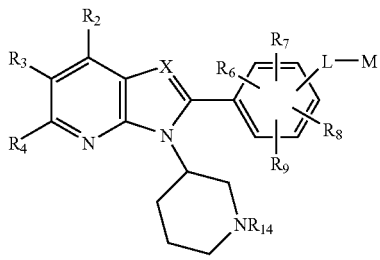

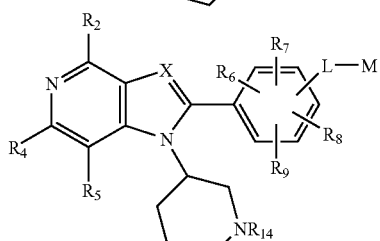

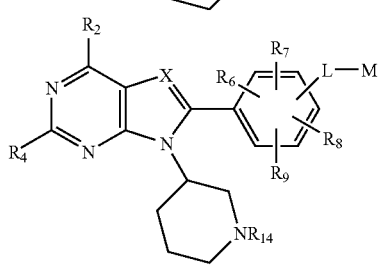

wherein
- each X is independently selected from the group consisting of $CR_{12}$ and N;
- each Y is independently selected from the group consisting of O, S and $NR_{12}$;
- $R_2, R_3, R_4, R_5, R_6, R_7, R_8$, and $R_9$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;
- each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;
- $R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;
- M is a substituent capable of complexing with a deacetylase catalytic site and/or a metal ion; and
- L is a substituent providing between 0-10 atoms separation between the M substituent and the ring.

In another embodiment, HDAC inhibitors of the present invention are provided that comprise the formula:

Z-Q-L-M wherein
Z is selected from the group consisting of

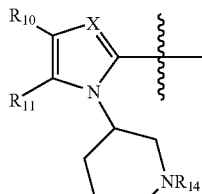 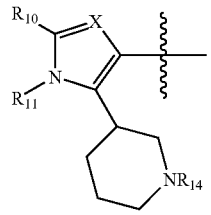

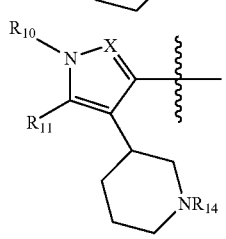 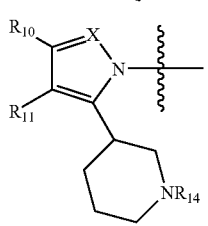

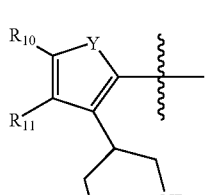 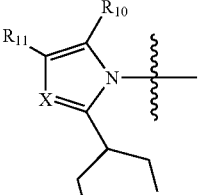

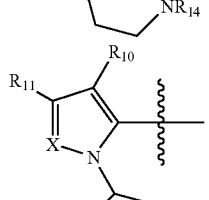 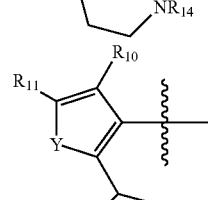

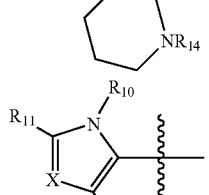 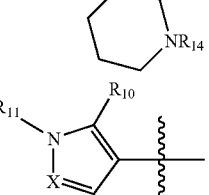

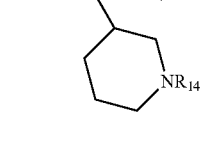 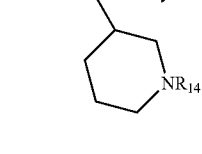

wherein
each X is independently selected from the group consisting of $CR_{12}$ and N;

each Y is independently selected from the group consisting of O, S and $NR_{12}$;

$R_{10}$ and $R_{11}$ are taken together to form a substituted or unsubstituted aromatic ring;

each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that $R_{12}$ is not halo, cyano, nitro, and thio in the case where the ring atom to which $R_{12}$ is bound is nitrogen;

$R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;

Q is a substituted or unsubstituted aromatic ring;

M is a substituent capable of complexing with a deacetylase catalytic site and/or a metal ion; and L is a substituent providing between 0-10 atoms separation between the M substituent and the Q substituent.

In another embodiment, HDAC inhibitors of the present invention are provided that comprise the formula:

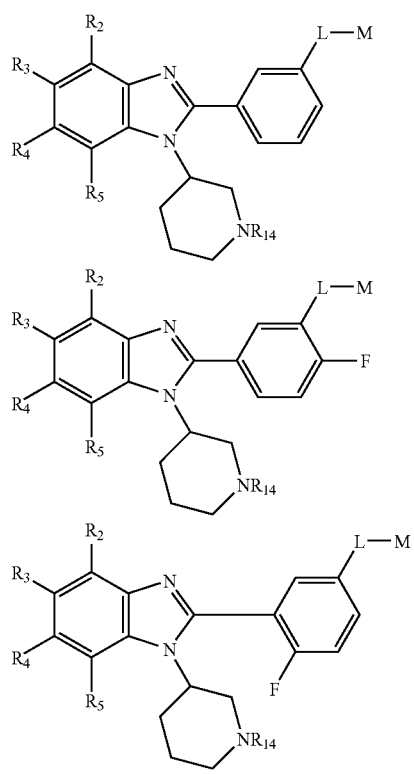

wherein $R_2$, $R_3$, $R_4$, and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;

$R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;

M is a substituent capable of complexing with a deacetylase catalytic site and/or a metal ion; and L is a substituent providing between 0-10 atoms separation between the M substituent and the remainder of the compound.

In another embodiment, HDAC inhibitors of the present invention are provided that comprise the formula:

Z-Q-L-M wherein

Z-Q- is selected from the group consisting of

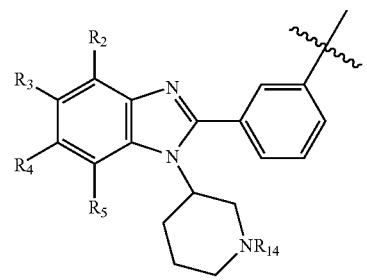

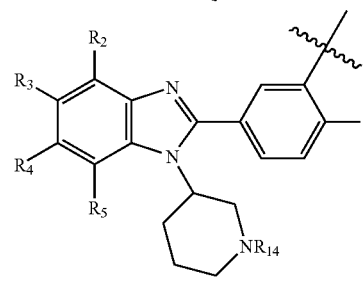

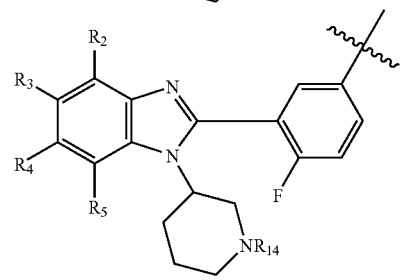

wherein $R_2$, $R_3$, $R_4$, and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;

$R_{14}$ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;

M is a substituent capable of complexing with a deacetylase catalytic site and/or a metal ion; and L is a substituent providing between 2-10 atoms separation between the M substituent and the Q substituent.

In another embodiment, HDAC inhibitors of the present invention are provided that comprise the formula:

Z-Q-L-M wherein

Z-Q- is selected from the group consisting of

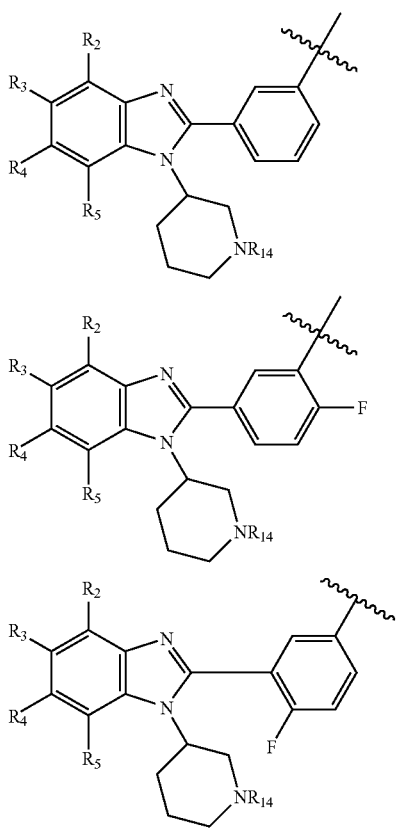

wherein
- R₂, R₃, R₄, and R₅ are each independently selected from the group consisting of hydrogen, halo, alkyl, alkoxy, aryl, cyano, and nitro;
- R₁₄ is selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted;
- M is selected from the group consisting of

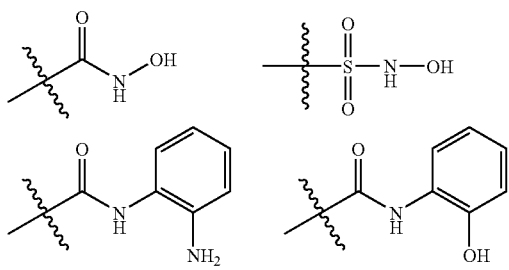

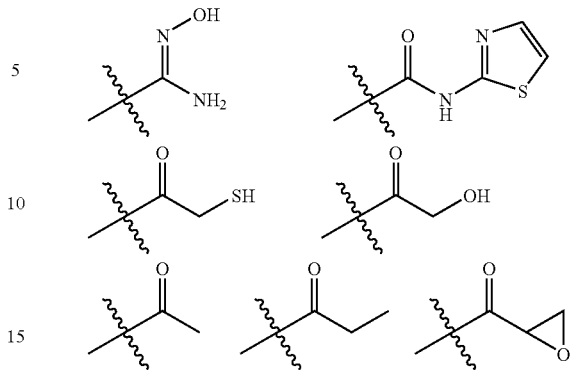

and L is E, Z or mixtures of E/Z —CH₂═CH₂—.

In one variation of any of the above embodiments comprising Q, Q is a substituted or unsubstituted phenyl ring. In another variation of any of the above embodiments comprising Q, Q is a substituted or unsubstituted heteroaryl. In still another variation of any of the above embodiments comprising Q, Q is a substituted or unsubstituted heteroaryl selected from the group consisting of furan, thiophene, pyrrole, pyrazole, triazole, isoxazole, oxazole, thiazole, isothiazole, oxadiazole, pyridine, pyridazine, pyrimidine, pyrazine, triazine, benzofuran, isobenzofuran, benzothiophene, isobenzothiophene, indole, isobenzazole, quinoline, isoquinoline, cinnoline, quinazoline, naphthyridine, pyridopyridine, quinoxaline, phthalazine, benthiazole, and triazine.

In one variation of any of the above embodiments and variations comprising X, at least one X in the six membered ring is a substituted carbon atom. In another variation of any of the above embodiments and variations comprising X, at least one X in the six membered ring is —CF.

In one variation of any of the above embodiments and variations comprising X, any two adjacent X moieties may optionally be CR₁₂ where the R₁₂ substituents are taken together to form a ring.

In one variation of any of the above embodiments and variations comprising M, M comprises a member selected from the group consisting of trifluoroacetyl (—C(O)—CF₃), —NH—P(O)OH—CH₃, sulfonamides (—SO₂NH₂), hydroxysulfonamides (—SO₂NHOH), thiols (—SH), and carbonyl groups having the formula —C(O)—R₁₃ wherein R₁₃ is hydroxylamino, hydroxyl, amino, alkylamino, or an alkoxy group. In another variation of any of the above embodiments and variations comprising M, M comprises a hydroxamic acid. In yet another variation of any of the above embodiments and variations comprising M, M is selected from the group consisting of:

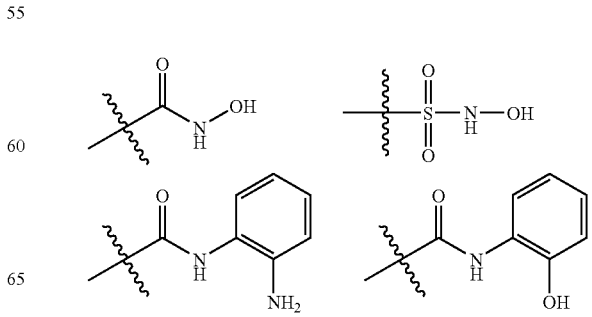

-continued

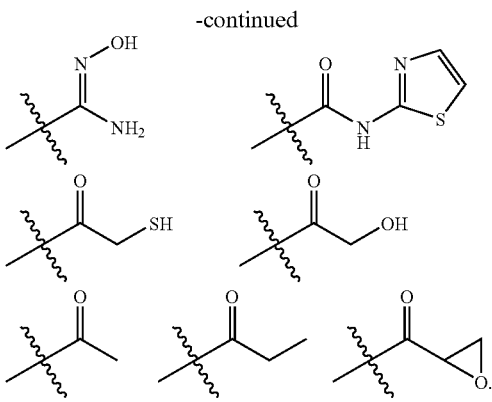

In one variation of any of the above embodiments and variations comprising QLM, QLM is

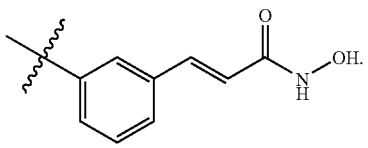

In another variation of any of the above embodiments and variations comprising QLM, QLM is

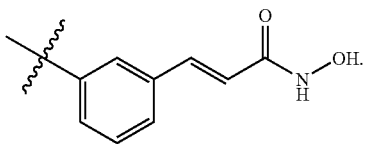

In one variation of any of the above embodiments and variations comprising LM, LM is

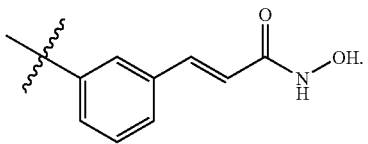

In another variation of any of the above embodiments and variations comprising LM, LM is

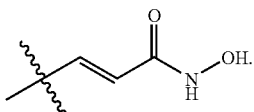

In one variation of any of the above embodiments and variations comprising $R_2$, $R_3$, $R_4$, and $R_5$, at least one of $R_2$, $R_3$, $R_4$, or $R_5$ is fluorine.

In one variation of any of the above embodiments and variations comprising $R_6$, $R_7$, $R_8$, and $R_9$, at least one of $R_6$, $R_7$, $R_8$, or $R_9$ is fluorine.

In one variation of any of the above embodiments and variations comprising $R_6$, $R_7$, $R_8$, and $R_9$, it is noted that $R_6$, $R_7$, $R_8$ or $R_9$ may be selected such that the phenyl ring linking the five membered ring and the L group comprise one or two fluorines as indicated in the structural subunit below:

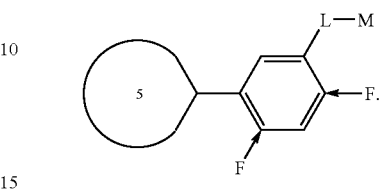

In one variation of any of the above embodiments and variations comprising $R_6$, $R_7$, $R_8$, and $R_9$, it is also noted in regard to the $R_6$, $R_7$, $R_8$ and $R_9$ substituents that any two adjacent substituents may be taken together to form a ring.

In one variation of any of the above embodiments and variations comprising $R_{10}$ and $R_{11}$, it is noted that the substituted or unsubstituted aromatic ring formed when $R_{10}$ and $R_{11}$ are taken together may optionally be a substituted or unsubstituted aryl or a heteroaryl.

In one variation of any of the above embodiments and variations comprising V, each V is selected so that the ring is an unsubstituted or substituted piperdin-3-yl moiety.

In one variation of any of the above embodiments and variations comprising $R_{14}$, $R_{14}$ comprises a member selected from the group consisting of hydrogen and a substituent that is convertible in vivo to hydrogen.

In another variation of any of the above embodiments and variations comprising $R_{14}$, $R_{14}$ is a substituted or unsubstituted $C_{1-6}$ alkyl. In still another variation of any of the above embodiments and variations comprising $R_{14}$, $R_{14}$ is a substituted or unsubstituted —$C(O)C_{1-6}$ alkyl. In a further variation of any of the above embodiments and variations comprising $R_{14}$, $R_{14}$ is selected from the group consisting of hydrogen, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, and a carbonyl group, each substituted or unsubstituted. In yet another variation of any of the above embodiments and variations comprising $R_{14}$, $R_{14}$ is selected from the group consisting of H, methyl, ethyl, propyl, isopropyl, butyl, acetyl, and BOC.

It is noted in regard to each of the above embodiments that a given alkyl, alkoxy, aryloxy, heteroaryloxy, aryl, heteroaryl, aminosulfonyl, alkylsulfonyl, arylsulfonyl, heteroarylsulfonyl, amino, thio, or carbonyl group substituent may optionally be further substituted. As also noted, such two substituents may be taken together to form a ring. Examples of further substituted alkyl groups include, but are not limited to, those selected from the group consisting of haloalkyl, cycloalkyl, aminoalkyl, oxaalkyl, heteroaralkyl, and aralkyl, each of which may optionally be further substituted. Examples of further substituted alkoxy aryloxy, and heteroaryloxy groups include, but are not limited to, those selected from the group consisting of haloalkoxy, haloaryloxy, and haloheteroaryloxy, each of which may optionally be further substituted. Examples of further substituted aminosulfonyl, alkylsulfonyl, arylsulfonyl, and heteroarylsulfonyl groups include, but are not limited to, those selected from the group consisting of alkylaminosulfonyl, arylaminosulfonyl, heteroarylaminosulfonyl, heteroaralkylsulfonyl, and aralkylsulfonyl, each of which may optionally be further substituted. Examples of further substituted amino groups include, but are not limited to, those selected from the group consisting of alkylamino, arylamino, and acylamino, each of which may optionally be further substituted. Examples of further substituted thio groups include, but are not limited to, those selected from the group consisting of alkylthio, arylthio, and heteroarylthio, each of which may optionally be further substituted. Examples of further substituted carbonyl groups include, but are not limited to, acids, acid halides, amides, esters, and ketones. For example, the carbonyl groups may be an alkylcarbonyl, arylcarbonyl, heteroarylcarbonyl, aminocarbonyl, alkoxycarbonyl, aralkoxycarbonyl, or heteroaralkoxycarbonyl, each of which may optionally be further substituted.

It is noted that the preceding lists of examples are not intended to be limiting as other forms of alkyl, alkoxy, aryloxy, heteroaryloxy, aryl, heteroaryl, aminosulfonyl, alkylsulfonyl, arylsulfonyl, heteroarylsulfonyl, amino, and thio groups may also be formed with the addition of other substituents to the base group, some of which are described herein and all of which are intended to fall within the scope of the present invention.

Substituent $R_1$

Figure 2A:
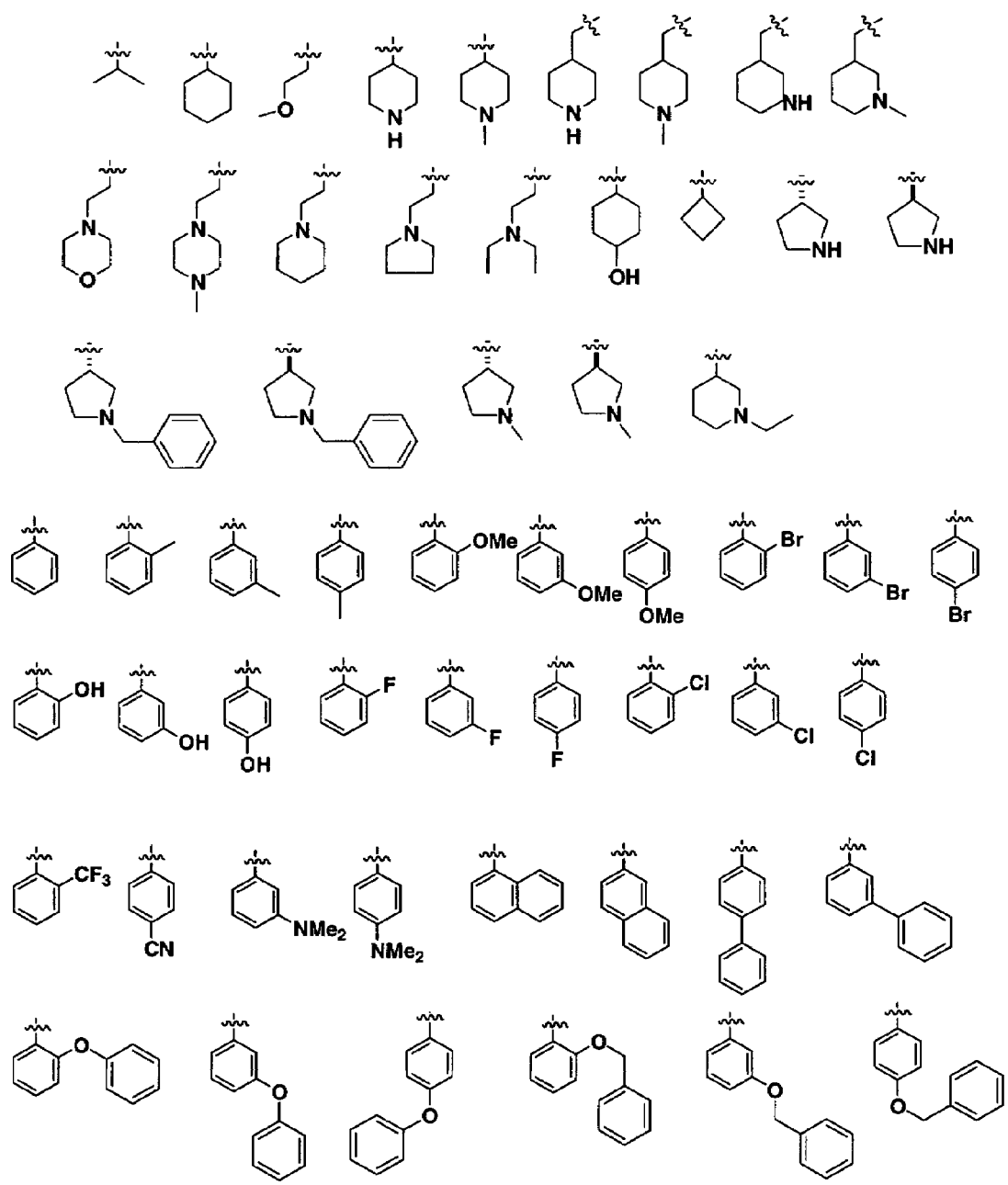
FIG. 2A illustrates particular examples of substituent $R_1$ that may be employed in the Z moiety.
Figure 2A:
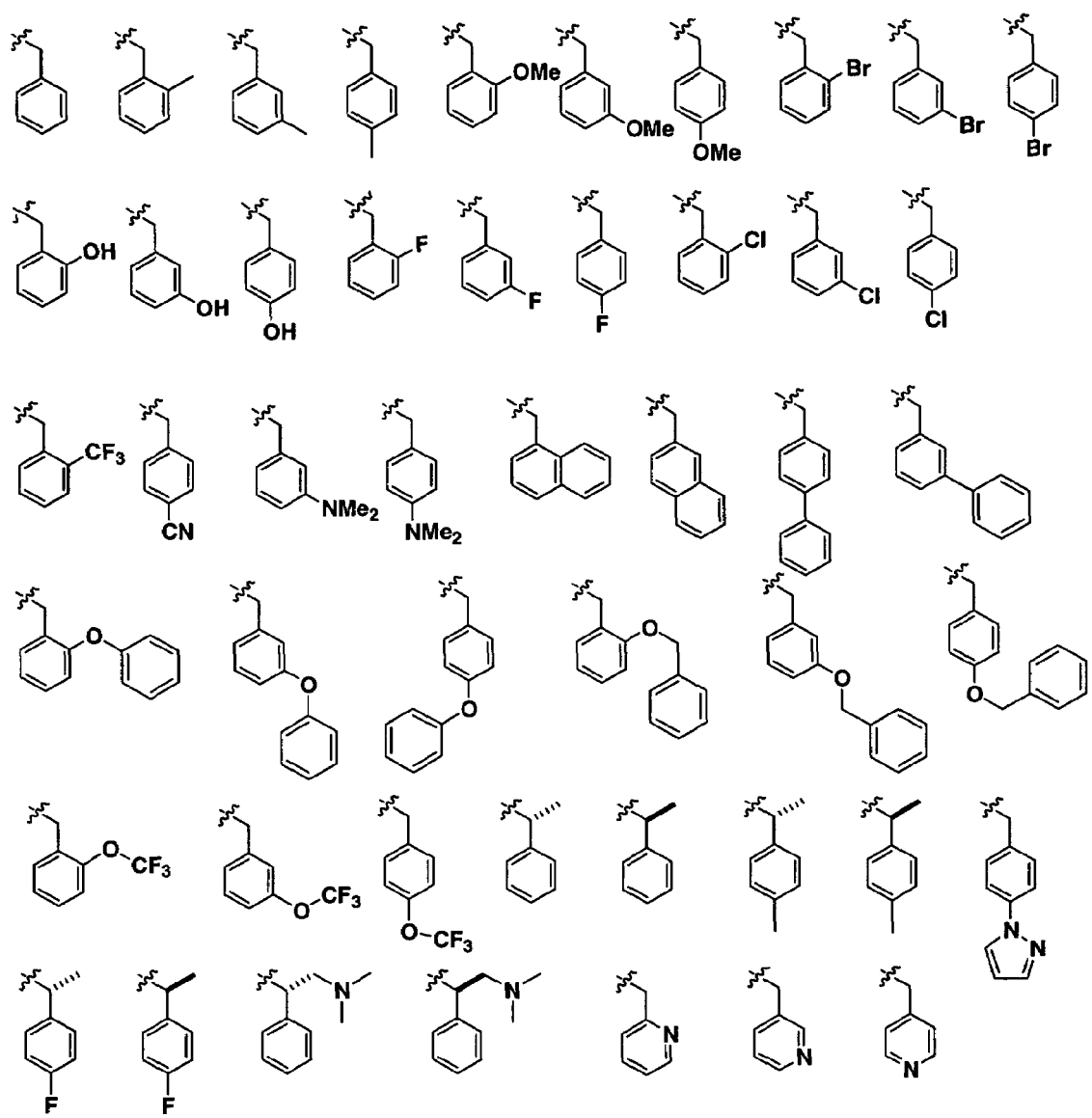
Figure 2A:
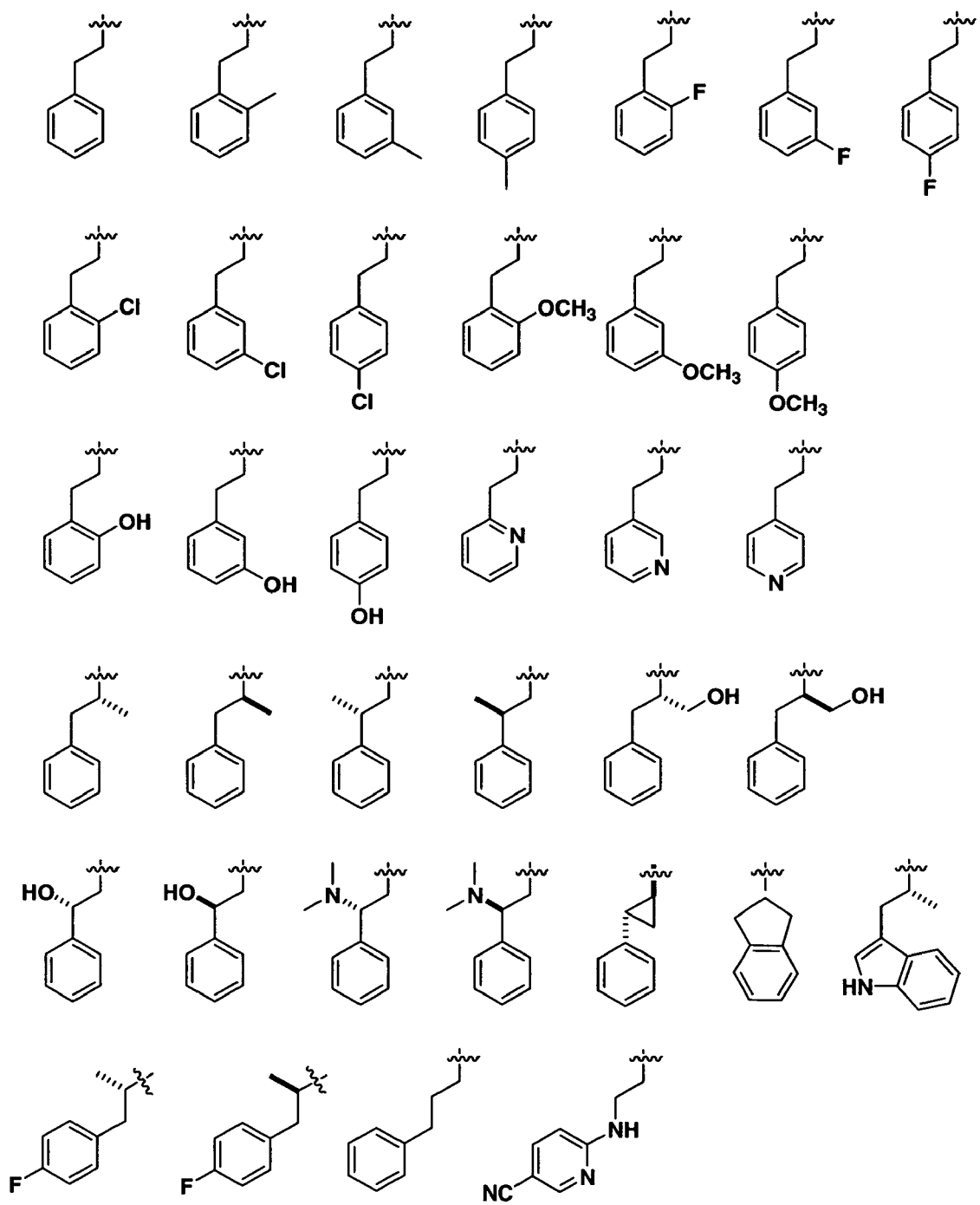
Figure 2A:
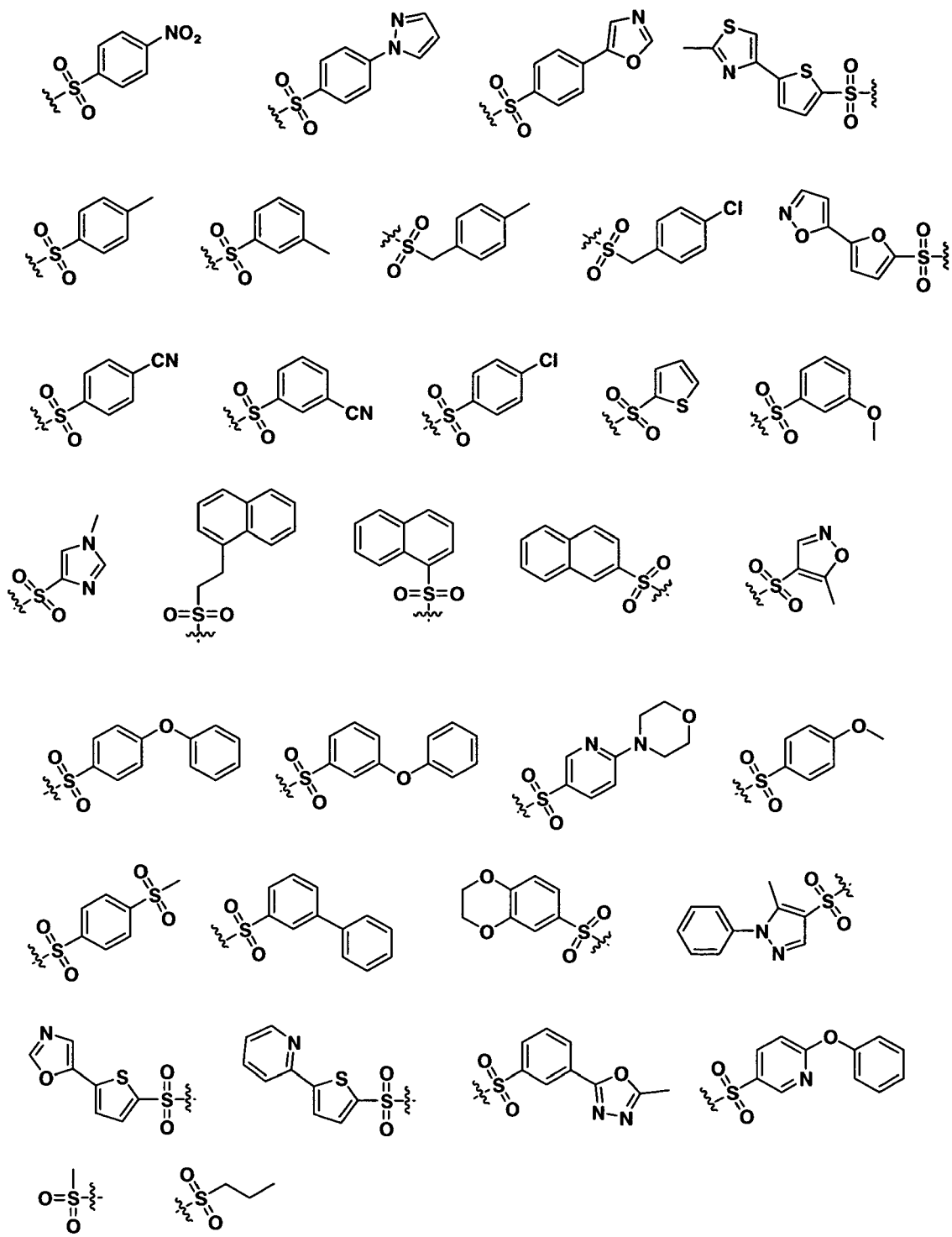
Figure 2A:
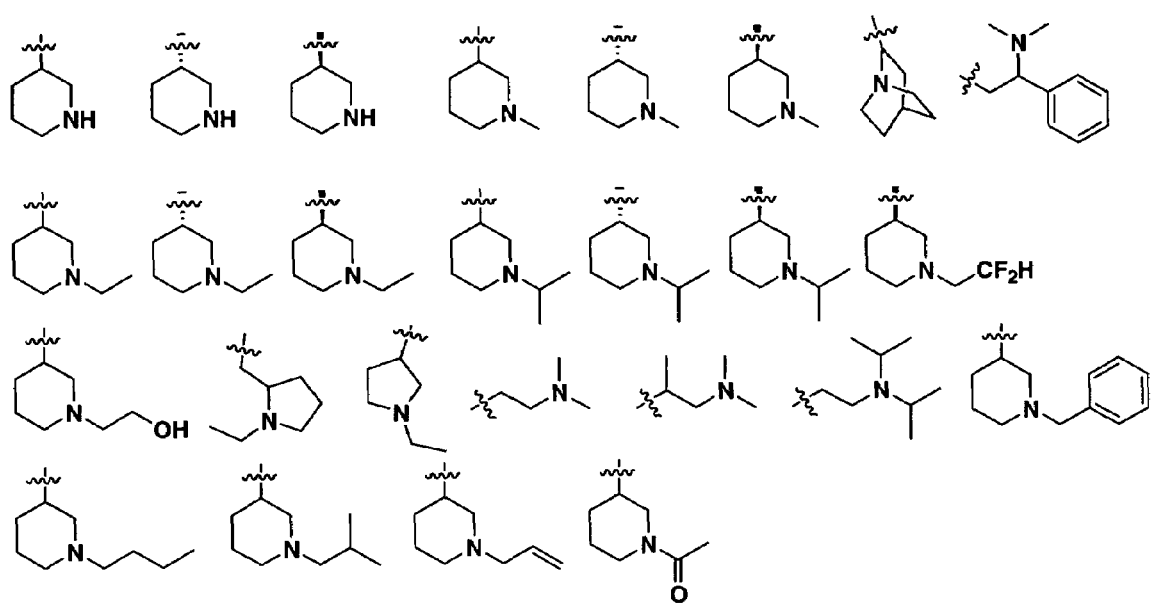

FIG. 2A illustrates particular examples of moieties that may be used as a $R_1$ substituent. The below table also provides examples of different compounds having different $R_1$ substituents.

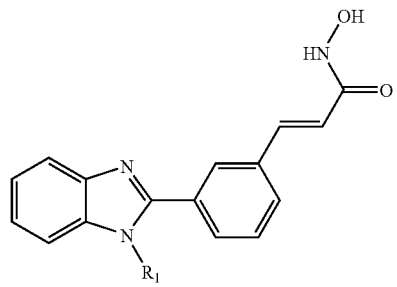

$R_1$ Substituents

| | |
|---|---|
| H | (S)-1-isopropyl-piperidin-3-yl |
| Me | 1-piperidin-4-ylmethyl |
| Et | phenyl |
| isopropyl | 2-chlorophenyl |
| (±)-1-methyl-piperidin-3-yl | 3-chlorophenyl |
| (R)-1-methyl-piperdin-3-yl | 4-chlorophenyl |
| (S)-1-methyl-piperidin-3-yl | 2-methoxy-phenyl |
| (±)-1-ethyl-piperidin-3-yl | 3-methoxy-phenyl |
| (R)-1-ethyl-piperidin-3-yl | 4-methoxy-phenyl |
| (S)-1-ethyl-piperidin-3-yl | 4-phenoxy-phenyl |
| (±)-1-isopropyl-piperidin-3-yl | benzyl |
| (R)-1-isopropyl-piperidin-3-yl | 2-chlorobenzyl |
| Pyrrolidin-3-yl | 3-chlorobenzyl |
| 2-trifluoromethoxy-benzyl | 4-chlorobenzyl |
| 3-trifluoromethoxy-benzyl | 4-pyrazol-1-yl-benzyl |
| 4-trifluoromethoxy-benzyl | (R)-1-phenyl-ethyl |
| (R)-1-(p-tolyl)-ethyl | (S)-1-phenyl-ethyl |
| (R)-1-(4-Fluoro-phenyl)-ethyl | 2-phenyl-ethyl |
| (2-fluoro-phenyl)-ethyl | (2-methoxy-phenyl)-ethyl |
| (3-fluoro-phenyl)-ethyl | (3-methoxy-phenyl)-ethyl |
| (4-fluoro-phenyl)-ethyl | (4-methoxy-phenyl)-ethyl |
| (2-chloro-phenyl)-ethyl | (R)-1-(2-phenyl-propyl) |
| (3-chloro-phenyl)-ethyl | (S)-1-(2-phenyl-propyl) |
| (4-chloro-phenyl)-ethyl | (R)-1-hydroxymethyl-2-phenylethyl |
| (±)-2-(4-fluoro-phenyl)-1-methyl-ethyl | (S)-1-hydroxymethyl-2-phenylethyl |
| (R)-2-hydroxy-2-phenyl-ethyl | 2-(1H-indol-3-yl)-ethyl |
| (S)-2-hydroxy-2-phenyl-ethyl | indan-2-yl |
| 2-pyridin-2-yl-ethyl | 3-phenyl-propyl |
| 3-pyridin-2-yl-ethyl | 1-(4-Fluoro-phenyl)-ethyl |
| 4-pyridin-2-yl-ethyl | 2-piperidin-1-yl-ethyl |
| 4-benzyloxy-phenyl | trans-4-hydroxy-cyclohexyl |
| tert-butyl | Cyclohexyl |
| (±)-1-BOC-piperidin-3-yl | 2-Diethylamino-ethyl |
| (±)-piperidin-3-yl | (±)-1-(2-hydroxy-ethyl)-piperidin-3-yl |
| (R)-piperidin-3-yl | (±)-1-ethyl-pyrrolidin-2-ylmethyl |
| (S)-piperidin-3-yl | (±)-1-ethyl-pyrrolidin-3-yl |
| 2-dimethylamino-ethyl | 1-aza-bicyclo[2.2.2]oct-2-yl |
| 2-dimethylamino-1-methyl-ethyl | 1-(2,2-difluoro-ethyl)-piperidin-3-yl |
| 2-diisopropylamino-ethyl | 2-dimethylamino-2-phenyl-ethyl |
| (±)-1-benzyl-piperidin-3-yl | (±)-1-propyl-piperidin-3-yl |
| (±)-1-allyl-piperidin-3-yl | (±)-1-isobutyl-piperidin-3-yl |
| (±)-1-acetyl-pipendin-3-yl | |

It should be recognized that the compounds described in the above table where the $R_1$ substituent is varied may each be further substituted by replacing one or more of the hydrogens implicitly depicted in the structure with non-hydrogen substituents. Such further substituents may optionally form additional fused rings, as is also taught herein.

In one variation, $R_1$ is a substituted alkyl where the carbon of $R_1$ alpha to the ring atom is a tertiary carbon, i.e., in addition to the bond to the ring atom, the carbon atom has two non-hydrogen substituents. It is believed that substitution of the carbon alpha to the ring atom in this manner may reduce oxidation of that alpha carbon, particularly when the ring atom is nitrogen, thus adding to the stability of the compound.

Substituents $R_2$, $R_3$, $R_4$, $R_5$, $R_6$, $R_7$, $R_8$ and $R_9$ $R_2$, $R_3$, $R_4$, $R_5$, $R_6$, $R_7$, $R_8$ and $R_9$ may each independently be selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, amino, thio, cyano, nitro, and a carbonyl group, each substituted or unsubstituted.

It is noted that $R_2$ and $R_3$; $R_3$ and $R_4$; and $R_4$ and $R_5$ may each optionally be taken together to form a ring. The ring formed may optionally be a 5 or 6 membered ring. In one variation, the ring formed is an aryl or heteroaryl ring.

It is also noted that $R_6$ and $R_7$; $R_7$ and $R_8$; and $R_8$ and $R_9$ may each optionally be taken together to form a ring. The ring formed may optionally be a 5 or 6 membered ring. In one variation, the ring formed is an aryl or heteroaryl ring.

Substituent Z

Figure 2B:
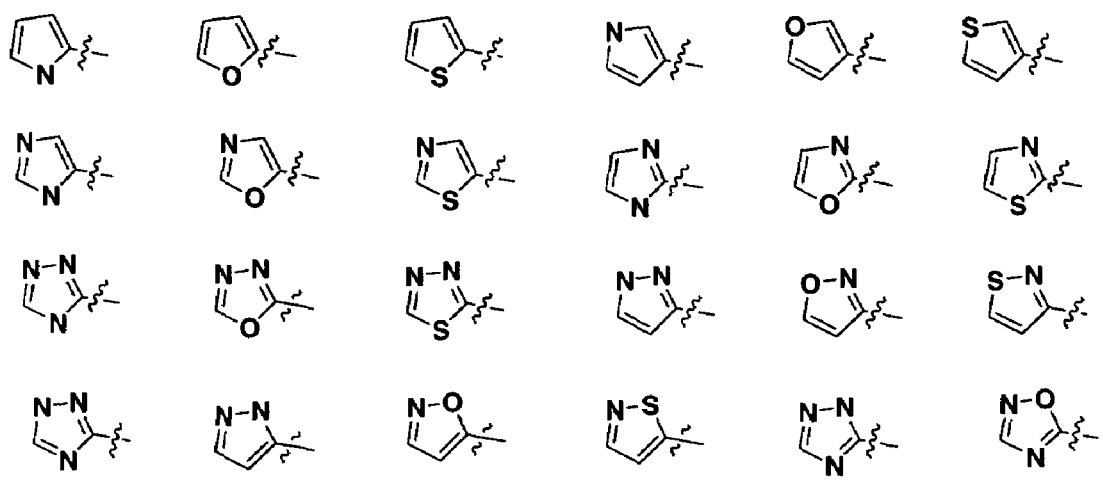
FIG. 2B illustrates particular examples of Z moieties that the compounds of the present invention may comprise.

FIG. 2B illustrates particular examples of Z moieties that the compounds of the present invention may comprise. In one particular embodiment, the Z moiety is a substituted or unsubstituted benzimidazole or imidazole.

It is noted that the examples of Z moieties shown in FIG. 2B may optionally be further substituted as has been specified herein. For example, the various $R_1$ substituents that may be appended to the ring are not specified in FIG. 2B.

Also, it is noted that FIG. 2B is intended only to be exemplary and that other Z substituents may be employed in the compounds according to the present invention consistent with the teachings herein.

Substituent Q

As noted above, Q may be a substituted or unsubstituted aromatic ring. The substituents of the aromatic ring can vary widely and may optionally be such that one or more additional rings are fused to the core aromatic ring of Q.

Q may optionally be a 5 or 6 membered aromatic ring. When Q is a 6 membered aromatic ring, moieties Z and L may be meta or para substituents relative to each other on the 6 membered aromatic ring. In one variation, moieties Z and L are meta substituted relative to each other.

In one variation where Q is a phenyl ring, the phenyl ring may have substituents $R_6$, $R_7$, $R_8$, and $R_9$. As indicated above, these substituents may each optionally be independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, amino, thio, cyano, nitro, and a carbonyl group, each substituted or unsubstituted. It is noted that other substituents may additionally be appended to the phenyl ring without departing from the intended scope of the present invention.

In another variation, Q is a 5 and 6 membered aromatic ring comprising heteroatoms, i.e., a heteroaryl. For example, the heteroaryl ring may optionally have the formula

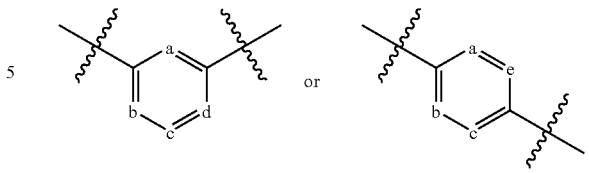

where a, b, c, d and e are each independently nitrogen (N) or carbon (C), with a proviso that when a and c are both nitrogen, then c is carbon. When a, b, c, d and/or e are carbon, the given carbon atom may be substituted. Examples of substituents include, but are not limited to members selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, amino, thio, cyano, nitro, and a carbonyl group, each substituted or unsubstituted. It is noted that other substituents may additionally be appended to the heteroaryl ring without departing from the intended scope of the present invention.

Figure 2C:
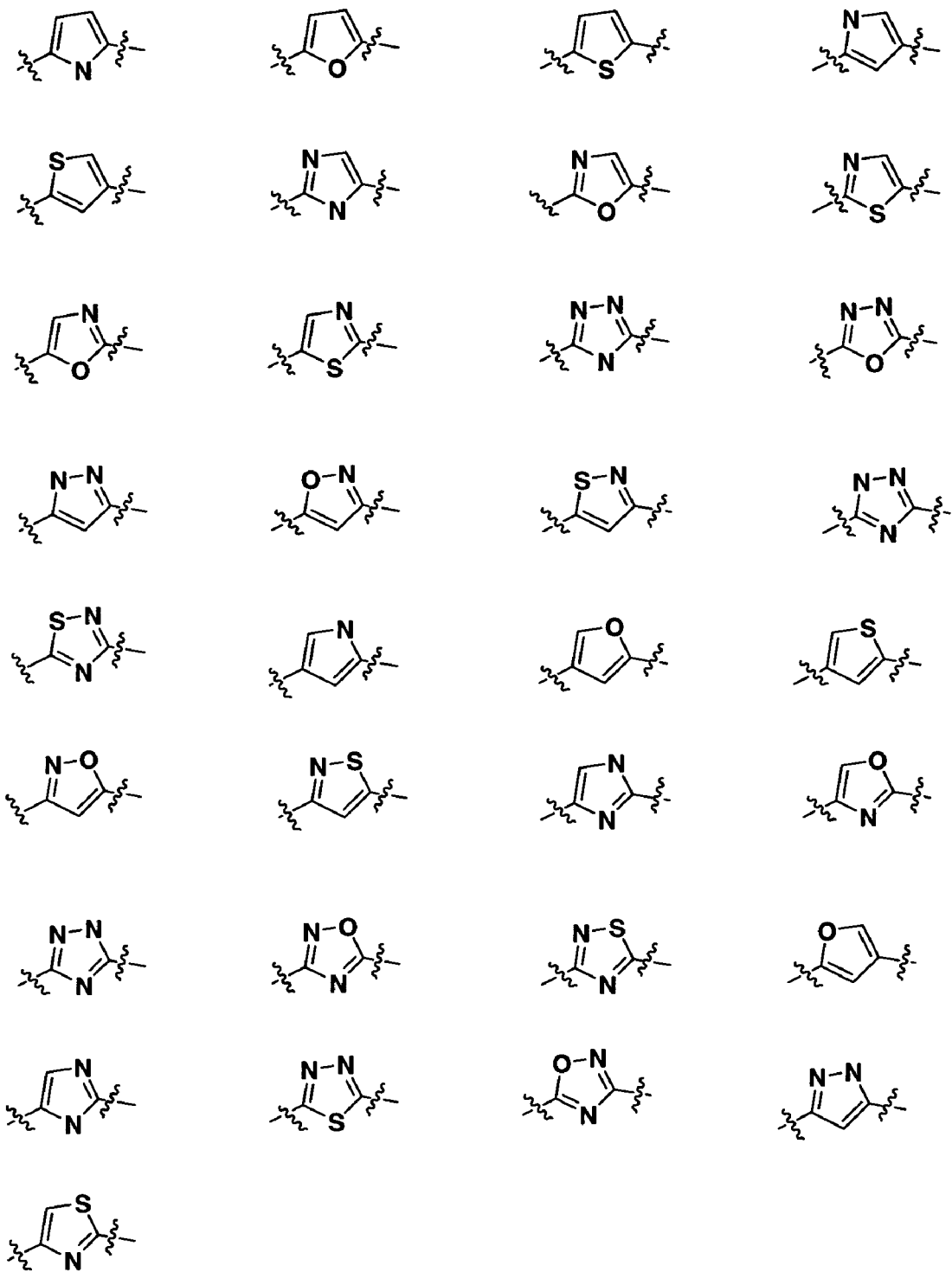
FIG. 2C illustrates examples of moieties, Q, that the leader group may comprise to link the leader group (L) to the remainder of the compound.
Figure 2C:
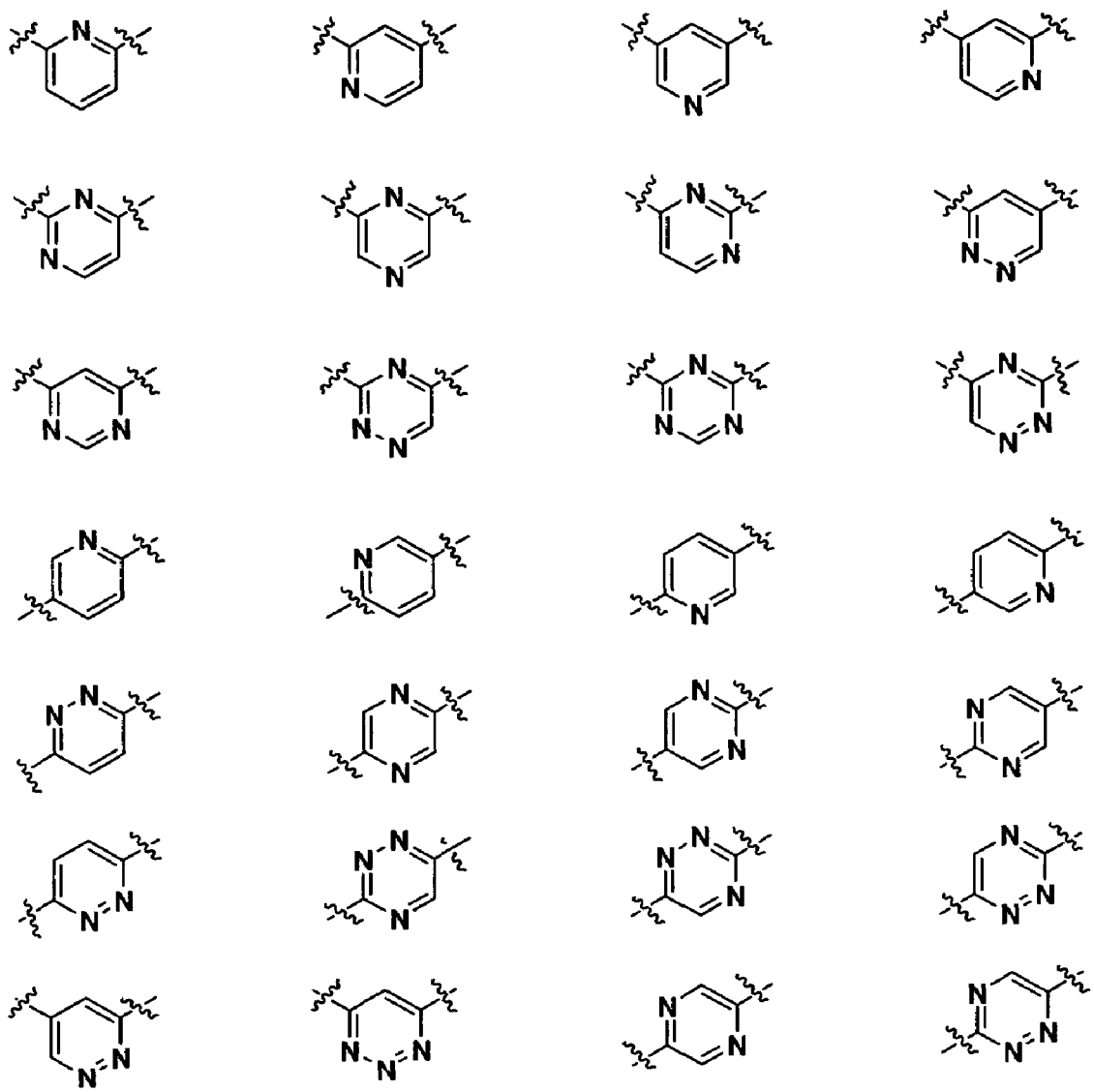

Examples of rings comprising heteroatoms, including 5 and 6 membered aromatic rings comprising heteroatoms are illustrated in FIG. 2C. It is noted that the rings shown in FIG. 2C are unsubstituted and that further substitutions may optionally be added as has been specified.

Further particular examples of rings that may be comprised in the Q substituent include, but are not limited to furan, thiophene, pyrrole, pyrazole, triazole, isoxazole, oxazole, thiazole, isothiazole, oxadiazole, pyridine, pyridazine, pyrimidine, pyrazine, triazine, benzofuran, isobenzofuran, benzothiophene, isobenzothiophene, indole, isobenzazole, quinoline, isoquinoline, cinnoline, quinazoline, naphthyridine, pyridopyridine, quinoxaline, phthalazine, benthiazole, and triazine.

Surprisingly, it was determined that when group Q is a meta substituted aryl or heteroaryl group, the resulting inhibitors show improved biological activities over that of the corresponding para substituted aryl or heteroaryl groups. Preferably, the meta substituted aryl is a meta substituted phenyl moiety that is substituted or unsubstituted. Without being bound by any particular theory, it is believed that the meta substitution serves to direct the zinc complexing substituent M to a more favorable position so as to allow the zinc complexing substituent to interact with the zinc ion while the remainder of the compound maintains its interaction with hydrophobic regions in the binding pocket of the histone deacetylase.

Metal Ion Complexing Substituent, M

In regard to each of the above embodiments, substituent M may be a substituent capable of complexing with a deacetylase catalytic site and/or a metal ion, and optionally more particularly a zinc ion since a zinc ion is known to be present in the catalytic site of deacetylases. Hence, the M substituent may facilitate inhibitor binding by complexing with the zinc ion present in the catalytic site of deacetylases. In one particular variation, M is a substituent capable of complexing with a histone deacetylase catalytic site and/or a metal ion.

Examples of substituents capable of complexing with a zinc ion that may be used as the M substituent include, but are not limited to trifluoroacetyl (—C(O)—CF$_3$), —NH—P(O)OH—CH$_3$, sulfonamides (—SO$_2$NH$_2$), hydroxysulfonamides (—SO$_2$NHOH), thiols (—SH), and carbonyl groups having the formula —C(O)—R$_{13}$ wherein R$_{13}$ is hydroxylamino, hydroxyl, amino, alkylamino, or an alkyloxy group. Particular examples of such substituents include:

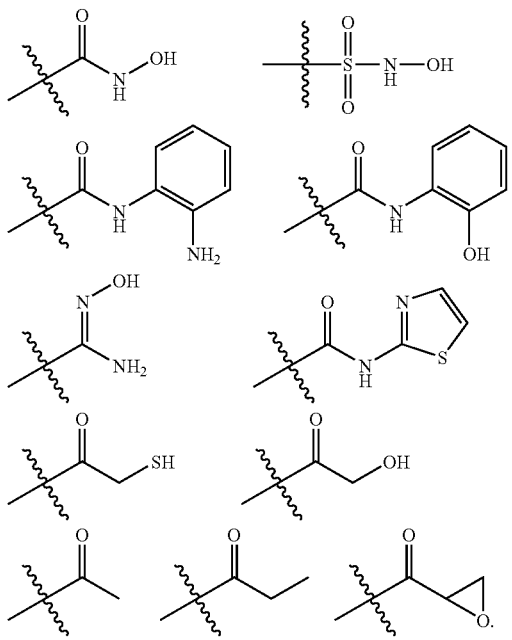

In one particular variation, M is a hydroxamic acid (—C(O)—NHOH), also shown above. It is noted that hydroxamic acids, such as trichostatin A, have been shown to be effective inhibitors against histone deacetylases by complexing with the zinc ion present in the catalytic site of histone deacetylases.

Leader Group, L

In regard to each of the above embodiments, the leader group, L, may be any substituent providing between 0-10 atoms separation between the M substituent and the remainder of the compound. The number of atoms separating the M substituent and the remainder of the compound serves to extend the zinc complexing substituent, M, a sufficient distance away from the remainder of the compound so as to allow the zinc complexing substituent to interact with the zinc ion while the remainder of the compound interacts with hydrophobic regions in the binding pocket of the deacetylase.

In one embodiment, the leader group, L, provides between 1-10 atoms that extend from the M substituent to remainder of the compound, optionally 3-9 and optionally 4-8 atoms. In one variation, the number of atoms separating the M substituent from the remainder of the compound is 3, 4, 5, 6, 7, 8 or 9 atoms.

It is noted that the atoms of the leader group extending between the M substituent and the remainder of the compound may consist only of carbon atoms. Alternatively, the atoms of the leader group extending between the M substituent and the remainder of the compound may also comprise non-carbon atoms such as nitrogen, oxygen and sulfur.

It is also noted that the bonds between the atoms of the leader group extending between the M substituent and the remainder of the compound may be saturated, partially unsaturated, or fully unsaturated. For example, the leader group may comprise one or more alkene (—CH═CH—) or alkyne (—C≡C—) bonds.

Figure 2D:
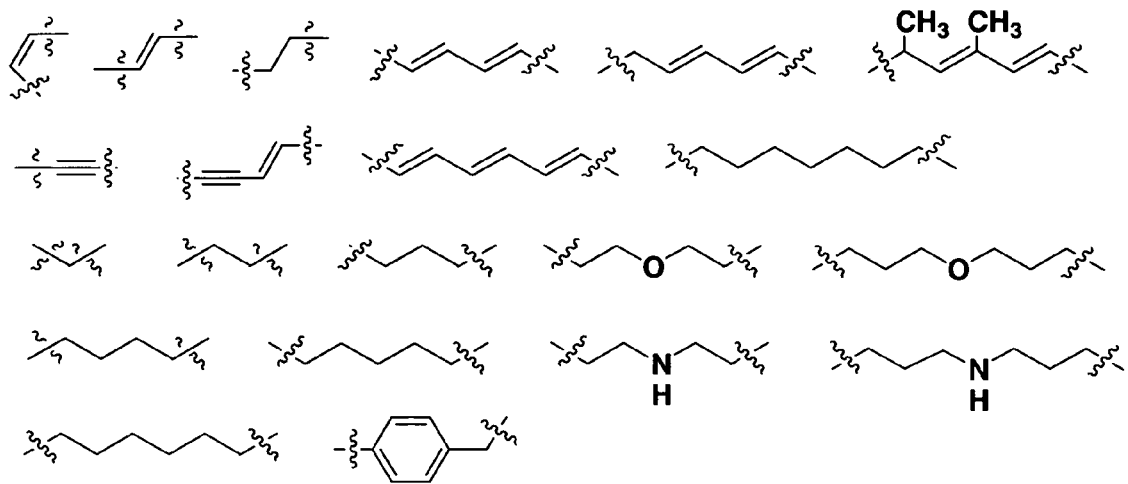
FIG. 2D illustrates particular examples of moieties that the leader groups may comprise.

A variety of different moieties may be incorporated into the leader groups of the HDAC inhibitors of the present invention. Examples of such moieties are shown in FIG. 2D.

The atoms forming the backbone of the leader group, L, may optionally comprise one or more members of the group consisting of: —(CH$_2$)n—, where n is an integer from 1 to 10; —CH(CH$_3$)—; —CH(CH$_3$)CH$_2$— and —CH$_2$CH (CH$_3$)—; —CH(CH$_3$)CH$_2$CH$_2$—, —CH$_2$CH(CH$_3$)CH$_2$—, and —CH$_2$CH$_2$CH (CH$_3$)—; —CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, and —CH$_2$CH$_2$CH$_2$CH(CH$_3$)—; —CH(CH$_3$)CH$_2$CH$_2$CHCH$_2$—, —CH$_2$CH(CH$_3$)CH$_2$CH$_2$CH$_2$—, —CH$_2$CH$_2$CH(CH$_3$)CH$_2$CH$_2$—, —CH$_2$CH$_2$CH$_2$CH(CH$_3$) CH$_2$—, and —CH$_2$CH$_2$CH$_2$CH$_2$CH(CH$_3$)—; —CH (CH$_2$CH$_3$)—; —CH(CH$_2$CH$_3$)CH$_2$— and —CH$_2$CH (CH$_2$CH$_3$)—; —CH(CH$_2$CH$_3$)CH$_2$CH$_2$—, —CH$_2$CH (CH$_2$CH$_3$)CH$_2$—, and —CH$_2$CH$_2$CH(CH$_2$CH$_3$)—; —CH (CH$_2$CH$_3$)CH$_2$CH$_2$CH$_2$—, —CH$_2$CH(CH$_2$CH$_3$) CH$_2$CH$_2$—, —CH$_2$CH$_2$CH(CH$_2$CH$_3$)CH$_2$—, and —CH$_2$CH$_2$CH$_2$CH(CH$_2$CH$_3$)—; —CH$_2$CH$_2$CH(CH$_2$CH$_3$) CH$_2$CH$_2$—, —CH$_2$CH$_2$CH(CH$_2$CH$_3$)CH$_2$—, and —CH(CH$_2$CH$_3$)CH$_2$CH$_2$CH$_2$CH$_2$—, —CH$_2$CH(CH$_2$CH$_3$) CH$_2$CH$_2$CH$_2$—, —CH$_2$CH$_2$CH$_2$CHCH(CH$_2$CH$_3$); —CH═CH—; —CH═CHCH$_2$— and —CH$_2$CH═CH—; —CH═CHCHCH$_2$—, —CH$_2$CH═CHCH$_2$—, and —CH$_2$CH$_2$CH═CH—; —CH═CHCH$_2$CH$_2$CH$_2$—, —CH$_2$CH═CHCH$_2$CH$_2$—, —CH$_2$CH$_2$CH═CHCH$_2$—, and —H$_2$CH$_2$CH$_2$CH═CH—; —CH═CHCHCH$_2$CH$_2$CH$_2$—, —CH$_2$CH═CHCH$_2$CH$_2$CH$_2$—, —CH$_2$CH$_2$CH═CHCH$_2$CH$_2$—, —CH$_2$CH$_2$CH$_2$CH═CHCH$_2$—, and —CH$_2$CH$_2$CH$_2$CHCH═CH—; —C(CH$_3$)═CH— and —CH═C(CH$_3$)—; —C(CH$_3$)═CHCH$_2$—, —CH═C (CH$_3$)CH$_2$—, and —CH═CHCH(CH$_3$)—; —CH(CH$_3$) CH═CH—, —CH$_2$C(CH$_3$)═CH—, and —CH$_2$CH═C (CH$_3$)—; —CH═CHCH═CH—; —CH═CHCH═CHCH$_2$—, —CH$_2$CH═CHCH═CH—, and —CH═CHCH$_2$CH═CH—; —CH═CHCH═CHCH$_2$CH$_2$—, —CH═CHCH$_2$CH═CHCH$_2$—, and —CH═CHCH$_2$CH$_2$CH═CH—, —CH$_2$CH═CHCH═CHCH$_2$—, —CH$_2$CH═CHCH$_2$CH═CH—, and —CH$_2$CH$_2$CH═CHCH═CH—; —C(CH$_3$) ═CHCH═CH—, —CH═C(CH$_3$)CH═CH—, —CH═CHC(CH$_3$)═CH—, and —CH═CHCH═C (CH$_3$)—; —C≡C—; —C≡CCH$_2$—, —CH$_2$C≡C—; —C≡CCH(CH$_3$)—, and —CH(CH$_3$)C≡C—; —C≡CCH$_2$CH$_2$—, —CH$_2$C—CCH$_2$—, and —CH$_2$CH$_2$C≡C—; —C≡CCH(CH$_3$)CH$_2$— and —C≡CCH$_2$CH(CH$_3$)—; —CH(CH$_3$)C≡CCH$_2$— and —CH$_2$C≡CCH(CH$_3$)—; —CH(CH$_3$)CH$_2$C≡C— and —CH$_2$CH(CH$_3$)C≡C—; —C≡CCH═CH—, —CH═CHC≡C—, and —C≡CC≡C—; —C≡CCH$_2$CH$_2$CH$_2$— and —CH$_2$CH$_2$CH$_2$C≡C—; —C—CCH$_2$CH$_2$CH$_2$— and —CH$_2$CH$_2$CH$_2$CH$_2$C≡C—; —C≡CCH═CHCH—, —CH═CHC≡C— CH═CH—, and —CH═CHCH═CHC≡C—; —C(CH$_3$) ═CHC≡C—, —CH═C(CH$_3$)C≡C—, —C≡CC(CH$_3$) ═CH—, and —C≡CCH═C(CH$_3$). L may also be E, Z or mixtures of E/Z —CH$_2$═CH$_2$—. It is noted that the hydrogen atoms of above possible portions of the leader group may optionally be substituted with further substituents.

It is also noted that the leader group may comprise one or more substituents extending from one or more atoms of the leader group backbone. In one variation, two substituents extending from the atoms extending between the carbon alpha to the leader group and the M substituent to form one or more three, four, five, six, seven, eight or nine membered rings. The atoms of the leader group forming the ring may be separated from each other by 0, 1, 2, 3, or 4 atoms.

The rings may be saturated or partially unsaturated (i.e., comprise one or two double bonds). The rings may also be aromatic, referred to herein as aryl and heteroaryl rings. The rings may optionally be further substituted. These further ring substituents may combine to form additional rings that are fused to the rings forming a portion of the backbone, e.g., bicycloaryl and bicycloheteroaryl.

Examples of cycloalkyl rings that may be formed by one or more leader group backbone atoms include, but are not limited to: cyclopropyl, cyclohexane, cyclopentane, cyclopentene, cyclopentadiene, cyclohexane, cyclohexene, cyclohexadiene, phenyl, cycloheptane, cycloheptene, cycloheptadiene, cyclooctane, cyclooctene, and cyclooctadiene.

Examples of heteroaryl rings that may be formed by one or more leader group backbone atoms include, but are not limited to: furan, thiofuran, pyrrole, isopyrrole, 3-isopyrrole, pyrazole, isoimidazole, triazole, isoxazole, oxazole, thiazole, isothiazole, oxadiazole, pyridine, pyridazine, pyrimidine, pyrazine, triazine, benzofuran, isobenzofuran, benzothiofuran, isobenzothiophene, indole, isobenzazole, quinoline, isoquinoline, cinnoline, quinazoline, naphthyridine, and pyridopyridine.

It is noted that the inhibitors may include one or more chiral centers. The chiral centers may be either the R or S enantiomers, depending on the substituents.

Synthetic scheme for synthesizing compounds according to these various embodiments are provided in the Examples. Particular examples of HDAC inhibitors according to these embodiments are provided in the examples.

A. Salts, Hydrates, and Prodrugs of HDAC Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl- and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, benzenesulfonate (besylate), bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, ethanesulfonate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free acid forms will typically differ from their respective salt forms somewhat in physical properties such as solubility in polar solvents, but otherwise the salts are equivalent to their respective free acid forms for the purposes of the present invention.

When the compounds of the present invention possess a free base form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N, N'-dibenzyl-ethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free base forms will typically differ from their respective salt forms somewhat in physical properties such as solubility in polar solvents, but otherwise the salts are equivalent to their respective free base forms for the purposes of the present invention.

Compounds of the present invention, which comprise basic nitrogen-containing groups, may be quaternized with such agents as ($C_{1-4}$) alkyl halides, e.g., methyl, ethyl, iso-propyl and tert-butyl chlorides, bromides and iodides; di($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, *Protecting Groups in Organic Synthesis*, $3^{rd}$ edition, John Wiley & Sons, Inc. 1999.

Compounds of the present invention may also be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxane, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid adsorption of the compound.

3. Preparation of HDAC Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

4. Indications for Use of HDAC Inhibitors

HDAC is believed to contribute to the pathology and/or symptomology of several different diseases such that reduction of the activity of HDAC in a subject through inhibition may be used to therapeutically address these disease states. Examples of various diseases that may be treated using the HDAC inhibitors of the present invention are described herein. It is noted that additional diseases beyond those disclosed herein may be later identified as the biological roles that HDAC play in various pathways becomes more fully understood.

A. Undesirable or Uncontrolled Cell Proliferation

One set of indications that HDAC inhibitors of the present invention may be used to treat are those involving undesirable or uncontrolled cell proliferation. Such indications include benign tumors, various types of cancers such as primary tumors and tumor metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta.-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-(2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumors retain their differentiated features and do not divide in a completely uncontrolled manner. A benign tumor is usually localized and nonmetastatic. Specific types of benign tumors that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumors, or metastases, are tumors that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumors, either primary or secondary, that can be treated using the HDAC inhibitors of the present invention include, but are not limited to, leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome. An example of a cell proliferative disorder that may be treated using the invention is a bone tumor.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of retinal/choroidal neovascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, *Mycobacteria* infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angionesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation and provide the RA patient relief from the symptoms.

5. Compositions Comprising HDAC Inhibitors

A wide variety of compositions and administration methods may be used in conjunction with the HDAC inhibitors of the present invention. Such compositions may include, in addition to the HDAC inhibitors of the present invention, conventional pharmaceutical excipients, and other conventional, pharmaceutically inactive agents. Additionally, the compositions may include active agents in addition to the HDAC inhibitors of the present invention. These additional active agents may include additional compounds according to the invention, or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising HDAC inhibitors of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The HDAC inhibitors and compositions comprising them may be administered or coadministered in any conventional dosage form. Coadministration in the context of this invention is intended to mean the administration of more than one therapeutic agents, one of which includes a HDAC inhibitor, in the course of a coordinated treatment to achieve an improved clinical outcome. Such coadministration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When HDAC inhibitors according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding HDAC inhibitors according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more HDAC inhibitors according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington: The Science and Practice of Pharmacy, A. Gennaro, ed., 20th edition, Lippincott, Williams & Wilkins, Philadelphia, Pa., 2000. The composition or formulation to be administered will, in any event, contain a sufficient quantity of a HDAC inhibitor of the present invention to reduce HDAC activity in vivo, thereby treating the disease state of the subject.

Dosage forms or compositions may optionally comprise one or more HDAC inhibitors according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more HDAC inhibitors, optionally 0.1-95%, and optionally 1-95%.

Salts, preferably sodium salts, of the HDAC inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, HDAC inhibitors according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric-coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The HDAC inhibitors of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising HDAC inhibitors of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that maybe used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic adds and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, egg., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

B. Injectables, Solutions and Emulsions

The present invention is also directed to compositions designed to administer the HDAC inhibitors of the present invention by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Example of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (Tween 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of a HDAC inhibitor in the parenteral formulation may be adjusted so that an injection administers a pharmaceutically effective amount sufficient to produce the desired pharmacological effect. The exact concentration of a HDAC inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the HDAC inhibitor to the treated tissue(s). The HDAC inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The HDAC inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The HDAC inhibitors of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the sodium salt in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a HDAC inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the HDAC inhibitor.

D. Topical Administration

The HDAC inhibitors of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The HDAC inhibitors may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically diameters of less than 50 microns, preferably less than 10 microns.

The HDAC inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the HDAC inhibitor alone or in combination with other pharmaceutically acceptable excipients can also be administered.

E. Formulations for Other Routes of Administration

Depending upon the disease state being treated, other routes of administration, such as topical application, transdermal patches, a rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10–100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

6. Kits Comprising HDAC Inhibitors

The invention is also directed to kits and other articles of manufacture for treating diseases associated with HDAC. It is noted that diseases are intended to cover all conditions for which the HDAC possesses activity that contributes to the pathology and/or symptomology of the condition.

In one embodiment, a kit is provided that comprises a composition comprising at least one HDAC inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one HDAC inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

7. Combination Therapy

A wide variety therapeutic agents may have a therapeutic additive or synergistic effect with HDAC inhibitors according to the present invention. Such therapeutic agents may additively or synergistically combine with the HDAC inhibitors to inhibit undesirable cell growth, such as inappropriate cell growth resulting in undesirable benign conditions or tumor growth.

In one embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of therapeutic agents that may be used in combination with HDAC inhibitors include, but are not limited to, anticancer agents, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including a HDAC inhibitor and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including a HDAC inhibitor and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a HDAC inhibitor and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including a HDAC inhibitor and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a HDAC inhibitor and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a HDAC inhibitor and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with HDAC inhibitor include, but are not limited to, interleukin 2 (IL-2), and interleukin 4 (IL-4), interleukin 12 (IL-12).

Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with a HDAC inhibitor include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with a HDAC inhibitor to reduce chemotherapy-induced myelopoietic toxicity.

Other immuno-modulating agents other than cytokines may also be used in conjunction with a HDAC inhibitor to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including HDAC inhibitor and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20$^+$ pre-B and mature B cells. RITUXAN® is used as single agent for the treatment of patients with relapsed or refractory low-grade or follicular, CD20+, B cell non-Hodgkin's lymphoma. Combination therapy including HDAC inhibitor and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilm's tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including a HDAC inhibitor and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp 100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

8. HDAC Activity Assay

Compounds according to the present invention may be screened for activity against one or more HDACs. Provided in this example are assays for activity against HDAC1, HDAC2, HDAC6 and HDAC8.

Purified HDAC 1, HDAC2, HDAC6, and HDAC8 may be obtained as follows.

For HDAC1, DNA encoding residues 1-482 of the full-length sequence of the human enzyme may be amplified by PCR and cloned into the BamHI/XbaI sites of pFastbac (Invitrogen), which incorporates a 6-histidine tag at the N-terminus. SEQ. I.D. No. 1 corresponds to residues 1-482 with the N-terminal 6-histidine tag and SEQ. I.D. No. 2 is the DNA sequence that was used to encode SEQ. I.D. No. 1.

For HDAC2, DNA encoding residues 1-488 of the full-length sequence of the human enzyme may be amplified by PCR and cloned into the BamHI/SmaI sites of pFastbac (Invitrogen), which incorporates a 6-histidine tag at the C-terminus. SEQ. I.D. No. 3 corresponds to residues 1-488 with the C-terminal 6-histidine tag and SEQ. I.D. No. 4 is the DNA sequence that was used to encode SEQ. I.D. No. 3.

For HDAC6, DNA encoding residues 73-845 of the human enzyme may be amplified by PCR and cloned into the SmaI site of pFastbac (Invitrogen), which incorporates a 6× Histidine tag at the C-terminus. SEQ. I.D. No. 5 corresponds to residues 73-845 with the C-terminal 6-histidine tag and SEQ. I.D. No. 6 is the DNA sequence that was used to encode SEQ. I.D. No. 5.

For HDAC8, DNA encoding residues 1-377 corresponding to the entire sequence of the human enzyme may be amplified by PCR and cloned into the BamHI/SmaI sites of pFastbac (Invitrogen), which incorporates a 6-histidine tag at the N-terminus. SEQ. I.D. No. 7 corresponds to residues 1-377 with the N-terminal 6-histidine tag and SEQ. I.D. No. 8 is the DNA sequence that was used to encode SEQ. I.D. No. 7.

Recombinant baculovirus incorporating the HDAC constructs may be generated by transposition using the Bac-to-Bac system (Invitrogen). High-titer viral stocks may be generated by infection of Spodoptera frugiperda Sf9 cells; the expression of recombinant protein may be carried out by infection of Spodoptera frugiperda Sf9 or Trichoplusia ni Hi5 cells (Invitrogen) in 10L Wave Bioreactors (Wave Biotech).

Recombinant protein may be isolated from cellular extracts by passage over ProBond resin (Invitrogen). HDAC1 and HDAC6 may then be treated with TEV protease for the removal of the N-terminal 6× Histidine affinity tag (residual uncleaved protein may be removed through a second passage over Probond Resin). Partially purified extracts of all HDACs may then be further purified by high pressure liquid chromatography over a BioSep S3000 gel filtration resin. The purity of HDAC proteins may be determined on denaturing SDS-PAGE gel. Purified HDACs may then be concentrated to a final concentration of 4.0 mg/ml for HDAC 1, 10 mg/ml for HDAC2, 4.0 mg/ml for HDAC6, and 3 mg/ml for HDAC8. The proteins may be either stored at −78° C. in a buffer containing 25 mM TRIS-HCl pH 7.6, 150 mM NaCl, 0.1 mM EDTA and 0.25 mM TCEP or at −20° C. in the presence of glycerol (final concentration of glycerol at 50%)

The inhibitory properties of compounds relative to HDAC1, HDAC2, HDAC6 and HDAC8 may be determined using a white or black 384-well-plate format under the following reaction conditions: 25 mM Tris pH 8.0, 100 mM NaCl, 50 mM KCl, 0.1 mM EDTA, 0.01% Brij35, 0.1 mM TCEP. 50 uM tBoc-Lys(Ac)-AMC, 2% DMSO. Reaction product may be determined quantitatively by fluorescence intensity using a Fluorescence plate reader (Molecular Devices Gemini) with an excitation wavelength at 370 nm and emission at 480 nm (for white plates) or 465 nm (for black plates).

The assay reaction may be initiated as follows: 5 ul of 150 uM tBoc-Lys(Ac)AMC was added to each well of the plate, followed by the addition of 5 ul of inhibitor (2 fold serial dilutions for 11 data points for each inhibitor) containing 6% DMSO. 5 ul of either HDAC1, HDAC2, HDAC6 or HDAC8 solution may be added to initiate the reaction (final enzyme concentrations were 2.5 nM for HDAC1, 1 nM for HDAC2, 2.5 nM for HDAC6 and 10 nM for HDAC8). The reaction mixture may then be incubated at room temperature for 60 min, and quenched and developed by addition of 5 ul of 10 mM phenanthroline and 4 mg/ml trypsin (final concentration of phenanthroline is 2.5 mM, and trypsin is 1 mg/ml).

Fluorescence intensities of the resulting reaction mixtures may be measured after a 30 minute incubation at room temperature.

IC50 values may be calculated by non-linear curve fitting of the compound concentrations and fluorescence intensities to the standard IC50 equation. As a reference point for this assay, suberanilohydroxamic acid (SAHA) showed an IC50 of 63 nM for HDAC1, 69 nM for HDAC2, 108 nM for HDAC6 and 242 nM for HDAC8.

The Section below provides examples of HDAC inhibitors that were assayed according to the above assays and found to have better than 1000 nM activity against HDAC1, HDAC2, HDAC6, and HDAC8.

EXAMPLES

1. Synthetic Schemes for HDAC Inhibitors

HDAC inhibitors according to the present invention may be synthesized according to a variety of reaction schemes. Some illustrative schemes are provided herein in the examples. Other reaction schemes could be readily devised by those skilled in the art.

Scheme 1:

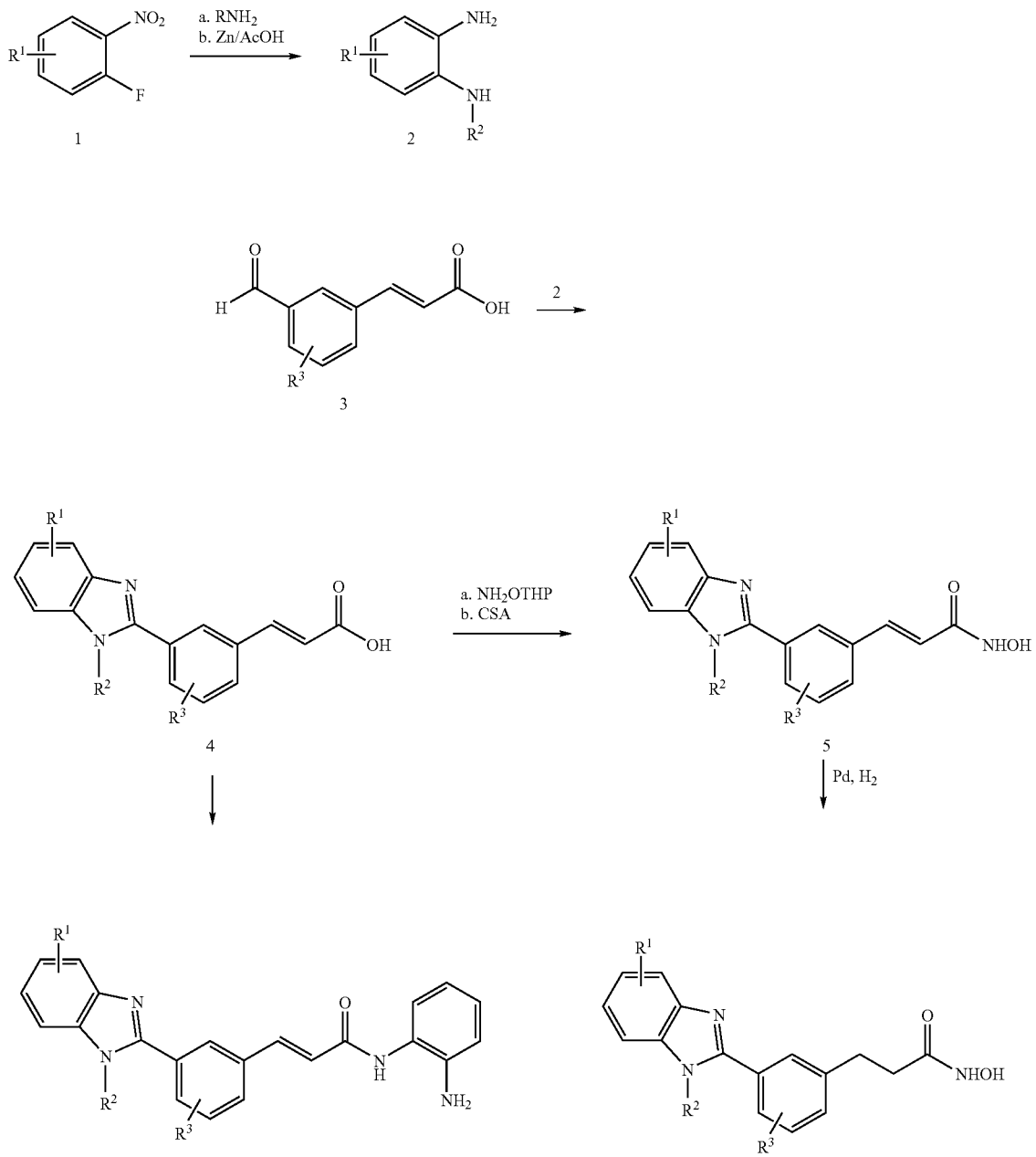

Scheme 2:

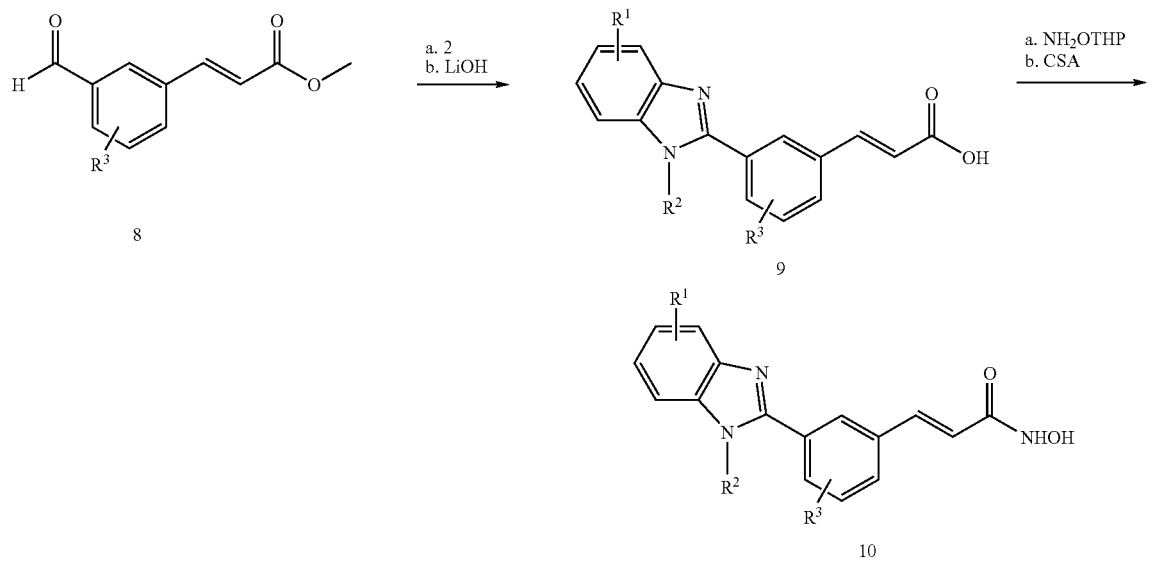

General Procedure for the Synthesis of N¹-substituted-phenyl-1,2-diamines (2).

To a solution of the appropriate 1-fluoro-2-nitrobenzene (1, 1.77 mmol) and the appropriate amine (1.77 mmol) in DMF (5.0 mL) was added DIEA (1.94 mmol). The reaction was heated at 50-100° C. for 24-48 hrs and then cooled to ambient temperature. The resulting mixture was poured into $H_2O$, extracted with EtOAc, washed with brine, and dried over $MgSO_4$. The organic layer was evaporated to dryness and the resulting material was purified if needed via flash chromatography to yield the desired 2-nitrophenylamines. The appropriate N-substituted-2-nitrophenylamine (1.10 mmol) was dissolved in MeOH/AcOH (4:1, 5.0 mL) and heated to 100° C. Zinc dust (5.50 mmol) was added to the reaction portion wise until frothing ceased. The reaction was cooled to ambient temperature, filtered, and evaporated to dryness. The resulting N¹-substituted-phenyl-1,2-diamine (2) was used without further purification.

General Procedure for the Synthesis of 3-[3-(1-substituted-1H-benzoimidazol-2-yl)-phenyl]-acrylic acids (4).

A solution of the appropriate 3-formyl-cinnamic acid (3, 0.57 mmol) and the appropriate N¹-substituted-phenyl-1,2-diamine (2, 0.57 mmol) in EtOH (5.0 mL) was refluxed for 24-48 hrs. The reaction was cooled, evaporated to dryness and purified via flash chromatography to yield the desired 3-[3-(1-substituted-1H-benzoimidazol-2-yl)-phenyl]-acrylic acid (4).

General Procedure for the Synthesis of N-hydroxy-3-[3-(1-substituted-1H-benzoimidazol-2-yl)-phenyl]-acrylamides (5).

To a solution of the appropriate 3-[3-(1-substituted-1H-benzoimidazol-2-yl)-phenyl]-acrylic acid (4, 0.25 mmol), and HOBt (0.38 mmol) in DMF (5.0 mL) was added EDCI (0.38 mmol), O-(tetrahydro-pyran-2-yl)-hydroxylamine (0.38 mmol), and DIEA (0.75 mmol). The reaction was stirred at ambient temperature for 18 hrs. The resulting mixture was poured into $H_2O$, extracted with EtOAc, washed with brine, and dried over $MgSO_4$. The organic layer was evaporated to dryness and the resulting material was reconstituted in MeOH (2 mL). CSA (0.28 mmol) was added to the solution. The reaction was stirred for 2 hr at ambient temperature and, without further work-up, purified by preparative LCMS to yield the desired N-hydroxy-3-[3-(1-substituted-1H-benzoimidazol-2-yl)-phenyl]-acrylamide (5).

General Procedure for the Synthesis of N-(2-amino-phenyl)-3-[3-(1-substituted-1H-benzoimidazol-2-yl)-phenyl]-acrylamide (6).

To a solution of the appropriate 3-[3-(1-substituted-1H-benzoimidazol-2-yl)-phenyl]-acrylic acid (5, 0.25 mmol), and HOBt (0.38 mmol) in DMF (5.0 mL) was added EDCI (0.38 mmol), 1,2-phenylenediamine (0.38 mmol), and DIEA (0.75 mmol). The reaction was stirred at ambient temperature for 18 hrs. The resulting mixture was poured into $H_2O$, extracted with EtOAc, washed with brine, and dried over $MgSO_4$. The organic layer was evaporated to dryness, and the resulting material was reconstituted in MeOH (2 mL) and purified by preparative LCMS to yield the desired N-(2-amino-phenyl)-3-[3-(11-substituted-1H-benzoimidazol-2-yl)-phenyl]-acrylamide (6).

General Procedure for the Synthesis of N-hydroxy-3-[3-(1-substituted-1H-benzoimidazol-2-yl)-phenyl]-propionamides (7).

To a solution of the appropriate N-hydroxy-3-[3-(1-substituted-1H-benzoimidazol-2-yl)-phenyl]-acrylamide (6; 0.65 mmol) in MeOH (1.0 mL) was added Pd/C (10%; 2.5 mg). $H_2(g)$ was bubbled through the stirring reaction for 1 hr. The reaction was filtered through Celite and purified via preparative LCMS to provide the desired N-hydroxy-3-[3-(1-substituted-1H-benzoimidazol-2-yl)-phenyl]-propionamide (7).

General Procedure for the Synthesis of 3-[3-(1-substituted-1H-benzoimidazol-2-yl)-phenyl]-acrylic acids (9).

A solution of the appropriate 3-formyl-cinnamic acid methyl ester (8, 0.75 mmol) and the appropriate N'-substituted-phenyl-1,2-diamine (2, 0.75 mmol) in ethanol (2.0 mL) was heated at 80° C. for 24-48 hrs. The reaction was cooled, evaporated to dryness and purified via flash chromatography to yield the desired acrylic acid esters. To a solution of the appropriate acrylic acid methyl ester (0.50 mmol) in MeOH (1.0 mL) was added LiOH (1.0 mmol). The reaction was stirred at ambient temperature for 2 hrs and, poured into H₂O, and acidified to pH=2 with HCl (6N). The resulting heterogeneous mixture was then extracted with EtOAc. The organic layers were combined, washed with brine, dried over MgSO₄, filtered, and evaporated to dryness to provide the appropriate 3-[3-(1-substituted-1H-benzoimidazol-2-yl)-phenyl]-acrylic acid (9) which were used in subsequent reactions without further purification.

General Procedure for the Synthesis of 3-[3-(1-substituted-1H-benzoimidazol-2-yl)-phenyl]-N-hydroxyacrylamides (10).

The procedure for the synthesis of N-hydroxy-3-[3-(1-substituted-1H-benzoimidazol-2-yl)-phenyl]-acrylamides (5) was used.

General Procedure for the Synthesis of 3-[3-(1H-benzoimidazol-2-yl)-phenyl]-N-(tetrahydro-pyran-2-yloxy)-acrylamides (11).

A solution of the appropriate 3-formyl-cinnamic acid (3, 0.57 mmol) and the appropriate substituted-phenyl-1,2-diamine (0.57 mmol) in EtOH (5.0 mL) was refluxed for 24 hrs. The reaction was cooled, evaporated to dryness, and the resulting acrylic acid was used without further purification. To a solution of the acrylic acid (0.25 mmol) and HOBt (0.38 mmol) in DMF (5.0 mL) was added EDCI (0.38 mmol), O-(tetrahydro-pyran-2-yl)-hydroxylamine (0.38 mmol), and DIEA (0.75 mmol). The reaction was stirred at ambient temperature for 18 hrs. The resulting mixture was poured into H₂O, extracted with EtOAc, washed with brine, dried over MgSO₄ and concentrated to dryness. The resulting material was purified via flash chromatography to yield the desired 3-[3-(1H-benzoimidazol-2-yl)-phenyl]-N-(tetrahydro-pyran-2-yloxy)-acrylamide (11).

Scheme 3:

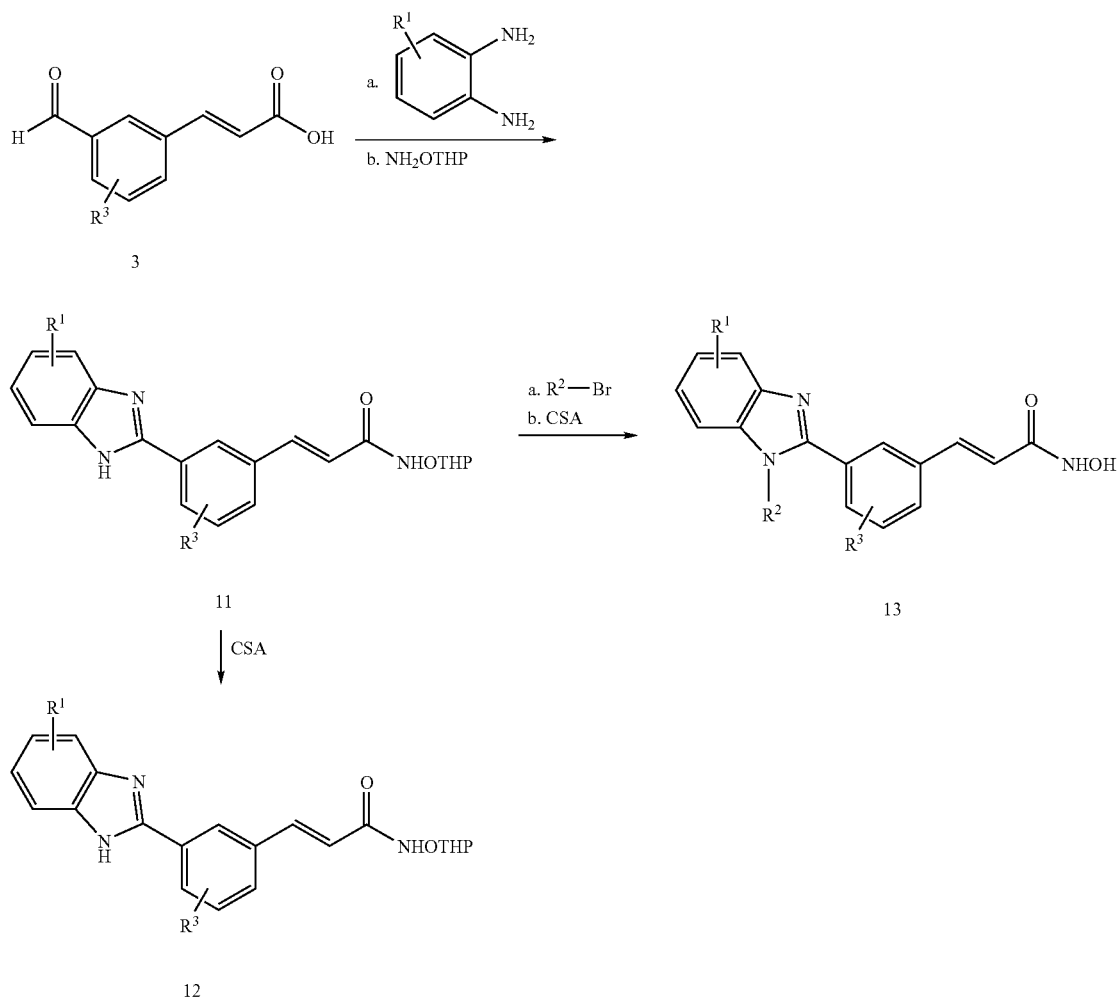

General Procedure for the Synthesis of 3-[3-(1H-benzoimidazol-2-yl)-phenyl]-N-hydroxy-acrylamide (12)

To a solution of the appropriate 3-[3-(1H-benzoimidazol-2-yl)-phenyl]-N-(tetrahydro-pyran-2-yloxy)-acrylamide (11, 0.25 mmol) in MeOH (2 mL) was added CSA (0.28 mmol). The reaction was stirred for 2 hr at ambient temperature and, without further work-up, purified by preparative LCMS to yield the desired 3-[3-(1H-benzoimidazol-2-yl)-phenyl]-N-hydroxy-acrylamide (12).

General Procedure for the Synthesis of N-hydroxy-3-[3-(1-substituted-1H-benzoimidazol-2-yl)-phenyl]-acrylamides (13).

To a solution of NaH (20 mg, 0.83 mmol) in anhydrous DMF (1 mL) was added a solution of 3-[3-(1H-benzoimidazol-2-yl)-phenyl]-N-(tetrahydro-pyran-2-yloxy)-acrylamide (11, 0.28 mmol) in anhydrous DMF drop wise at ambient temperature. The reaction was stirred for 30 min and then the appropriate alkyl bromide (0.31 mmol) was added. The reaction was stirred for 30 min, quenched with MeOH (200 µL) and partitioned between H$_2$O and EtOAc. The organic layer was washed with brine, dried with MgSO$_4$, and evaporated to dryness. The resulting material was reconstituted in MeOH (2 mL). CSA (0.31 mmol) was added to the solution. The reaction was stirred for 2 hr at ambient temperature and, without further work-up, purified by preparative LCMS to yield the desired N-hydroxy-3-[3-(1-substituted-1H-benzoimidazol-2-yl)-phenyl]-acrylamide (13).

As can be seen from the above reaction schemes, a wide variety of different HDAC inhibitors can be synthesized by these reaction schemes. It is noted that the invention is not intended to be limited to the particular compounds provided in this example. Rather, a wide variety of other compounds according to the present invention having HDAC inhibitory activity may be synthesized by the reaction schemes provided as well as other reaction schemes that may be devised by one of ordinary skill in the art in view of the present teachings.

2. Examples of Inhibitors According to the Present Invention

Provided in this example are particular compounds that have been found to have HDAC8 activity based on the assay provided in Example 2. It is noted that these compounds may also have activity relative to other HDACs. It is also noted that these compounds are intended to illustrate various HDAC inhibitors according to the present invention and the present invention is not intended to be limited to these compounds:

COMPOUND 1

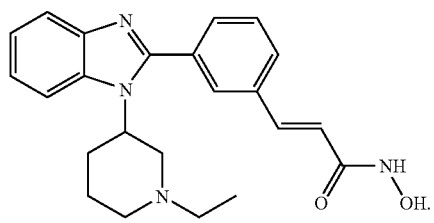

(±)-3-{3-[1-(1-Ethyl-piperidin-3-yl)-1H-benzoimidazol-2-yl]-phenyl}-N-hydroxy-acrylamide $^1$H NMR (400 MHz, DMSO-d$_6$): δ 1.21 (t, 3H), 1.76 (m, 1H), 2.23 (m, 1H), 3.23 (m, 4H), 3.52 (m, 1H), 3.77 (m, 2H), 4.79 (m, 1H), 6.60 (d, 1H), 7.41 (m, 2H), 7.54-7.91 (band, 6H), 8.14 (m, 1H), 9.68 (s, 1H). ESI-MS: m/z 391.2 (M+H)$^+$.

COMPOUND 2

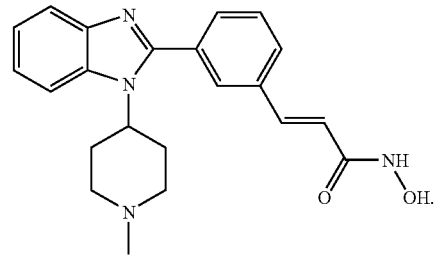

N-Hydroxy-3-{3-[1-(1-methyl-piperidin-4-yl)-1H-benzoimidazol-2-yl]-phenyl}-acrylamide $^1$H NMR (400 MHz, DMSO-d$_6$): δ2.27 (m, 2H), 2.80 (m, 5H), 3.20 (m, 2H), 3.57 (m, 2H), 4.70 (m, 1H), 6.60 (d, 1H), 7.45 (m, 2H), 7.60-7.95 (band, 6H), 8.14 (m, 1H), 10.07 (s, 1H). ESI-MS: m/z 377.1 (M+H)$^+$.

COMPOUND 3

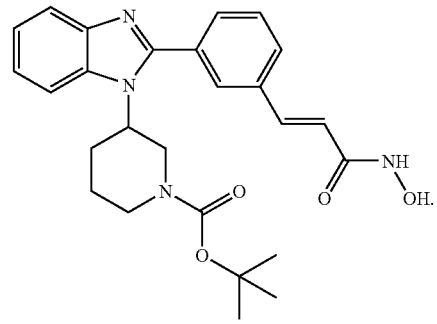

p 3-{2-[3-(2-Hydroxycarbamoyl-vinyl)-phenyl]-benzoimidazol-1-yl}-piperidine-1-carboxylic acid tert-butyl ester $^1$H NMR (400 MHz, DMSO-d$_6$): δ 1.24-1.42 (band, 11H), 1.78 (d, 1H), 2.09 (m, 1H), 2.56 (m, 1H), 2.97 (m, 1H), 3.65 (m, 1H), 3.89 (m, 1H), 4.27 (m, 1H), 6.59 (d, 1H), 7.29 (m, 2H), 7.56-7.99 (band, 7H), 9.09 (s, 1H), 10.86 (s, 1H). ESI-MS: m/z 463.2 (M+H)$^+$.

COMPOUND 4

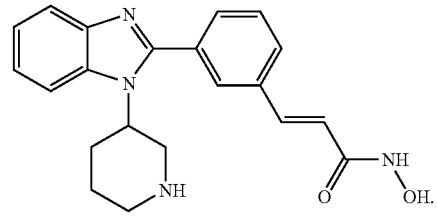

(±)-N-Hydroxy-3-[3-(1-piperidin-3-yl-1H-benzoimidazol-2-yl)-phenyl]-acrylamide

¹H NMR (400 MHz, DMSO-d₆): δ 0.82 (m, 1H), 1.24 (m, 1H), 1.44 (m, 1H), 1.76 (m, 1H), 2.06 (m, 1H), 2.45 (m, 1H), 2.67 (m, 1H), 2.89 (m, 1H), 3.14 (m, 1H), 3.14 (m, 1H), 4.37 (m, 1H), 6.57-6.61 (d, 1H), 7.26 (m, 2H), 7.56-7.99 (band, 7H), 9.09 (s, 1H), 10.86 (s, 1H). ESI-MS: m/z 363.2 (M+H)⁺.

COMPOUND 5

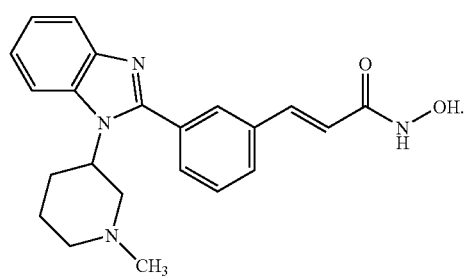

(±)-N-Hydroxy-3-{3-[1-(1-methyl-piperidin-3-yl)-1H-benzoimidazol-2-yl]-phenyl}-acrylamide ¹H NMR (400 MHz, DMSO-d₆): δ 1.50 (m, 1H), 1.78 (d, 1H), 2.02 (m, 1H), 2.25 (m, 5H), 2.74 (m, 2H), 2.94 (m, 1H), 4.42 (m, 1H), 6.59 (d, 1H), 7.26 (m, 2H), 7.56-7.88 (band, 7H), 9.09 (s, 1H), 10.86 (s, 1H). ESI-MS: m/z 376.19 (M+H)⁺.

COMPOUND 6

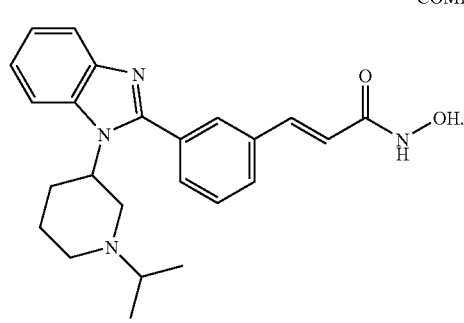

(±)-N-Hydroxy-3-{3-[1-(1-isopropyl-piperidin-3-yl)-1H-benzoimidazol-2-yl]-phenyl}-acrylamide ¹H NMR (400 MHz, DMSO-d₆): δ 0.95 (m, 6H), 1.45 (m, 1H), 1.78 (d, 1H), 2.02 (m, 1H), 2.26-2.31 (m, 2H), 2.68-2.76 (m, 2H), 2.94-2.96 (d, 2H), 4.35-4.37 (m, 1H), 6.57-6.61 (d, 1H), 7.23-7.30 (m, 2H), 7.55-7.89 (band, 7H), 9.09 (s, 1H), 10.86 (s, 1H). ESI-MS: m/z 405.2 (M+H)⁺.

COMPOUND 7

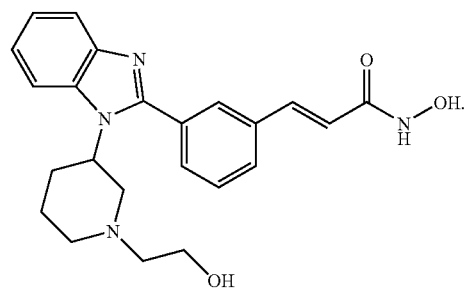

(±)-N-Hydroxy-3-(3-{1-[1-(2-hydroxy-ethyl)-piperidin-3-yl]-1H-benzoimidazol-2-yl}-phenyl)-acrylamide ¹H NMR (400 MHz, DMSO-d₆): δ 1.49-1.55 (m, 1H), 1.78 (d, 1H), 2.02-2.05 (m, 1H), 2.12-2.18 (t, 1H), 2.28-2.33 (m, 1H), 2.45 (t, 2H), 2.83-2.89 (t, 2H), 3.02 (m, 1H), 3.45-3.49 (m, 2H), 4.40 (m, 1H), 6.57-6.61 (d, 1H), 7.23-7.29 (m, 2H), 7.55-7.71 (band, 4H), 7.78 (m, 1H), 7.86-7.89 (m, 2H). ESI-MS: m/z 407.2 (M+H)⁺.

COMPOUND 8

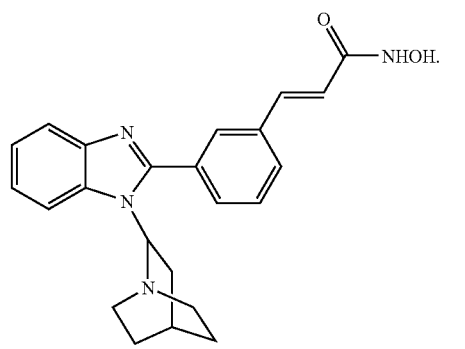

(±)-3-{3-[1-(1-Aza-bicyclo[2.2.2]oct-2-yl)-1H-benzoimidazol-2-yl]-phenyl}-N-hydroxy-acrylamide ¹H NMR (400 MHz, DMSO-d₆): δ 1.53 (m, 1H), 1.64 (m, 2H), 2.06 (m, 1H), 2.30 (m, 1H), 2.73 (m, 2H), 2.90 (m, 1H), 3.20 (m, 1H), 3.35 (m, 1H), 3.60 (m, 1H), 4.60 (m, 1H), 6.57 (d, 1H), 7.30 (m, 2H), 7.53-7.90 (band, 7H), 9.10 (s, 1H), 10.80 (s, 1H). ESI-MS: m/z 389.1 (M+H)⁺.

COMPOUND 9

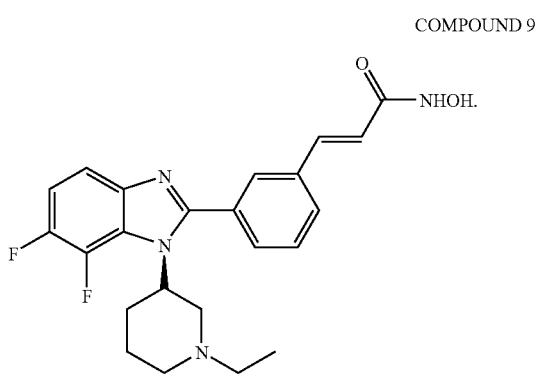

(R)-3-{3-[1-(1-Ethyl-piperidin-3-yl)-6,7-difluoro-1H-benzoimidazol-2-yl]-phenyl}-N-hydroxy-acrylamide $^1$H NMR (400 MHz, DMSO-d$_6$): δ 0.96 (t, 3H), 1.47 (m, 1H), 1.79 (m, 1H), 1.96 (m, 4H), 2.37 (m, 2H), 2.83 (m, 1H), 3.07 (m, 1H), 4.39 (m, 1H), 6.59 (d, 1H), 7.39 (m, 1H), 7.58 (m, 2H), 7.70 (d, 2H), 7.81 (m, 1H), 7.92 (s, 1H), 9.10 (s, 1H), 10.80 (s, 1H). ESI-MS: m/z 427.1 (M+H)$^+$.

COMPOUND 11

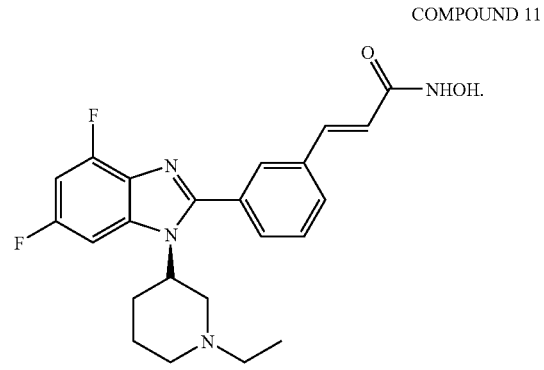

(R)-3-{3-[1-(1-Ethyl-piperidin-3-yl)-4,6-difluoro-1H-benzoimidazol-2-yl]-phenyl}-N-hydroxy-acrylamide $^1$H NMR (400 MHz, DMSO-d$_6$): δ 0.98 (t, 3H), 1.42 (m, 1H), 1.78 (m, 1H), 2.10 (m, 2H), 2.35 (m, 3H), 2.71 (m, 2H), 3.00 (m, 1H), 4.36 (m, 1H), 6.59 (d, 1H), 7.18 (m, 1H), 7.57 (d, 1H), 7.69 (m, 2H), 7.81 (m, 1H), 7.85 (s, 1H), 7.92 (s, 1H), 9.11 (s, 1H), 10.80 (s, 1H). ESI-MS: m/z 427.1 (M+H)$^+$.

COMPOUND 10

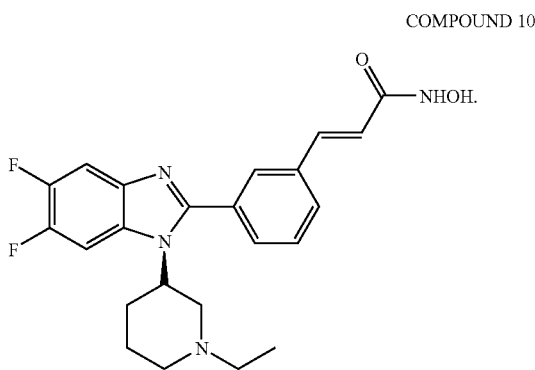

(R)-3-{3-[1-(1-Ethyl-piperidin-3-yl)-5,6-difluoro-1H-benzoimidazol-2-yl]-phenyl}-N-hydroxy-acrylamide-trifluoroacetic acid $^1$H NMR (400 MHz, DMSO-d$_6$): δ 1.18 (t, 3H), 1.60 (m, 1H), 2.14 (m, 2H), 3.22 (m, 3H), 3.55 (m, 1H), 3.82 (m, 3H), 4.72 (m, 1H), 6.59 (d, 1H), 7.61 (m, 3H), 7.85 (m, 3H), 8.27 (m, 1H), 9.40 (s, 1H), 10.80 (s, 1H). ESI-MS: m/z 427.1 (M+H)$^+$.

COMPOUND 12

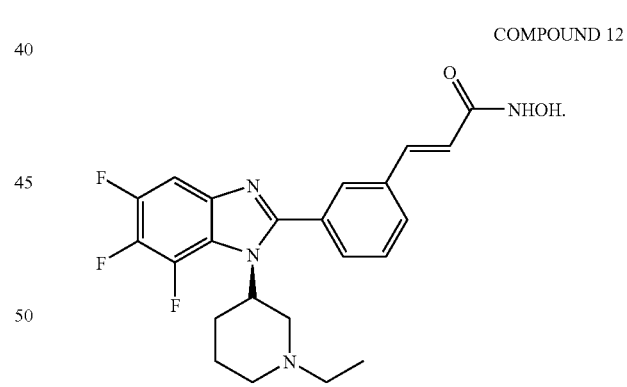

(R)-3-{3-[1-(1-Ethyl-piperidin-3-yl)-5,6,7-trifluoro-1H-benzoimidazol-2-yl]-phenyl}-N-hydroxy-acrylamide $^1$H NMR (400 MHz, DMSO-d$_6$): δ 0.95 (t, 3H), 1.47 (m, 1H), 1.78 (m, 1H), 2.03 (m, 3H), 2.38 (m, 3H), 2.85 (m, 1H), 3.10 (m, 1H), 4.42 (m, 1H), 6.59 (d, 1H), 7.62 (d, 1H), 7.66 (m, 2H), 7.74 (m, 1H), 7.84 (m, 2H), 9.11 (s, 1H), 10.81 (s, 1H). ESI-MS: m/z 445.1 (M+H)$^+$.

COMPOUND 13

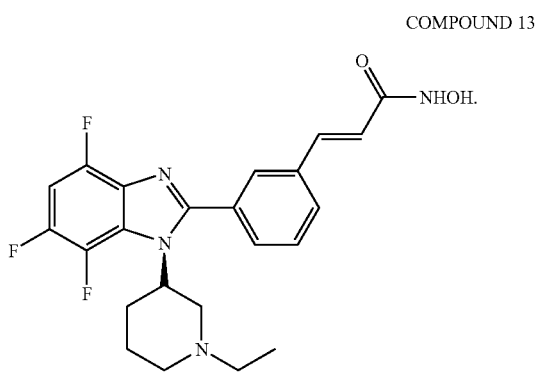

(R)-3-{3-[1-(1-Ethyl-piperidin-3-yl)-4,6,7-trifluoro-1H-benzoimidazol-2-yl]-phenyl}-N-hydroxy-acrylamide $^1$H NMR (400 MHz, DMSO-$d_6$): δ 0.95 (t, 3H), 1.46 (m, 1H), 1.78 (m, 1H), 2.03 (m, 3H), 2.37 (m, 3H), 2.85 (m, 1H), 3.10 (m, 1H), 4.42 (m, 1H), 6.64 (d, 1H), 7.54 (m, 2H), 7.67 (m, 2H), 7.83 (m, 1H), 7.88 (s, 1H), 9.12 (s, 1H), 10.81 (s, 1H). ESI-MS: m/z 445.1 (M+H)$^+$.

COMPOUND 15

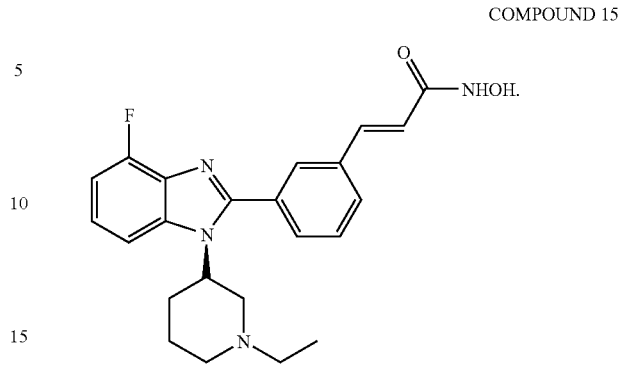

(R)-3-{3-[1-(1-Ethyl-piperidin-3-yl)-4-fluoro-1H-benzoimidazol-2-yl]-phenyl}-N-hydroxy-acrylamide $^1$H NMR (400 MHz, DMSO-$d_6$): δ 0.96 (t, 3H), 1.48 (m, 1H), 1.79 (m, 1H), 2.05 (m, 2H), 2.32 (m, 3H), 2.71 (m, 1H), 2.84 (m, 1H), 3.04 (m, 1H), 4.38 (m, 1H), 6.60 (d, 1H), 7.08 (m, 1H), 7.27 (m, 1H), 7.57 (d, 1H), 7.65 (m, 2H), 7.73 (d, 1H), 7.80 (m, 1H), 7.87 (s, 1H), 9.11 (s, 1H), 10.80 (s, 1H). ESI-MS: m/z 409.1 (M+H)$^+$.

COMPOUND 14

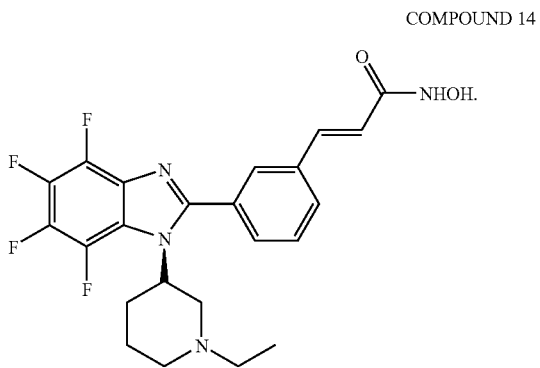

(R)-3-{3-[1-(1-Ethyl-piperidin-3-yl)-4,5,6,7-tetrafluoro-1H-benzoimidazol-2-yl]-phenyl}-N-hydroxy-acrylamide $^1$H NMR (400 MHz, DMSO-$d_6$): δ 0.95 (t, 3H), 1.46 (m, 1H), 1.79 (m, 1H), 2.04 (m, 3H), 2.37 (m, 3H), 2.85 (m, 1H), 3.17 (m, 1H), 4.45 (m, 1H), 6.60 (d, 1H), 7.58 (d, 1H), 7.67 (m, 2H), 7.85 (m, 1H), 7.88 (s, 1H), 9.12 (s, 1H), 10.81 (s, 1H). ESI-MS: m/z 463.1 (M+H)$^+$.

COMPOUND 16

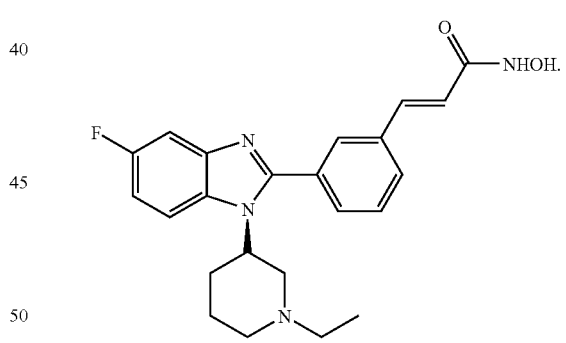

(R)-3-{3-[1-(1-Ethyl-piperidin-3-yl)-5-fluoro-1H-benzoimidazol-2-yl]-phenyl}-N-hydroxy-acrylamide $^1$H NMR (400 MHz, DMSO-$d_6$): δ 0.96 (t, 3H), 1.48 (m, 1H), 1.79 (m, 1H), 2.05 (m, 2H), 2.32 (m, 3H), 2.71 (m, 1H), 2.84 (m, 1H), 3.03 (m, 1H), 4.38 (m, 1H), 6.59 (d, 1H), 7.14 (m, 1H), 7.49 (m, 1H), 7.57 (d, 1H), 7.65 (m, 2H), 7.79 (m, 1H), 7.89 (s, 1H), 7.90-7.93 (m, 1H), 9.11 (s, 1H), 10.80 (s, 1H). ESI-MS: m/z 409.1 (M+H)$^+$.

COMPOUND 17

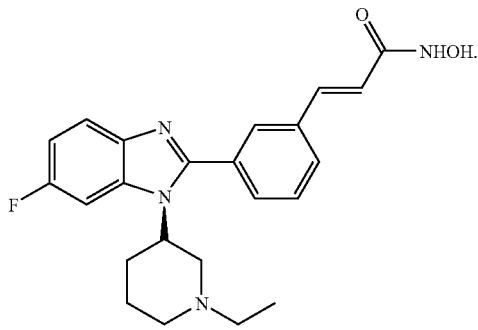

(R)-3-{3-[1-(1-Ethyl-piperidin-3-yl)-6-fluoro-1H-benzoimidazol-2-yl]-phenyl}-N-hydroxy-acrylamide $^1$H NMR (400 MHz, DMSO-d$_6$): δ 0.96 (t, 3H), 1.47 (m, 1H), 1.78 (m, 1H), 2.11 (m, 2H), 2.32 (m, 3H), 2.71 (m, 1H), 2.83 (m, 1H), 3.00 (m, 1H), 4.36 (m, 1H), 6.59 (d, 1H), 7.12 (m, 1H), 7.56 (d, 1H), 7.63 (m, 2H), 7.70 (m, 1H), 7.77 (m, 2H), 7.84 (s, 1H), 9.11 (s, 1H), 10.80 (s, 1H). ESI-MS: m/z 409.1 (M+H)$^+$.

COMPOUND 19

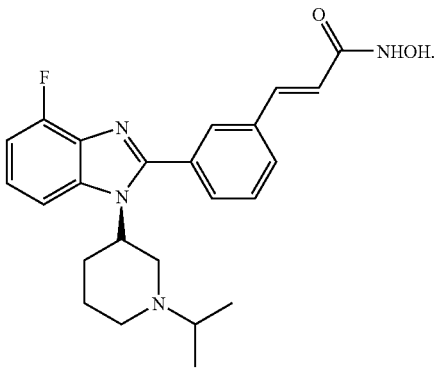

(R)-3-{3-[4-Fluoro-1-(1-isopropyl-piperidin-3-yl)-1H-benzoimidazol-2-yl]-phenyl}-N-hydroxy-acrylamide $^1$H NMR (400 MHz, DMSO-d$_6$): δ 0.95 (d, 6H), 1.45 (m, 1H), 1.79 (m, 1H), 2.02 (m, 1H), 2.27 (m, 2H), 2.73 (m, 2H), 2.98 (m, 2H), 4.35 (m, 1H), 6.60 (d, 1H), 7.08 (m, 1H), 7.26 (m, 1H), 7.57 (d, 1H), 7.65 (m, 2H), 7.74 (d, 1H), 7.80 (m, 1H), 7.86 (s, 1H), 9.11 (s, 1H), 10.80 (s, 1H). ESI-MS: m/z 423.1 (M+H)$^+$.

COMPOUND 18

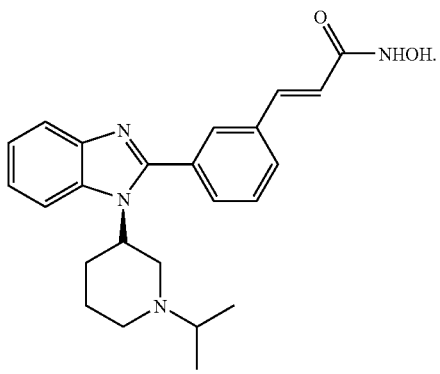

(R)-N-Hydroxy-3-{3-[1-(1-isopropyl-piperidin-3-yl)-1H-benzoimidazole-2-yl]-phenyl}-acrylamide $^1$H NMR (400 MHz, DMSO-d$_6$): δ 0.95 (d, 6H), 1.45 (m, 1H), 1.79 (m, 1H), 2.01 (m, 1H), 2.29 (m, 2H), 2.74 (m, 2H), 3.04 (m, 2H), 4.35 (m, 1H), 6.59 (d, 1H), 7.25 (m, 2H), 7.56 (d, 1H), 7.63 (m, 2H), 7.69 (m, 1H), 7.79 (m, 1H), 7.84 (s, 1H), 7.88 (d, 1H), 9.11 (s, 1H), 10.80 (s, 1H). ESI-MS: m/z 405.2 (M+H)$^+$.

COMPOUND 20

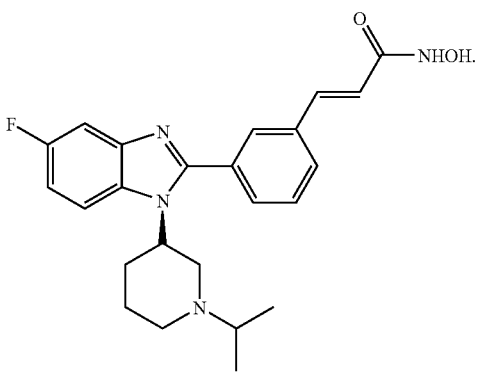

(R)-3-{3-[5-Fluoro-1-(1-isopropyl-piperidin-3-yl)-1H-benzoimidazol-2-yl]-phenyl}-N-hydroxy-acrylamide $^1$H NMR (400 MHz, DMSO-d$_6$): δ 0.95 (d, 6H), 1.44 (m, 1H), 1.79 (m, 1H), 2.04 (m, 1H), 2.27 (m, 2H), 2.73 (m, 2H), 2.98 (m, 2H), 4.35 (m, 1H), 6.59 (d, 1H), 7.14 (m, 1H), 7.50 (m, 1H), 7.56 (d, 1H), 7.64 (m, 2H), 7.79 (m, 1H), 7.84 (s, 1H), 7.92 (m, 1H), 9.11 (s, 1H), 10.80 (s, 1H). ESI-MS: m/z 423.1 (M+H)$^+$.

COMPOUND 21

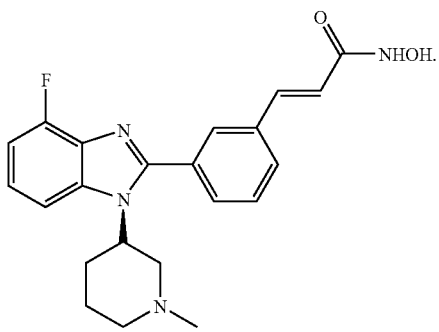

(R)-3-{3-[4-Fluoro-1-(1-methyl-piperidin-3-yl)-1H-benzoimidazol-2-yl]-phenyl}-N-hydroxy-acrylamide $^1$H NMR (400 MHz, DMSO-d$_6$): δ 1.49 (m, 1H), 1.78 (m, 1H), 2.06 (m, 2H), 2.24 (m, 4H), 2.72 (m, 2H), 2.95 (m, 1H), 4.42 (m, 1H), 6.60 (d, 1H), 7.08 (m, 1H), 7.26 (m, 1H), 7.58 (d, 1H), 7.65 (m, 2H), 7.73 (d, 1H), 7.80 (m, 1H), 7.88 (s, 1H), 9.11 (s, 1H), 10.80 (s, 1H). ESI-MS: m/z 395.1 (M+H)$^+$.

COMPOUND 22

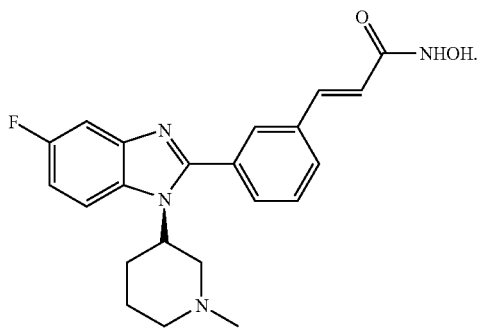

(R)-3-{3-[5-Fluoro-1-(1-methyl-piperidin-3-yl)-1H-benzoimidazol-2-yl]-phenyl}-N-hydroxy-acrylamide $^1$H NMR (400 MHz, DMSO-d$_6$): δ 1.49 (m, 1H), 1.77 (m, 1H), 2.03 (m, 2H), 2.24 (m, 4H), 2.72 (m, 2H), 2.99 (m, 1H), 4.43 (m, 1H), 6.59 (d, 1H), 7.14 (m, 1H), 7.50 (m, 1H), 7.57 (d, 1H), 7.64 (m, 2H), 7.78 (m, 1H), 7.85 (s, 1H), 7.91 (m, 1H), 9.11 (s, 1H), 10.80 (s, 1H). ESI-MS: m/z 395.1 (M+H)$^+$.

COMPOUND 23

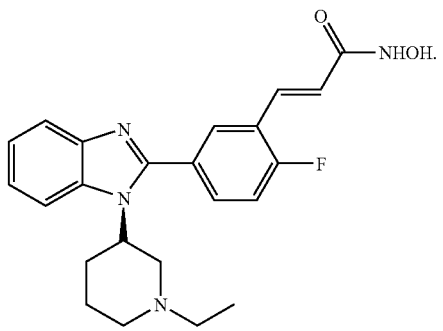

(R)-3-{5-[1-(1-Ethyl-piperidin-3-yl)-1H-benzoimidazol-2-yl]-2-fluoro-phenyl}-N-hydroxy-acrylamide $^1$H NMR (400 MHz, DMSO-d$_6$): δ 0.96 (t, 3H), 1.51 (m, 1H), 1.79 (m, 1H), 2.04 (m, 2H), 2.34 (m, 3H), 2.75 (m, 1H), 2.86 (m, 1H), 3.03 (m, 1H), 4.37 (m, 1H), 6.70 (d, 1H), 7.26 (m, 2H), 7.48 (m, 1H), 7.58 (d, 1H), 7.71 (m, 2H), 7.87 (m, 1H), 7.95 (d, 1H), 9.15 (s, 1H), 10.90 (s, 1H). ESI-MS: m/z 409.1 (M+H)$^+$.

COMPOUND 24

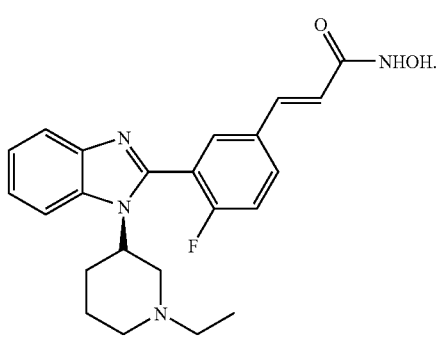

(R)-3-{3-[1-(1-Ethyl-piperidin-3-yl)-1H-benzoimidazol-2-yl]-4-fluoro-phenyl}-N-hydroxy-acrylamide $^1$H NMR (400 MHz, DMSO-d$_6$): δ 1.01 (t, 3H), 1.48 (m, 1H), 1.79 (m, 1H), 1.99 (m, 2H), 2.32 (m, 3H), 2.71 (m, 1H), 2.85 (m, 1H), 2.98 (m, 1H), 4.12 (m, 1H), 6.53 (d, 1H), 7.30 (m, 2H), 7.53 (m, 2H), 7.72 (d, 1H), 7.90 (m, 3H), 9.10 (s, 1H), 10.77 (s, 1H). ESI-MS: m/z 409.1 (M+H)$^+$.

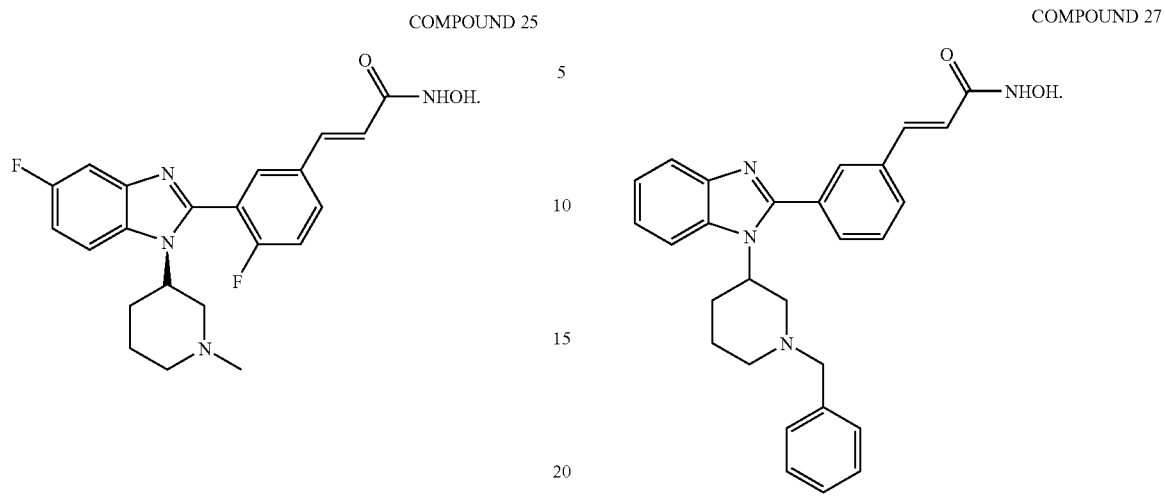

COMPOUND 25

(R)-3-{4-Fluoro-3-[5-fluoro-1-(1-methyl-piperidin-3-yl)-1H-benzoimidazol-2-yl]-phenyl}-N-hydroxy-acrylamide $^1$H NMR (400 MHz, DMSO-d$_6$): δ 1.47 (m, 1H), 1.75 (m, 1H), 1.90 (m, 1H), 2.05 (m, 1H), 2.19 (m, 4H), 2.69 (m, 2H), 2.87 (m, 1H), 4.11 (m, 1H), 6.53 (d, 1H), 7.19 (m, 1H), 7.54 (m, 3H), 7.87 (m, 2H), 7.96 (m, 1H), 9.11 (s, 1H), 10.80 (s, 1H). ESI-MS: m/z 413.1 (M+H)$^+$.

COMPOUND 27

(±)-3-{3-[1-(1-Benzyl-piperidin-3-yl)-1H-benzoimidazol-2-yl]-phenyl}-N-hydroxy-acrylamide $^1$H NMR (400 MHz, DMSO-d$_6$): δ 1.50 (m, 1H), 1.78 (d, 1H), 2.03 (br s, 2H), 2.14 (m, 1H), 2.33 (m, 1H), 2.82 (m, 2H), 2.95 (m; 1H), 3.55 (m, 1H), 4.40 (m, 1H), 6.60 (d, 1H), 7.23-7.34 (band, 7H), 7.53-7.69 (band, 4H), 7.75-7.87 (band, 3H), 9.11 (s, 1H), 10.80 (s, 1H). ESI-MS: m/z 453.2 (M+H)$^+$.

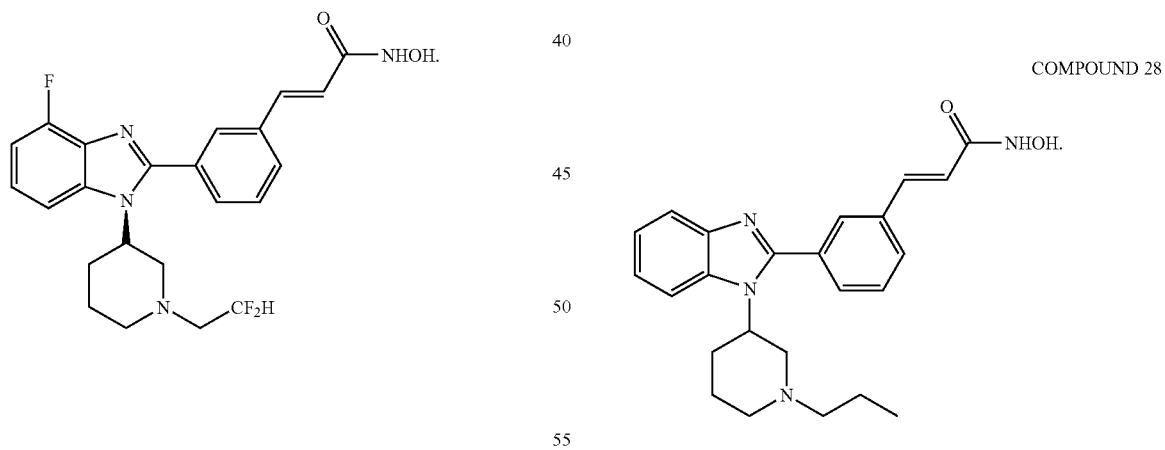

COMPOUND 26

(R)-3-(3-{1-[1-(2,2-Difluoro-ethyl)-piperidin-3-yl]-4-fluoro-1H-benzoimidazol-2-yl}-phenyl)-N-hydroxy-acrylamide $^1$H NMR (400 MHz, DMSO-d$_6$): δ 1.49 (m, 1H), 1.78 (m, 1H), 2.05 (m, 1H), 2.32 (m, 2H), 2.83 (m, 3H), 3.08 (m, 2H), 4.40 (m, 1H), 6.13 (m, 1H), 6.60 (d, 1H), 7.08 (m, 1H), 7.26 (m, 1H), 7.58 (d, 1H), 7.66 (m, 2H), 7.75 (d, 1H), 7.81 (m, 1H), 7.87 (s, 1H), 9.11 (s, 1H), 10.80 (s, 1H). ESI-MS: m/z 445.1 (M+H)$^+$.

COMPOUND 28

(±)-N-Hydroxy-3-{3-[1-(1-propyl-piperidin-3-yl)-1H-benzoimidazol-2-yl]-phenyl}-acrylamide $^1$H NMR (400 MHz, DMSO-d$_6$): δ 0.79 (t, 3H), 1.45 (m, 3H), 1.78 (d, 1H), 2.04 (m, 2H), 2.29 (m, 3H), 2.78 (m, 2H), 3.02 (m, 1H), 4.40 (m, 1H), 6.59 (d, 1H), 7.26 (m, 2H), 7.55-7.71 (band, 4H), 7.78 (m, 1H), 7.86 (m, 2H), 9.11 (s, 1H), 10.80 (s, 1H). ESI-MS: m/z 405.2 (M+H)$^+$.

COMPOUND 29

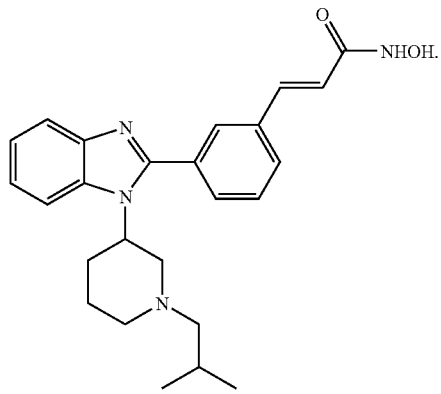

(±)-N-Hydroxy-3-{3-[1-(1-isobutyl-piperidin-3-yl)-1H-benzoimidazol-2-yl]-phenyl}-acrylamide ¹H NMR (400 MHz, DMSO-d₆): δ 0.82 (d d, 6H), 1.46 (m, 1H), 1.77 (m, 2H), 1.97 (m, 1H), 2.09 (m, 3H), 2.30 (m, 1H), 2.73 (m, 2H), 3.04 (d, 1H), 4.38 (m, 1H), 6.59 (d, 1H), 7.26 (m, 2H), 7.55-7.89 (band, 7H), 9.11 (s, 1H), 10.80 (s, 1H). ESI-MS: m/z 419.2 (M+H)⁺.

COMPOUND 31

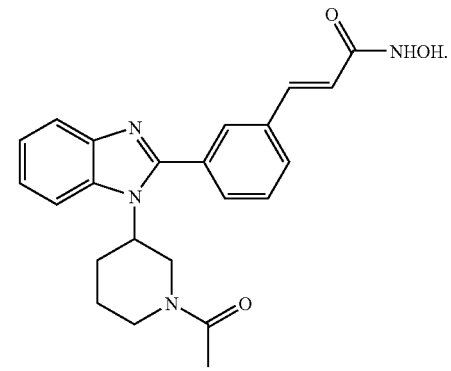

(±)-3-{3-[1-(1-Acetyl-piperidin-3-yl)-1H-benzoimidazol-2-yl]-phenyl}-N-hydroxy-acrylamide ¹H NMR (400 MHz, CDCl₃-d): δ 1.60 (m, 1H), 1.94 (m, 2H), 2.29 (s, 3H), 2.73 (m, 1H), 3.28 (t, 1H), 3.60 (t, 1H), 3.99 (d, 1H), 4.57 (m, 1H), 5.39 (d, 1H), 6.88 (d, 1H), 7.34 (m, 2H), 7.51-7.69 (band, 5H), 7.89 (m, 2H), 9.11 (s, 1H), 10.80 (s, 1H). ESI-MS: m/z 405.1 (M+H)⁺.

COMPOUND 30

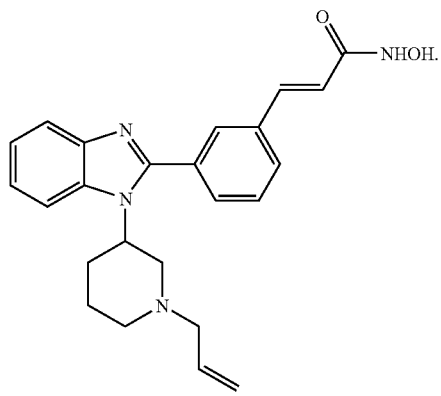

(±)-3-{3-[1-(1-Allyl-piperidin-3-yl)-1H-benzoimidazol-2-yl]-phenyl}-N-hydroxy-acrylamide ¹H NMR (400 MHz, DMSO-d₆): δ 1.49 (m, 1H), 1.79 (d, 1H), 2.09 (m, 2H), 2.30 (m, 1H), 2.80 (m, 2H), 2.97 (m, 3H), 4.40 (m, 1H), 5.15 (M, 2H), 5.79 (m, 1H), 6.59 (d, 1H), 7.26 (m, 2H), 7.56-7.71 (band, 4H), 7.82 (m, 3H), 9.11 (s, 1H), 10.80 (s, 1H). ESI-MS: m/z 403.2 (M+H)⁺.

COMPOUND 32

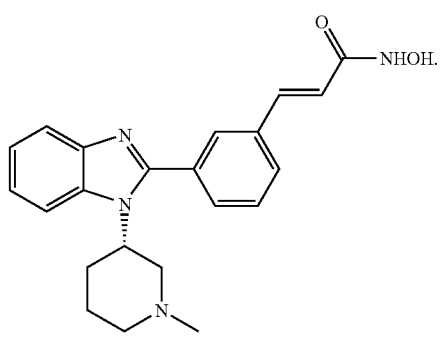

(S)-N-Hydroxy-3-{3-[1-(1-methyl-piperidin-3-yl)-1H-benzoimidazol-2-yl]-phenyl}-acrylamide ¹H NMR (400 MHz, DMSO-d₆): δ 1.50 (m, 1H), 1.78 (d, 1H), 2.02 (m, 1H), 2.24 (m, 5H), 2.74 (br s, 2H), 2.94 (br s, 1H), 4.42 (m, 1H), 6.59 (d, 1H), 7.26 (m, 2H), 7.56-7.88 (band, 7H), 9.11 (s, 1H), 10.80 (s, 1H). ESI-MS: m/z 377.1 (M+H)⁺.

COMPOUND 33

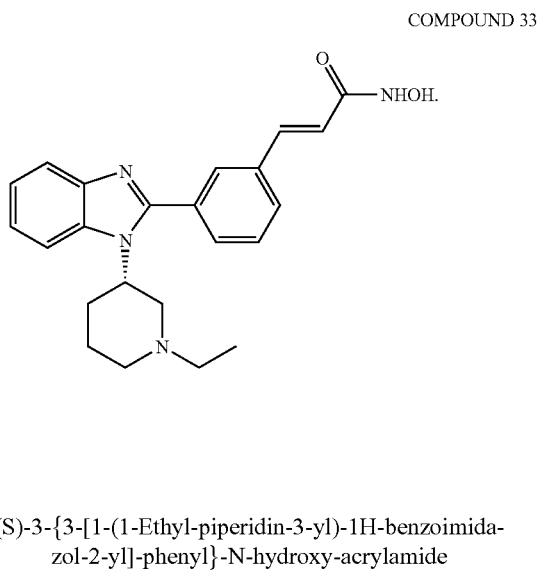

(S)-3-{3-[1-(1-Ethyl-piperidin-3-yl)-1H-benzoimidazol-2-yl]-phenyl}-N-hydroxy-acrylamide $^1$H NMR (400 MHz, DMSO-d$_6$): δ 0.96 (t, 3H), 1.50 (m, 1H), 1.78 (d, 1H), 2.05 (m, 2H), 2.33 (m, 3H), 2.75 (t, 1H), 2.84 (d, 1H), 3.02 (m, 1H), 4.40 (m, 1H), 6.59 (d, 1H), 7.26 (m, 2H), 7.51-7.88 (band, 7H), 9.11 (s, 1H), 10.80 (s, 1H). ESI-MS: m/z 391.2 (M+H)$^+$.

COMPOUND 35

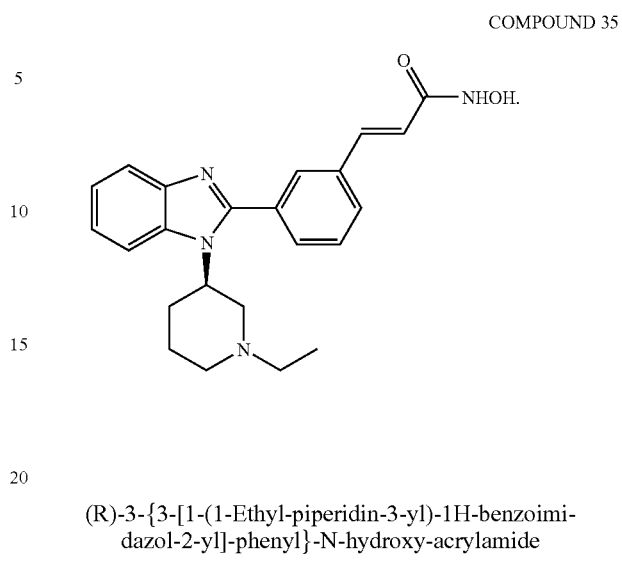

(R)-3-{3-[1-(1-Ethyl-piperidin-3-yl)-1H-benzoimidazol-2-yl]-phenyl}-N-hydroxy-acrylamide $^1$H NMR (400 MHz, DMSO-d$_6$): δ 0.96 (t, 3H), 1.50 (m, 1H), 1.78 (d, 1H), 2.05 (m, 2H), 2.33 (m, 3H), 2.75 (t, 1H), 2.84 (d, 1H), 3.02 (d, 1H), 4.40 (m, 1H), 6.59 (d, 1H), 7.26 (m, 2H), 7.55-7.88 (band, 7H), 9.11 (s, 1H), 10.80 (s, 1H). ESI-MS: m/z 391.2 (M+H)$^+$.

COMPOUND 34

(R)-N-Hydroxy-3-{3-[1-(1-methyl-piperidin-3-yl)-1H-benzoimidazol-2-yl]-phenyl}-acrylamide $^1$H NMR (400 MHz, DMSO-d$_6$): δ 1.50 (m, 1H), 1.78 (d, 1H), 2.02 (m, 2H), 2.21-2.33 (m, 4H), 2.75 (m, 2H), 2.94 (m, 1H), 4.42 (m, 1H), 6.59 (d, 1H), 7.26 (m, 2H), 7.56-7.88 (band, 7H), 9.11 (s, 1H), 10.80 (s, 1H). ESI-MS: m/z 377.1 (M+H)$^+$.

COMPOUND 36

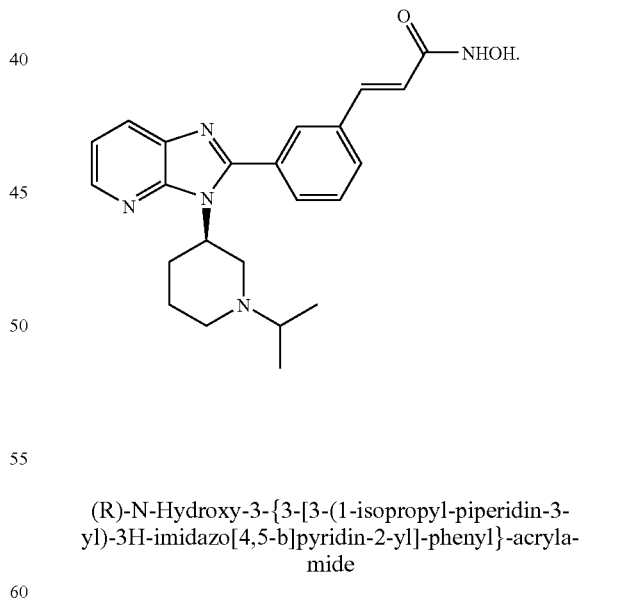

(R)-N-Hydroxy-3-{3-[3-(1-isopropyl-piperidin-3-yl)-3H-imidazo[4,5-b]pyridin-2-yl]-phenyl}-acrylamide $^1$H NMR (400 MHz, DMSO-d$_6$): δ0.95 (br s, 6H), 1.43 (m, 1H), 1.78 (m, 1H), 1.99 (m, 1H), 2.19 (m, 1H), 2.75 (m, 3H), 2.92 (m, 1H), 3.25 (m, 1H), 4.35 (m, 1H), 6.58 (d, 1H), 7.31 (m, 1H), 7.57 (d, 1H), 7.65 (m, 2H), 7.81 (d, 1H), 7.89 (s, 1H), 8.11 (d, 1H), 8.41 (d, 1H), 9.11 (s, 1H), 10.80 (s, 1H). ESI-MS: m/z 406.2 (M+H)$^+$.

COMPOUND 37

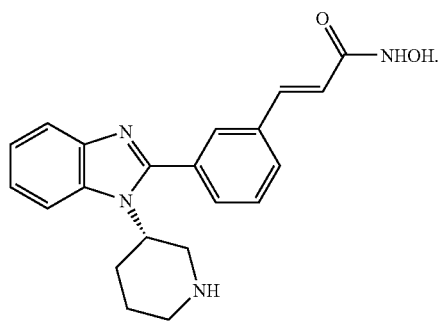

(S)-N-Hydroxy-3-[3-(1-piperidin-3-yl-1H-benzoimidazol-2-yl)-phenyl]-acrylamide.

$^1$H NMR (400 MHz, DMSO-d$_6$): δ 1.70 (m, 1H), 1.90 (m, 1H), 2.20 (m, 1H), 2.49 (m, 3H), 3.30 (m, 2H), 4.70 (m, 1H), 6.60 (d, 1H), 7.31 (m, 2H), 7.51-7.90 (m, 7H), 9.11 (s, 1H), 10.80 (s, 1H). ESI-MS: m/z 363.2 (M+H)$^+$.

COMPOUND 38

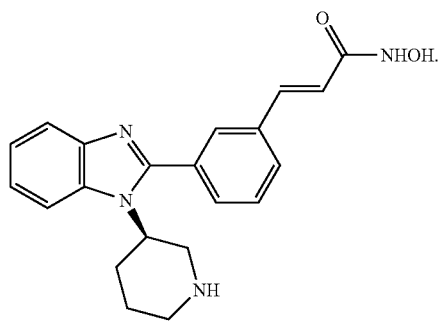

(R)-N-Hydroxy-3-[3-(1-piperidin-3-yl-1H-benzoimidazol-2-yl)-phenyl]-acrylamide $^1$H NMR (400 MHz, DMSO-d$_6$): δ 1.39 (m, 1H), 1.70 (m, 1H), 2.00 (m, 1H), 2.45 (m, 3H), 2.80 (m, 1H), 3.05 (m, 1H), 4.30 (m, 1H), 6.60 (d, 1H), 7.31 (m, 2H), 7.51-7.90 (m, 7H), 9.11 (s, 1H), 10.80 (s, 1H). ESI-MS: m/z 363.2 (M+H)$^+$.

COMPOUND 39

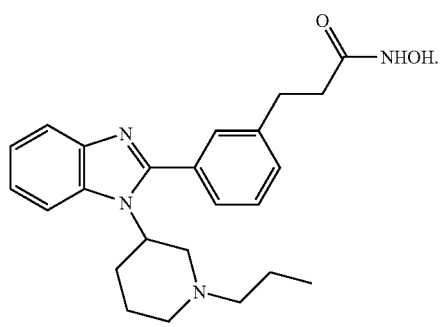

(±)-N-Hydroxy-3-{3-[1-(1-propyl-piperidin-3-yl)-1H-benzoimidazol-2-yl]-phenyl}-propionamide $^1$H NMR (400 MHz, DMSO-d$_6$): δ 0.98 (t, 3H), 1.71 (m, 3H), 2.01 (m, 2H), 2.31 (m, 1H), 2.97 (m, 2H), 3.20 (m, 1H), 3.49 (m, 1H), 3.98 (m, 2H), 4.68 (m, 1H), 7.35 (m, 2H), 7.48 (d, 1H), 7.54 (m, 3H), 7.74 (m, 1H), 8.08 (m, 1H), 9.11 (s, 1H), 10.80 (s, 1H). ESI-MS: m/z 407.2 (M+H)$^+$.

COMPOUND 40

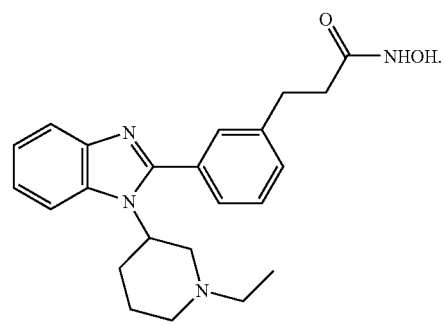

(±)-3-{3-[1-(1-Ethyl-piperidin-3-yl)-1H-benzoimidazol-2-yl]-phenyl}-N-hydroxy-propionamide $^1$H NMR (400 MHz, DMSO-d$_6$): δ 1.29 (t, 3H), 1.75 (m, 1H), 1.98 (m, 2H), 2.31 (m, 2H), 2.48 (m, 2H), 2.95 (m, 2H), 3.20 (m, 2H), 3.42 (m, 1H), 3.82 (m, 1H), 3.95 (m, 1H), 4.68 (m, 1H), 7.35 (m, 2H), 7.48 (d, 1H), 7.54 (m, 3H), 7.74 (m, 1H), 8.08 (m, 1H), 9.68 (s, 1H), 10.80 (s, 1H). ESI-MS: m/z 393.2 (M+H)$^+$.

COMPOUND 41

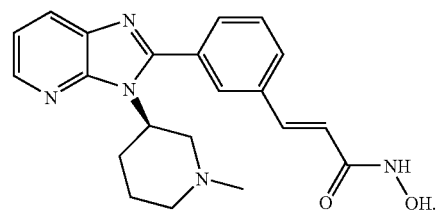

N-Hydroxy-3-{3-[3-(1-methyl-piperidin-3-yl)-3H-imidazo[4,5-b]pyridin-2-yl]-phenyl}-acrylamide $^1$H NMR (400 MHz, DMSO-d$_6$): δ 1.49 (m, 1H), 1.76 (m, 1H), 1.95 (m, 2H), 2.20 (s, 3H), 2.70 (m, 2H), 2.93 (m, 1H), 3.09 (m, 1H), 4.41 (m, 1H), 6.58 (d, 1H), 7.31 (m, 1H), 7.56-7.60 (d, 1H), 7.66 (m, 2H), 7.81 (d, 1H), 7.90 (s, 1H), 8.11 (d, 1H), 8.41 (d, 1H). ESI-MS: m/z 377.19 (M+H)$^+$.

COMPOUND 42

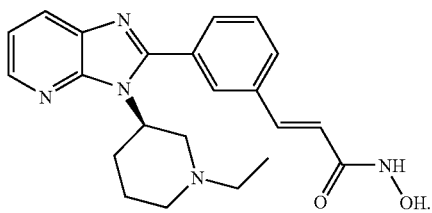

(R)-3-{3-[3-(1-Ethyl-piperidin-3-yl)-3H-imidazo[4,5-b]pyridin-2-yl]-phenyl}-N-hydroxy-acrylamide ESI-MS: m/z 392.2 (M+H)$^+$.

COMPOUND 43

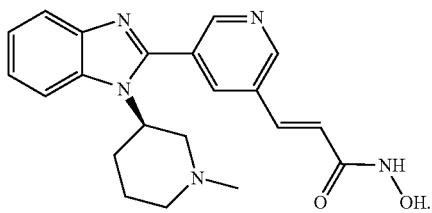

(R)-N-Hydroxy-3-{5-[1-(1-methyl-piperidin-3-yl)-1H-benzoimidazol-2-yl]-pyridin-3-yl}-acrylamide $^1$H NMR (400 MHz, DMSO-d$_6$): δ 1.56 (m, 1H), 1.77 (m, 1H), 2.05 (m, 2H), 2.27 (m, 4H), 2.75 (m, 2H), 3.02 (m, 1H), 4.35 (m, 1H), 6.70 (d, 1H), 7.31 (m, 2H), 7.61 (d, 1H), 7.72 (m, 1H), 7.90 (d, 1H), 8.29 (s, 1H), 8.83 (s, 1H), 8.98 (s, 1H). ESI-MS: m/z 378.2 (M+H)$^+$.

COMPOUND 44

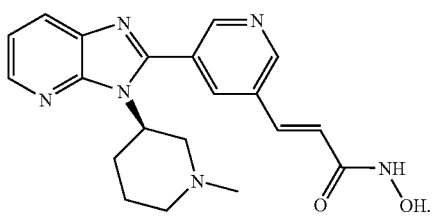

(R)-N-Hydroxy-3-{5-[3-(1-methyl-piperidin-3-yl)-3H-imidazo[4,5-b]pyridin-2-yl]-pyridin-3-yl}-acrylamide $^1$H NMR (400 MHz, DMSO-d$_6$): δ 1.51 (m, 1H), 1.92 (m, 3H), 2.15 (s, 3H), 2.71 (m, 2H), 3.02 (m, 2H), 4.33 (m, 1H), 6.78 (br d, 1H), 7.33 (m, 2H), 8.13 (d, 1H), 8.27 (s, 1H), 8.42 (d, 1H), 8.79 (s, 1H), 8.95 (s, 1H). ESI-MS: m/z 379.2 (M+H)$^+$.

As used herein the symbols and conventions used in these processes, schemes and examples are consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i.v. (intravenous); Hz (Hertz);
MHz (megahertz); mol (moles);
mmol (millimoles); RT (ambient temperature);
min (minutes); h (hours);
mp (melting point); TLC (thin layer chromatography);
Tr (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
Et2O (diethyl ether); EDCI (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); Me (methyl);
OMe (methoxy); Et (ethyl);
Et (ethyl); tBu (tert-butyl);
HPLC (high pressure liquid chromatography);
BOP (bis(2-oxo-3-oxazolidinyl)phosphinic chloride);
TBAF (tetra-n-butylammonium fluoride);
mCPBA (meta-chloroperbenzoic acid.

All references to ether or Et$_2$O are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR spectra were recorded on a Bruker Avance 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporate light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

It will be apparent to those skilled in the art that various modifications and variations can be made to the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound consisting of the formula:

Z-Q-L-M wherein

Z-Q- is selected from the group consisting of

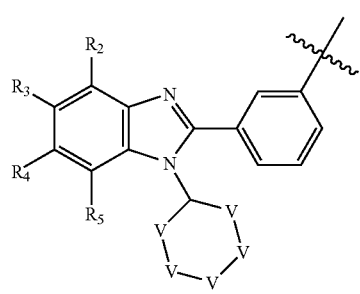

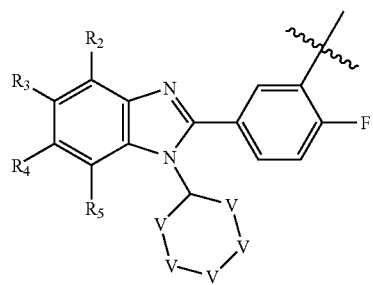

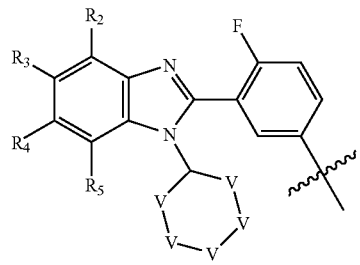

V is selected from the group consisting of $C(R_{12})_2$ and $NR_{12}$ where only one V is $NR_{12}$;

$R_2$, $R_3$, $R_4$, and $R_5$ are each independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted;

each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that when the ring atom to which $R_{12}$ is bound is nitrogen, $R_{12}$ not halo, cyano, nitro, or thio;

M is selected from the group consisting of trifluoroacetyl (—C(O)—CF$_3$), —NH—P(O)OH—CH$_3$, sulfonamides (—SO$_2$NH$_2$), hydroxysulfonamides (—SO$_2$NHOH), thiols (—SH), and carbonyl groups having the formula —C(O)—R$_{13}$ wherein R$_{13}$ is hydroxylamino, hydroxyl, amino, alkylamino, and an alkoxy group; and L is a substituent providing between 2-10 atoms separation between the M substituent and the Q substituent, wherein the 2-10 atoms are all carbon atoms.

2. The compound according to claim 1, wherein V are selected so that the ring is an N-substituted piperidin-3-yl moiety.

3. The compound according to claim 1, wherein at least one of $R_2$, $R_3$, $R_4$, or $R_5$ is fluoro.

4. The compound according to claim 1, wherein M is selected from the group consisting of:

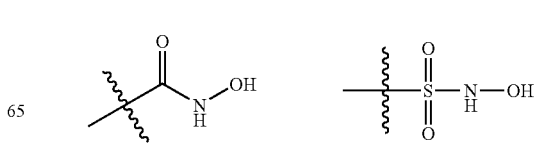

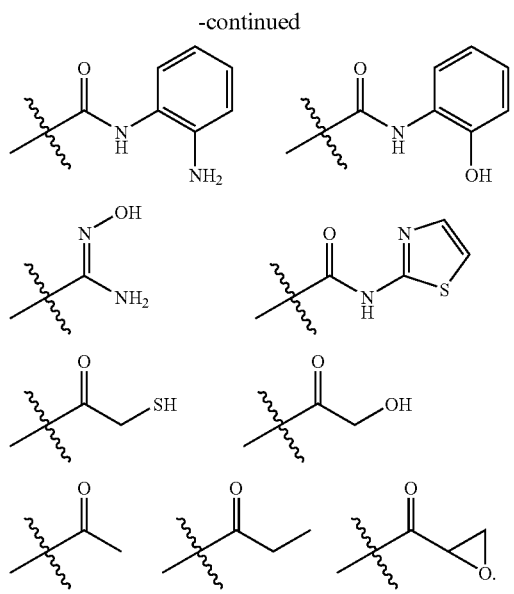

5. The compound according to claim 1, wherein M is a hydroxamic acid moiety.

6. A compound according to claim 1, wherein -L-M is

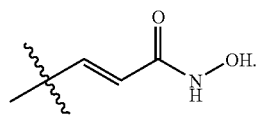

7. A compound comprising the formula:

Z-Q-L-M wherein

Z-Q- is selected from the group consisting of

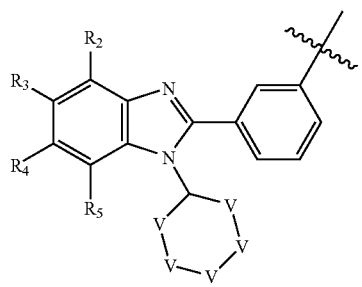

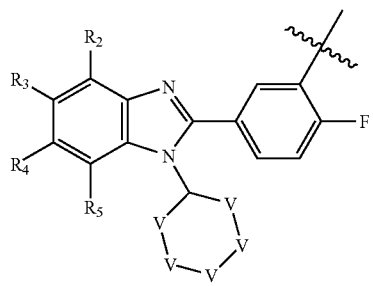

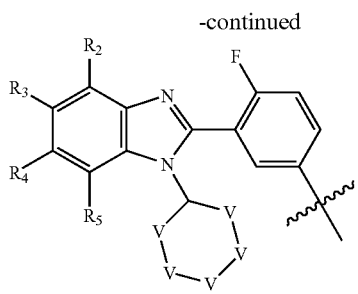

each V is selected from the group consisting of $C(R_{12})_2$ and $NR_{12}$ where only one V is $NR_{12}$;

$R_2$, $R_3$, $R_4$, and $R_5$ are each independently selected from the group consisting of hydrogen, halo, alkyl, alkoxy, aryl, cyano, and nitro;

each $R_{12}$ is independently selected from the group consisting of hydrogen, halo, alkyl, alkoxy, aryl, heteroaryl, aminosulfonyl, alkylsulfonyl, arylsulfonyl, heteroarylsulfonyl, aryloxy, heteroaryloxy, arylalkyl, heteroarylalkyl, amino, thio, cyano, nitro, and a carbonyl group, each substituted or unsubstituted, with the proviso that when the ring atom to which $R_{12}$ is bound is nitrogen, $R_{12}$ is not halo, cyano, nitro, or thio;

M is selected from the group consisting of trifluoroacetyl (—C(O)—CF$_3$), —NH—P(O)OH—CH$_3$, sulfonamides (—SO$_2$NH$_2$), hydroxysulfonamides (—SO$_2$NHOH), thiols (—SH), and carbonyl groups having the formula —C(O)—R$_{13}$ wherein R$_{13}$ is hydroxylamino, hydroxyl, amino, alkylamino, and an alkoxy group; and L is selected from the group consisting of (E) isomer of —CH═CH—, (Z) isomer of —CHCH—, and mixtures of (E) and (Z) isomers of —CH═CH—.

8. The compound according to claim 7, wherein V are selected so that the ring is an N-substituted piperidin-3-yl moiety.

9. The compound according to claim 7 wherein at least one of $R_2$, $R_3$, $R_4$, or $R_5$ is fluoro.

10. The compound according to claim 7, wherein M is selected from the group consisting of:

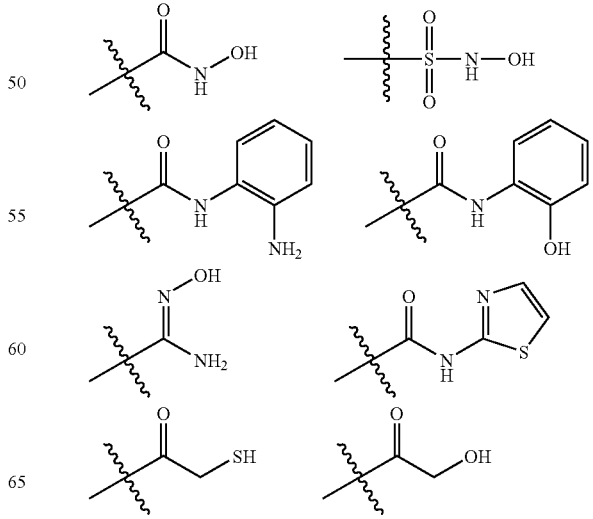

-continued

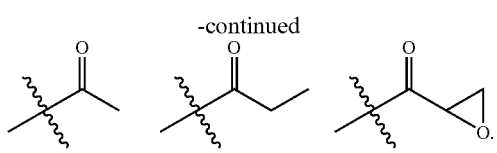

11. The compound according to claim 7, wherein M is a hydroxamic acid moiety.

12. The compound according to claim 7, wherein -L-M is

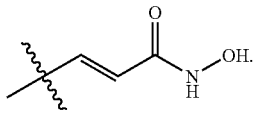

13. The compound according to claim 1, wherein M is

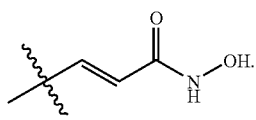

14. The compound according to claim 1, wherein M is

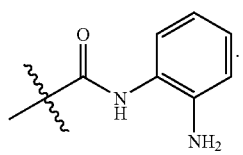

15. The compound according to claim 1, wherein M is

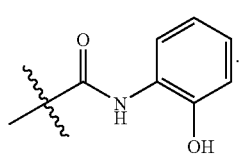

16. The compound according to claim 1, wherein M is

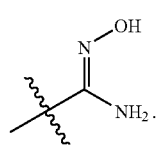

17. The compound according to claim 1, wherein M is

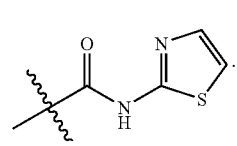

18. The compound according to claim 1, wherein M is

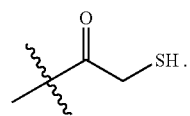

19. The compound according to claim 1, wherein M is

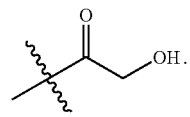

20. The compound according to claim 1, wherein M is

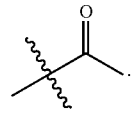

21. The compound according to claim 1, wherein M is

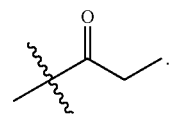

22. The compound according to claim 1, wherein M is

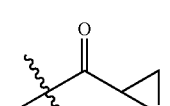

23. The compound according to claim 7, wherein M is

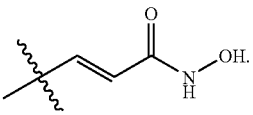

24. The compound according to claim 7, wherein M is

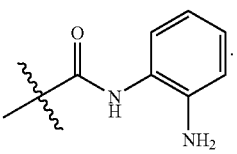

25. The compound according to claim 7, wherein M is

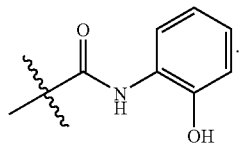

26. The compound according to claim 7, wherein M is

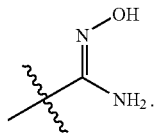

27. The compound according to claim 7, wherein M is

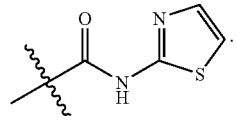

28. The compound according to claim 7, wherein M is

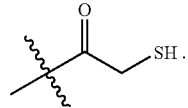

29. The compound according to claim 7, wherein M is

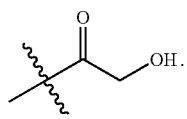

30. The compound according to claim 7, wherein M is

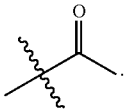

31. The compound according to claim 7, wherein M is

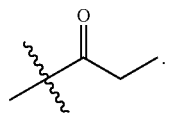

32. The compound according to claim 7, wherein M is

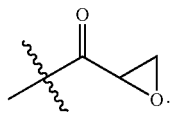

33. The compound according to claim 1, wherein -L-M is

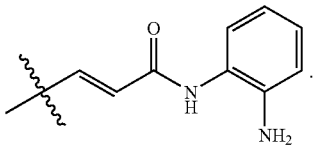

* * * * *

SEQUENCE LISTING

<160> NUMBER OF SEQ ID NOS: 8

<210> SEQ ID NO 1
<211> LENGTH: 513
<212> TYPE: PRT
<213> ORGANISM: Artificial
<220> FEATURE:
<223> OTHER INFORMATION: Residues 1-482 of HDAC1 with a
      "MSYYHHHHHHDYDIPTTENLYFQGAMEPGGS"tag at the N-terminus

<400> SEQUENCE: 1

```
Met Ser Tyr Tyr His His His His His Asp Tyr Asp Ile Pro Thr
1               5                   10                  15

Thr Glu Asn Leu Tyr Phe Gln Gly Ala Met Glu Pro Gly Gly Ser Met
                20                  25                  30

Ala Gln Thr Gln Gly Thr Arg Arg Lys Val Cys Tyr Tyr Tyr Asp Gly
            35                  40                  45

Asp Val Gly Asn Tyr Tyr Tyr Gly Gln Gly His Pro Met Lys Pro His
    50                  55                  60

Arg Ile Arg Met Thr His Asn Leu Leu Leu Asn Tyr Gly Leu Tyr Arg
65                  70                  75                  80

Lys Met Glu Ile Tyr Arg Pro His Lys Ala Asn Ala Glu Glu Met Thr
                85                  90                  95

Lys Tyr His Ser Asp Asp Tyr Ile Lys Phe Leu Arg Ser Ile Arg Pro
                100                 105                 110

Asp Asn Met Ser Glu Tyr Ser Lys Gln Met Gln Arg Phe Asn Val Gly
            115                 120                 125

Glu Asp Cys Pro Val Phe Asp Gly Leu Phe Glu Phe Cys Gln Leu Ser
    130                 135                 140

Thr Gly Gly Ser Val Ala Ser Ala Val Lys Leu Asn Lys Gln Gln Thr
145                 150                 155                 160

Asp Ile Ala Val Asn Trp Ala Gly Gly Leu His His Ala Lys Lys Ser
                165                 170                 175

Glu Ala Ser Gly Phe Cys Tyr Val Asn Asp Ile Val Leu Ala Ile Leu
            180                 185                 190

Glu Leu Leu Lys Tyr His Gln Arg Val Leu Tyr Ile Asp Ile Asp Ile
                195                 200                 205

His His Gly Asp Gly Val Glu Glu Ala Phe Tyr Thr Thr Asp Arg Val
    210                 215                 220

Met Thr Val Ser Phe His Lys Tyr Gly Glu Tyr Phe Pro Gly Thr Gly
225                 230                 235                 240

Asp Leu Arg Asp Ile Gly Ala Gly Lys Gly Lys Tyr Tyr Ala Val Asn
                245                 250                 255

Tyr Pro Leu Arg Asp Gly Ile Asp Asp Glu Ser Tyr Glu Ala Ile Phe
            260                 265                 270

Lys Pro Val Met Ser Lys Val Met Glu Met Phe Gln Pro Ser Ala Val
            275                 280                 285

Val Leu Gln Cys Gly Ser Asp Ser Leu Ser Gly Asp Arg Leu Gly Cys
    290                 295                 300

Phe Asn Leu Thr Ile Lys Gly His Ala Lys Cys Val Glu Phe Val Lys
305                 310                 315                 320
```

```
Ser Phe Asn Leu Pro Met Leu Met Leu Gly Gly Gly Tyr Thr Ile
            325                 330                 335

Arg Asn Val Ala Arg Cys Trp Thr Tyr Glu Thr Ala Val Ala Leu Asp
            340                 345                 350

Thr Glu Ile Pro Asn Glu Leu Pro Tyr Asn Asp Tyr Phe Glu Tyr Phe
            355                 360                 365

Gly Pro Asp Phe Lys Leu His Ile Ser Pro Ser Asn Met Thr Asn Gln
            370                 375                 380

Asn Thr Asn Glu Tyr Leu Glu Lys Ile Lys Gln Arg Leu Phe Glu Asn
385                 390                 395                 400

Leu Arg Met Leu Pro His Ala Pro Gly Val Gln Met Gln Ala Ile Pro
            405                 410                 415

Glu Asp Ala Ile Pro Glu Glu Ser Gly Asp Glu Asp Glu Asp Asp Pro
            420                 425                 430

Asp Lys Arg Ile Ser Ile Cys Ser Ser Asp Lys Arg Ile Ala Cys Glu
            435                 440                 445

Glu Glu Phe Ser Asp Ser Glu Glu Glu Gly Glu Gly Gly Arg Lys Asn
            450                 455                 460

Ser Ser Asn Phe Lys Lys Ala Lys Arg Val Lys Thr Glu Asp Glu Lys
465                 470                 475                 480

Glu Lys Asp Pro Glu Glu Lys Lys Glu Val Thr Glu Glu Glu Lys Thr
            485                 490                 495

Lys Glu Glu Lys Pro Glu Ala Lys Gly Val Lys Glu Glu Val Lys Leu
            500                 505                 510

Ala

<210> SEQ ID NO 2
<211> LENGTH: 1542
<212> TYPE: DNA
<213> ORGANISM: Artificial
<220> FEATURE:
<223> OTHER INFORMATION: DNA sequence encoding residues 1-482 of HDAC1
      with a "MSYYHHHHHHDYDIPTTENLYFQGAMEPGGS" tag at the N-terminus

<400> SEQUENCE: 2
atgtcgtact accatcacca tcaccatcac gattacgata tcccaacgac cgaaaacctg      60
tattttcagg gcgccatgga acccggggga tccatggcgc agacgcaggg caccccggagg    120 aaagtctgtt actactacga cggggatgtt ggaaattact attatggaca aggccaccca    180
atgaagcctc accgaatccg catgactcat aatttgctgc tcaactatgg tctctaccga    240
aaaatggaaa tctatcgccc tcacaaagcc aatgctgagg agatgaccaa gtaccacagc    300
gatgactaca ttaaattctt gcgctccatc cgtccagata acatgtcgga gtacagcaag    360
cagatgcaga gattcaacgt tggtgaggac tgtccagtat cgatggcct gtttgagttc    420 tgtcagttgt ctactggtgg ttctgtggca agtgctgtga acttaataa gcagcagacg    480 gacatcgctg tgaattgggc tgggggcctg caccatgcaa agaagtccga ggcatctggc    540
ttctgttacg tcaatgatat cgtcttggcc atcctggaac tgctaaagta tcaccagagg    600
gtgctgtaca ttgacattga tattcaccat ggtgacggcg tggaagaggc cttctacacc    660
acggaccggg tcatgactgt gtcctttcat aagtatggag agtacttccc aggaactggg    720
gacctacggg atatcggggc tggcaaaggc aagtattatg ctgttaacta cccgctccga    780
gacgggattg atgacgagtc ctatgaggcc attttcaagc cggtcatgtc caaagtaatg    840
gagatgttcc agcctagtgc ggtggtctta cagtgtggct cagactccct atctgggat    900
```

-continued

```
cggttaggtt gcttcaatct aactatcaaa ggacacgcca agtgtgtgga atttgtcaag      960
agctttaacc tgcctatgct gatgctggga ggcggtggtt acaccattcg taacgttgcc     1020
cggtgctgga catatgagac agctgtggcc ctggatacgg agatccctaa tgagcttcca     1080
tacaatgact actttgaata ctttggacca gatttcaagc tccacatcag tccttccaat     1140
atgactaacc agaacacgaa tgagtacctg gagaagatca acagcgact gtttgagaac      1200 cttagaatgc tgccgcacgc acctggggtc caaatgcagg cgattcctga ggacgccatc     1260
cctgaggaga gtggcgatga ggacgaagac gaccctgaca gcgcatctc gatctgctcc      1320 tctgacaaac gaattgcctg tgaggaagag ttctccgatt ctgaagagga gggagagggg     1380
ggccgcaaga actcttccaa cttcaaaaaa gccaagagag tcaaaacaga ggatgaaaaa     1440
gagaaagacc cagaggagaa gaaagaagtc accgaagagg agaaaccaa ggaggagaag      1500 ccagaagcca aggggtcaa ggaggaggtc aagttggcct ga                         1542
```

<210> SEQ ID NO 3
<211> LENGTH: 498
<212> TYPE: PRT
<213> ORGANISM: Artificial
<220> FEATURE:
<223> OTHER INFORMATION: Residues 1-488 of HDAC2 with a "GHHHHHH" tag at
      the C-terminus and a "MGS" tag at the N-terminus

<400> SEQUENCE: 3

```
Met Gly Ser Met Ala Tyr Ser Gln Gly Gly Lys Lys Lys Val Cys
1               5                   10                  15

Tyr Tyr Tyr Asp Gly Asp Ile Gly Asn Tyr Tyr Gly Gln Gly His
                20                  25                  30

Pro Met Lys Pro His Arg Ile Arg Met Thr His Asn Leu Leu Asn
                35                  40                  45

Tyr Gly Leu Tyr Arg Lys Met Glu Ile Tyr Arg Pro His Lys Ala Thr
        50                  55                  60

Ala Glu Glu Met Thr Lys Tyr His Ser Asp Glu Tyr Ile Lys Phe Leu
65                  70                  75                  80

Arg Ser Ile Arg Pro Asp Asn Met Ser Glu Tyr Ser Lys Gln Met Gln
                85                  90                  95

Arg Phe Asn Val Gly Glu Asp Cys Pro Val Phe Asp Gly Leu Phe Glu
                100                 105                 110

Phe Cys Gln Leu Ser Thr Gly Gly Ser Val Ala Gly Ala Val Lys Leu
            115                 120                 125

Asn Arg Gln Gln Thr Asp Met Ala Val Asn Trp Ala Gly Gly Leu His
        130                 135                 140

His Ala Lys Lys Ser Glu Ala Ser Gly Phe Cys Tyr Val Asn Asp Ile
145                 150                 155                 160

Val Leu Ala Ile Leu Glu Leu Leu Lys Tyr His Gln Arg Val Leu Tyr
                165                 170                 175

Ile Asp Ile Asp Ile His His Gly Asp Gly Val Glu Glu Ala Phe Tyr
            180                 185                 190

Thr Thr Asp Arg Val Met Thr Val Ser Phe His Lys Tyr Gly Glu Tyr
        195                 200                 205

Phe Pro Gly Thr Gly Asp Leu Arg Asp Ile Gly Ala Gly Lys Gly Lys
            210                 215                 220

Tyr Tyr Ala Val Asn Phe Pro Met Arg Asp Gly Ile Asp Asp Glu Ser
225                 230                 235                 240
```

```
Tyr Gly Gln Ile Phe Lys Pro Ile Ile Ser Lys Val Met Glu Met Tyr
            245                 250                 255

Gln Pro Ser Ala Val Val Leu Gln Cys Gly Ala Asp Ser Leu Ser Gly
            260                 265                 270

Asp Arg Leu Gly Cys Phe Asn Leu Thr Val Lys Gly His Ala Lys Cys
            275                 280                 285

Val Glu Val Val Lys Thr Phe Asn Leu Pro Leu Leu Met Leu Gly Gly
            290                 295                 300

Gly Gly Tyr Thr Ile Arg Asn Val Ala Arg Cys Trp Thr Tyr Glu Thr
305                 310                 315                 320

Ala Val Ala Leu Asp Cys Glu Ile Pro Asn Glu Leu Pro Tyr Asn Asp
                    325                 330                 335

Tyr Phe Glu Tyr Phe Gly Pro Asp Phe Lys Leu His Ile Ser Pro Ser
                340                 345                 350

Asn Met Thr Asn Gln Asn Thr Pro Glu Tyr Met Glu Lys Ile Lys Gln
            355                 360                 365

Arg Leu Phe Glu Asn Leu Arg Met Leu Pro His Ala Pro Gly Val Gln
            370                 375                 380

Met Gln Ala Ile Pro Glu Asp Ala Val His Glu Asp Ser Gly Asp Glu
385                 390                 395                 400

Asp Gly Glu Asp Pro Asp Lys Arg Ile Ser Ile Arg Ala Ser Asp Lys
                    405                 410                 415

Arg Ile Ala Cys Asp Glu Glu Phe Ser Asp Ser Glu Asp Gly Glu
                420                 425                 430

Gly Gly Arg Arg Asn Val Ala Asp His Lys Lys Gly Ala Lys Lys Ala
            435                 440                 445

Arg Ile Glu Glu Asp Lys Lys Glu Thr Glu Asp Lys Lys Thr Asp Val
450                 455                 460

Lys Glu Glu Asp Lys Ser Lys Asp Asn Ser Gly Glu Lys Thr Asp Thr
465                 470                 475                 480

Lys Gly Thr Lys Ser Glu Gln Leu Ser Asn Pro Gly His His His His
            485                 490                 495

His His

<210> SEQ ID NO 4
<211> LENGTH: 1497
<212> TYPE: DNA
<213> ORGANISM: Artificial
<220> FEATURE:
<223> OTHER INFORMATION: DNA sequence encoding residues 1-488 of HDAC2
      with a "GHHHHHH" tag at the C-terminus and a "MGS" tag at the
      N-terminus

<400> SEQUENCE: 4
atgggatcca tggcgtacag tcaaggaggc ggcaaaaaaa aagtctgcta ctactacgac      60
ggtgatattg gaaattatta ttatggacag ggtcatccca tgaagcctca tagaatccgc     120
atgacccata acttgctgtt aaattatggc ttatacagaa aaatggaaat atataggccc     180
cataaagcca ctgccgaaga atgacaaaa tatcacagtg atgagtatat caaatttcta     240
cggtcaataa gaccagataa catgtctgag tatagtaagc agatgcagag atttaatgtt     300
ggagaagatt gtccagtgtt tgatggactc tttgagtttt gtcagctctc aactggcggt     360
tcagttgctg gagctgtgaa gttaaaccga acagactg atatggctgt taattgggct     420
ggaggattac atcatgctaa gaatcgaaa gcatcaggat tctgttacgt taatgatatt     480
gtgcttgcca tccttgaatt actaaagtat catcagagag tcttatatat tgatatagat     540
```

-continued

```
attcatcatg gtgatggtgt tgaagaagct ttttatacaa cagatcgtgt aatgacggta      600
tcattccata aatatgggga atactttcct ggcacaggag acttgaggga tattggtgct      660
ggaaaaggca aatactatgc tgtcaatttt ccaatgagag atggtataga tgatgagtca      720
tatgggcaga tatttaagcc tattatctca aggtgatgg agatgtatca acctagtgct       780
gtggtattac agtgtggtgc agactcatta tctggtgata gactgggttg tttcaatcta      840
acagtcaaag gtcatgctaa atgtgtagaa gttgtaaaaa cttttaactt accattactg      900
atgcttggag gaggtggcta cacaatccgt aatgttgctc gatgttggac atatgagact      960
gcagttgccc ttgattgtga gattcccaat gagttgccat ataatgatta ctttgagtat     1020
tttggaccag acttcaaact gcatattagt ccttcaaaca tgacaaacca gaacactcca     1080
gaatatatgg aaaagataaa acagcgtttg tttgaaaatt tgcgcatgtt acctcatgca     1140
cctggtgtcc agatgcaagc tattccagaa gatgctgttc atgaagacag tggagatgaa     1200
gatggagaag atccagacaa gagaatttct attcgagcat cagacaagcg gatagcttgt     1260
gatgaagaat tctcagattc tgaggatgaa ggagaaggag gtcgaagaaa tgtggctgat     1320
cataagaaag gagcaaagaa agctagaatt gaagaagata agaaagaaac agaggacaaa     1380
aaaacagacg ttaaggaaga agataaatcc aaggacaaca gtggtgaaaa aacagatacc     1440
aaaggaacca aatcagaaca gctcagcaac cccgggcatc accatcacca tcactaa       1497
```

<210> SEQ ID NO 5
<211> LENGTH: 782
<212> TYPE: PRT
<213> ORGANISM: Artificial
<220> FEATURE:
<223> OTHER INFORMATION: Residues 73-845 of HDAC6 with a "GHHHHHH" tag
at the C-terminus and a "MP" tag at the N-terminus

<400> SEQUENCE: 5

```
Met Pro Gly Met Asp Leu Asn Leu Glu Ala Glu Ala Leu Ala Gly Thr
1               5                   10                  15

Gly Leu Val Leu Asp Glu Gln Leu Asn Glu Phe His Cys Leu Trp Asp
            20                  25                  30

Asp Ser Phe Pro Glu Gly Pro Glu Arg Leu His Ala Ile Lys Glu Gln
        35                  40                  45

Leu Ile Gln Glu Gly Leu Leu Asp Arg Cys Val Ser Phe Gln Ala Arg
    50                  55                  60

Phe Ala Glu Lys Glu Glu Leu Met Leu Val His Ser Leu Glu Tyr Ile
65                  70                  75                  80

Asp Leu Met Glu Thr Thr Gln Tyr Met Asn Glu Gly Glu Leu Arg Val
            85                  90                  95

Leu Ala Asp Thr Tyr Asp Ser Val Tyr Leu His Pro Asn Ser Tyr Ser
            100                 105                 110

Cys Ala Cys Leu Ala Ser Gly Ser Val Leu Arg Leu Val Asp Ala Val
        115                 120                 125

Leu Gly Ala Glu Ile Arg Asn Gly Met Ala Ile Ile Arg Pro Pro Gly
    130                 135                 140

His His Ala Gln His Ser Leu Met Asp Gly Tyr Cys Met Phe Asn His
145                 150                 155                 160

Val Ala Val Ala Ala Arg Tyr Ala Gln Gln Lys His Arg Ile Arg Arg
                165                 170                 175

Val Leu Ile Val Asp Trp Asp Val His His Gly Gln Gly Thr Gln Phe
            180                 185                 190
```

-continued

```
Thr Phe Asp Gln Asp Pro Ser Val Leu Tyr Phe Ser Ile His Arg Tyr
            195                 200                 205

Glu Gln Gly Arg Phe Trp Pro His Leu Lys Ala Ser Asn Trp Ser Thr
    210                 215                 220

Thr Gly Phe Gly Gln Gly Gln Gly Tyr Thr Ile Asn Val Pro Trp Asn
225                 230                 235                 240

Gln Val Gly Met Arg Asp Ala Asp Tyr Ile Ala Ala Phe Leu His Val
                245                 250                 255

Leu Leu Pro Val Ala Leu Glu Phe Gln Pro Gln Leu Val Leu Val Ala
            260                 265                 270

Ala Gly Phe Asp Ala Leu Gln Gly Asp Pro Lys Gly Glu Met Ala Ala
            275                 280                 285

Thr Pro Ala Gly Phe Ala Gln Leu Thr His Leu Leu Met Gly Leu Ala
        290                 295                 300

Gly Gly Lys Leu Ile Leu Ser Leu Glu Gly Gly Tyr Asn Leu Arg Ala
305                 310                 315                 320

Leu Ala Glu Gly Val Ser Ala Ser Leu His Thr Leu Leu Gly Asp Pro
                325                 330                 335

Cys Pro Met Leu Glu Ser Pro Gly Ala Pro Cys Arg Ser Ala Gln Ala
            340                 345                 350

Ser Val Ser Cys Ala Leu Glu Ala Leu Glu Pro Phe Trp Glu Val Leu
            355                 360                 365

Val Arg Ser Thr Glu Thr Val Glu Arg Asp Asn Met Glu Glu Asp Asn
        370                 375                 380

Val Glu Glu Ser Glu Glu Gly Pro Trp Glu Pro Pro Val Leu Pro
385                 390                 395                 400

Ile Leu Thr Trp Pro Val Leu Gln Ser Arg Thr Gly Leu Val Tyr Asp
                405                 410                 415

Gln Asn Met Met Asn His Cys Asn Leu Trp Asp Ser His His Pro Glu
            420                 425                 430

Val Pro Gln Arg Ile Leu Arg Ile Met Cys Arg Leu Glu Glu Leu Gly
            435                 440                 445

Leu Ala Gly Arg Cys Leu Thr Leu Thr Pro Arg Pro Ala Thr Glu Ala
450                 455                 460

Glu Leu Leu Thr Cys His Ser Ala Glu Tyr Val Gly His Leu Arg Ala
465                 470                 475                 480

Thr Glu Lys Met Lys Thr Arg Glu Leu His Arg Glu Ser Ser Asn Phe
                485                 490                 495

Asp Ser Ile Tyr Ile Cys Pro Ser Thr Phe Ala Cys Ala Gln Leu Ala
            500                 505                 510

Thr Gly Ala Ala Cys Arg Leu Val Glu Ala Val Leu Ser Gly Glu Val
        515                 520                 525

Leu Asn Gly Ala Ala Val Val Arg Pro Pro Gly His His Ala Glu Gln
530                 535                 540

Asp Ala Ala Cys Gly Phe Cys Phe Phe Asn Ser Val Ala Val Ala Ala
545                 550                 555                 560

Arg His Ala Gln Thr Ile Ser Gly His Ala Leu Arg Ile Leu Ile Val
                565                 570                 575

Asp Trp Asp Val His His Gly Asn Gly Thr Gln His Met Phe Glu Asp
            580                 585                 590

Asp Pro Ser Val Leu Tyr Val Ser Leu His Arg Tyr Asp His Gly Thr
            595                 600                 605
```

```
Phe Phe Pro Met Gly Asp Glu Gly Ala Ser Ser Gln Ile Gly Arg Ala
    610                 615                 620
Ala Gly Thr Gly Phe Thr Val Asn Val Ala Trp Asn Gly Pro Arg Met
625                 630                 635                 640
Gly Asp Ala Asp Tyr Leu Ala Ala Trp His Arg Leu Val Leu Pro Ile
                645                 650                 655
Ala Tyr Glu Phe Asn Pro Glu Leu Val Leu Val Ser Ala Gly Phe Asp
            660                 665                 670
Ala Ala Arg Gly Asp Pro Leu Gly Gly Cys Gln Val Ser Pro Glu Gly
        675                 680                 685
Tyr Ala His Leu Thr His Leu Leu Met Gly Leu Ala Ser Gly Arg Ile
    690                 695                 700
Ile Leu Ile Leu Glu Gly Gly Tyr Asn Leu Thr Ser Ile Ser Glu Ser
705                 710                 715                 720
Met Ala Ala Cys Thr Arg Ser Leu Leu Gly Asp Pro Pro Leu Leu
                725                 730                 735
Thr Leu Pro Arg Pro Pro Leu Ser Gly Ala Leu Ala Ser Ile Thr Glu
            740                 745                 750
Thr Ile Gln Val His Arg Arg Tyr Trp Arg Ser Leu Arg Val Met Lys
        755                 760                 765
Val Glu Asp Arg Glu Gly Pro Gly His His His His His His
    770                 775                 780
```

<210> SEQ ID NO 6
<211> LENGTH: 2349
<212> TYPE: DNA
<213> ORGANISM: Artificial
<220> FEATURE:
<223> OTHER INFORMATION: DNA encoding residues 73-845 of HDAC6 with a "GHHHHHH" tag at the C-terminus and a "MP" tag at the N-terminus

<400> SEQUENCE: 6

```
atgcccggga tggatctgaa ccttgaggct gaagcactgg ctggcactgg cttggtgttg      60
gatgagcagt taaatgaatt ccattgcctc tgggatgaca gcttcccgga aggccctgag     120
cggctccatg ccatcaagga gcaactgatc caggagggcc tcctagatcg ctgcgtgtcc     180
tttcaggccc ggtttgctga aaaggaagag ctgatgttgg ttcacagcct agaatatatt     240
gatctgatgg aaacaaccca gtacatgaat gagggagaac tccgtgtcct agcagacacc     300
tacgactcag tttatctgca tccgaactca tactcctgtg cctgcctggc ctcaggctct     360
gtcctcaggc tggtggatgc ggtcctgggg gctgagatcc ggaatggcat ggccatcatt     420
aggcctcctg acatcacgcc cagcacagt cttatggatg ctattgcat gttcaaccac     480
gtggctgtgg cagcccgcta tgctcaacag aaacaccgca tccggagggt ccttatcgta     540
gattgggatg tgcaccacgg tcaaggaaca cagttcacct tcgaccagga ccccagtgtc     600
ctctatttct ccatccaccg ctacgagcag gtaggttct ggccccacct gaaggcctct     660
aactggtcca ccacaggttt cggccaaggc caaggatata ccatcaatgt gccttggaac     720
caggtgggga tgcgggatgc tgactacatt gctgctttcc tgcacgtcct gctgccagtc     780
gccctcgagt tccagcctca gctggtcctg gtggctgctg atttgatgc cctgcaaggg     840
gaccccaagg gtgagatggc cgccactccg gcagggttcg cccagctaac ccacctgctc     900
atgggtctgg caggaggcaa gctgatcctg tctctggagg gtggctacaa cctccgcgcc     960
ctggctgaag cgtcagtgc ttcgctccac acccttctgg agacccttg ccccatgctc    1020
gagtcacctg gtgcccctg ccggagtgcc caggcttcag tttcctgtgc tctggaagcc    1080
```

-continued

```
cttgagccct tctgggaggt tcttgtgaga tcaactgaga ccgtggagag ggacaacatg    1140
gaggaggaca atgtagagga gagcgaggag gaaggaccct gggagccccc tgtgctccca    1200
atcctgacat ggccagtgct acagtctcgc acagggctgg tctatgacca aaatatgatg    1260
aatcactgca acttgtggga cagccaccac cctgaggtac cccagcgcat cttgcggatc    1320
atgtgccgtc tggaggagct gggccttgcc gggcgctgcc tcaccctgac accgcgccct    1380
gccacagagg ctgagctgct cacctgtcac agtgctgagt acgtgggtca tctccgggcc    1440
acagagaaaa tgaaaacccg ggagctgcac cgtgagagtt ccaactttga ctccatctat    1500
atctgcccca gtaccttcgc ctgtgcacag cttgccactg gcgctgcctg ccgcctggtg    1560
gaggctgtgc tctcaggaga ggttctgaat ggtgctgctg tggtgcgtcc cccaggacac    1620
cacgcagagc aggatgcagc ttgcggtttt tgcttttca actctgtggc tgtggctgct    1680
cgccatgccc agactatcag tgggcatgcc tacggatcc tgattgtgga ttgggatgtc    1740
caccacggta atggaactca gcacatgttt gaggatgacc cagtgtgct atatgtgtcc    1800 ctgcaccgct atgatcatgg ccttcttc cccatggggg atgagggtgc cagcagccag    1860
atcggccggg ctgcgggcac aggcttcacc gtcaacgtgg catggaacgg gccccgcatg    1920
ggtgatgctg actacctagc tgcctggcat cgcctggtgc ttcccattgc ctacgagttt    1980
aacccagaac tggtgctggt ctcagctggc tttgatgctg cacgggggga tccgctgggg    2040
ggctgccagg tgtcacctga gggttatgcc cacctcaccc acctgctgat gggccttgcc    2100
agtggccgca ttatccttat cctagagggt ggctataacc tgacatccat ctcagagtcc    2160
atggctgcct gcactcgctc cctccttgga gacccaccac ccctgctgac cctgccacgg    2220
cccccactat caggggccct ggcctcaatc actgagacca tccaagtcca tcgcagatac    2280
tggcgcagct acgggtcat gaaggtagaa gacagagaag acccgggca tcaccatcac    2340 catcactaa                                                            2349
```

<210> SEQ ID NO 7
<211> LENGTH: 385
<212> TYPE: PRT
<213> ORGANISM: Artificial
<220> FEATURE:
<223> OTHER INFORMATION: Residues 1-377 of HDAC8 with a "MHHHHHHP" tag
      at the N-terminus

<400> SEQUENCE: 7

```
Met His His His His His His Pro Met Glu Glu Pro Glu Glu Pro Ala
1               5                   10                  15

Asp Ser Gly Gln Ser Leu Val Pro Val Tyr Ile Tyr Ser Pro Glu Tyr
            20                  25                  30

Val Ser Met Cys Asp Ser Leu Ala Lys Ile Pro Lys Arg Ala Ser Met
        35                  40                  45

Val His Ser Leu Ile Glu Ala Tyr Ala Leu His Lys Gln Met Arg Ile
    50                  55                  60

Val Lys Pro Lys Val Ala Ser Met Glu Glu Met Ala Ala Phe His Thr
65                  70                  75                  80

Asp Ala Tyr Leu Gln His Leu Gln Lys Val Ser Gln Glu Gly Asp Asp
                85                  90                  95

Asp His Pro Asp Ser Ile Glu Tyr Gly Leu Gly Tyr Asp Cys Pro Ala
            100                 105                 110

Thr Glu Gly Ile Phe Asp Tyr Ala Ala Ala Ile Gly Gly Ala Thr Ile
        115                 120                 125
```

Thr Ala Ala Gln Cys Leu Ile Asp Gly Met Cys Lys Val Ala Ile Asn
    130                 135                 140
Trp Ser Gly Gly Trp His His Ala Lys Lys Asp Glu Ala Ser Gly Phe
145                 150                 155                 160
Cys Tyr Leu Asn Asp Ala Val Leu Gly Ile Leu Arg Leu Arg Arg Lys
                165                 170                 175
Phe Glu Arg Ile Leu Tyr Val Asp Leu Asp Leu His His Gly Asp Gly
            180                 185                 190
Val Glu Asp Ala Phe Ser Phe Thr Ser Lys Val Met Thr Val Ser Leu
        195                 200                 205
His Lys Phe Ser Pro Gly Phe Phe Pro Gly Thr Gly Asp Val Ser Asp
    210                 215                 220
Val Gly Leu Gly Lys Gly Arg Tyr Tyr Ser Val Asn Val Pro Ile Gln
225                 230                 235                 240
Asp Gly Ile Gln Asp Glu Lys Tyr Tyr Gln Ile Cys Glu Ser Val Leu
                245                 250                 255
Lys Glu Val Tyr Gln Ala Phe Asn Pro Lys Ala Val Val Leu Gln Leu
            260                 265                 270
Gly Ala Asp Thr Ile Ala Gly Asp Pro Met Cys Ser Phe Asn Met Thr
        275                 280                 285
Pro Val Gly Ile Gly Lys Cys Leu Lys Tyr Ile Leu Gln Trp Gln Leu
    290                 295                 300
Ala Thr Leu Ile Leu Gly Gly Gly Gly Tyr Asn Leu Ala Asn Thr Ala
305                 310                 315                 320
Arg Cys Trp Thr Tyr Leu Thr Gly Val Ile Leu Gly Lys Thr Leu Ser
                325                 330                 335
Ser Glu Ile Pro Asp His Glu Phe Phe Thr Ala Tyr Gly Pro Asp Tyr
            340                 345                 350
Val Leu Glu Ile Thr Pro Ser Cys Arg Pro Asp Arg Asn Glu Pro His
        355                 360                 365
Arg Ile Gln Gln Ile Leu Asn Tyr Ile Lys Gly Asn Leu Lys His Val
    370                 375                 380
Val
385

<210> SEQ ID NO 8
<211> LENGTH: 1158
<212> TYPE: DNA
<213> ORGANISM: Artificial
<220> FEATURE:
<223> OTHER INFORMATION: DNA encoding residues 1-377 of HDAC8 with a
      "MHHHHHP" tag at theN-terminus

<400> SEQUENCE: 8
atgcaccatc accatcacca tcccatggag gagccggagg aaccggcgga cagtgggcag    60
tcgctggtcc cggtttatat ctatagtccc gagtatgtca gtatgtgtga ctccctggcc   120
aagatcccca acgggccag tatggtgcat tctttgattg aagcatatgc actgcataag   180
cagatgagga tagttaagcc taaagtggcc tccatggagg agatggccgc cttccacact   240
gatgcttatc tgcagcatct ccagaaggtc agccaagagg gcgatgatga tcatccggac   300
tccatagaat atgggctagg ttatgactgc ccagccactg aagggatatt tgactatgca   360
gcagctatag gagggctac gatcacagct gcccaatgcc tgattgacgg aatgtgcaaa   420
gtagcaatta ctggtctggg agggtggcat catgcaaaga aagatgaagc atctggtttt   480

```
tgttatctca atgatgctgt cctgggaata ttacgattgc gacggaaatt tgagcgtatt      540
ctctacgtgg atttggatct gcaccatgga gatggtgtag aagacgcatt cagtttcacc      600
tccaaagtca tgaccgtgtc cctgcacaaa ttctccccag gattttcc aggaacaggt        660 gacgtgtctg atgttggcct agggaaggga cggtactaca gtgtaaatgt gcccattcag      720
gatggcatac aagatgaaaa atattaccag atctgtgaaa gtgtactaaa ggaagtatac      780
caagccttta atcccaaagc agtggtctta cagctgggag ctgacacaat agctggggat      840
cccatgtgct cctttaacat gactccagtg ggaattggca agtgtcttaa gtacatcctt      900
caatggcagt tggcaacact cattttggga ggaggaggct ataaccttgc caacacggct      960
cgatgctgga catacttgac cggggtcatc ctagggaaaa cactatcctc tgagatccca     1020
gatcatgagt ttttcacagc atatggtcct gattatgtgc tggaaatcac gccaagctgc     1080
cggccagacc gcaatgagcc ccaccgaatc caacaaatcc tcaactacat caaagggaat     1140
ctgaagcatg tggtctag                                                   1158
```